US 6,352,953 B1

(12) United States Patent
Seki et al.

(10) Patent No.: US 6,352,953 B1
(45) Date of Patent: Mar. 5, 2002

(54) CATALYST CONTAINING NOVEL TRANSITION METAL COMPOUND FOR POLYMERIZATION OF OLEFINS

(75) Inventors: Takashi Seki; Hiroyuki Shimizu; Akira Sano, all of Kawasaki (JP)

(73) Assignee: Japan Polyolefins Co., Ltd., Tokyo (JP)

(*) Notice: Subject to any disclaimer, the term of this patent is extended or adjusted under 35 U.S.C. 154(b) by 0 days.

(21) Appl. No.: 09/685,015

(22) Filed: Oct. 9, 2000

Related U.S. Application Data

(62) Division of application No. 09/229,882, filed on Jan. 13, 1999, now Pat. No. 6,150,544.

(30) Foreign Application Priority Data

Jun. 30, 1998  (JP) .......................................... 10-184482

(51) Int. Cl.[7] .......................... B01J 31/00; C07F 17/00; C08F 4/44
(52) U.S. Cl. .................. 502/103; 502/114; 502/120; 502/154; 526/160; 526/943; 556/6; 556/27; 556/53
(58) Field of Search ................................ 556/6, 27, 53; 502/154, 103, 114, 120; 526/160, 943

(56) References Cited

U.S. PATENT DOCUMENTS 4,404,344 A     9/1983  Sinn et al. .................. 526/160

FOREIGN PATENT DOCUMENTS

| JP | 58-19309 | 2/1983 |
| JP | 7-37488 | 4/1995 |

Primary Examiner—Porfirio Nazario-Gonzalez
(74) Attorney, Agent, or Firm—Akin, Gump, Strauss, Hauer & Feld, L.L.P.

(57) ABSTRACT

Disclosed is a novel transition metal composition of a metaracycle structure represented by the formula (I)

Figure 1:
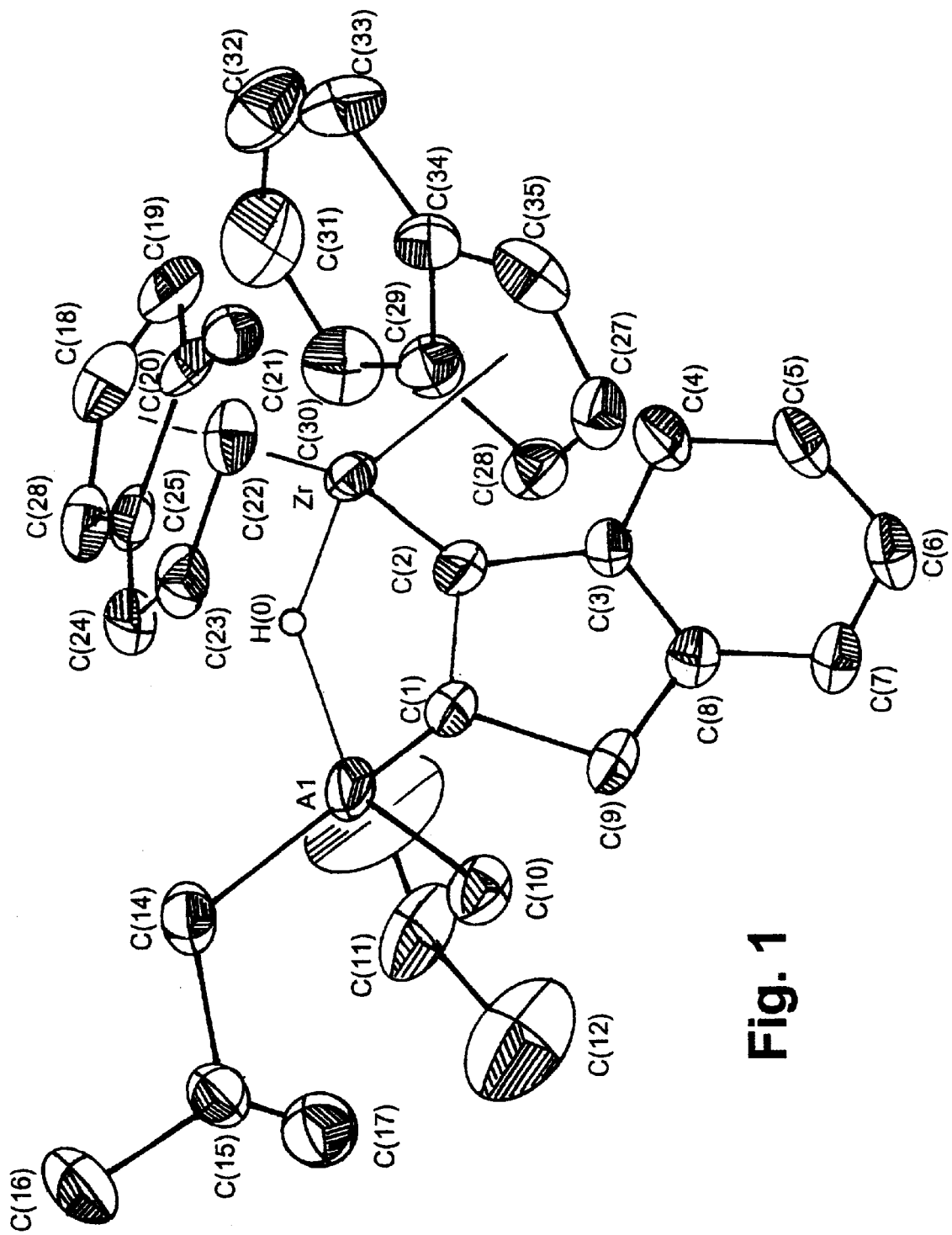

wherein $M^1$ is an element of Group IVB in the Periodic Table, $M^2$ is an element of Group IIIA in the Periodic Table, $R^1$ and $R^2$ each are for instance a cyclopentadienyl group, $R^3$ and $R^4$ each are for instance a hydrocarbon group, R5 and R6 each are a hydrogen atom and R7 and R8 indicate an indan ring formed by bonding to each other.

13 Claims, 1 Drawing Sheet

CATALYST CONTAINING NOVEL TRANSITION METAL COMPOUND FOR POLYMERIZATION OF OLEFINS

CROSS-REFERENCE TO RELATED APPLICATION

This application is a divisional of U.S. application Ser. No. 09/229,882 filed Jan. 13, 1999, now U.S. Pat. No. 6,150,544.

BACKGROUND OF THE INVENTION

1. Field of the Invention

This invention relates to a novel transition metal which is useful as a catalyst for polymerization of olefins.

2. Prior Art

It is well known to produce ethylene polymers or ethylene-α-olefin copolymers with use of a catalyst composition comprising a zirconium compound, a transition metal compound such as titanocene and hafnocene compounds and an aluminoxane compound. This prior art catalyst is liable to form such a polymers which is of an extremely high catalytic activity and has a narrow molecular weight distribution and modal distribution. Such known transition metal compounds are represented by the formula (cyclopentadienyl)$_2$MeRHal wherein R is a cyclopentadienyl or $C_1$–$C_6$ alkyl group or halogen, particularly chlorine, Me is a transition metal, particularly zirconium and Hal is halogen, particularly chlorine. Specific examples are bis(cyclopentadienyl) zirconiumdichloride (Cp$_2$ZrCl$_2$) and bis(cyclopentadienyl) zirconiummonomethylmonochloride Cp$_2$Zr(CH$_3$)Cl as disclosed in Japanese Laid-Open Patent Publication No. 58-19309. U.S. Pat. No. 4,404,344 also discloses a zirconium compound represented by the formula Cp$_2$MeY$_2$ wherein Me is zirconium, Y is hydrogen, a $C_1$–$C_5$ alkyl group, a $C_1$–$C_5$ metalalkyl group or a group of such as CH$_2$AlR$_2$, CH$_2$CH$_2$AlR$_2$ and CH$_2$CH(AlR$_2$)$_2$ of which each R is a $C_1$–$C_5$ alkyl group or a $C_1$–$C_5$ metalloalkyl group.

Moreover, another compounds are well known from Japanese Patent Publication No. 7-37488 disclosing $(C_5R'_m)_pR''_s$ $(C_5R'_m)MeQ_{3-p}$ and $R''_s(C_5R'_m)_2MeQ'$ wherein Me is zirconium or hafnium, each $(C_5R'_m)$ is a cyclopentadienyl group or a substituted cyclopentadienyl group, R' each may be the same or different and are one member selected from the group consisting of hydrogen and $C_1$–$C_{20}$ alkyl, alkenyl, aryl, alkylaryl and arylalkyl groups of which two adjacent members may form 4- through 6-membered condensed rings, R'' is a $C_1$–$C_4$ alkylene group, germanium, silicone, a phosphino group or an amino group which crosslink two rings $(C_5R'_m)$, Q each may be the same or different and are a $C_1$–$C_{20}$ aryl, alkyl, alkenyl, alkylaryl or arylalkyl group or halogen, Q' is a $C_1$–$C_{20}$ alkylidene, s=0 or 1, p=1 and, m=4 when s=1 and m=5 when s=0, and at least one of R' is a hydrocarbon group if m=5.

In recent years, there have been arising various demands for polyolefins in terms of physical properties and characteristics, such demands being directed to the production of polyolefins which are somewhat widened in molecular weight distribution or increased in molecular weight or which are completely free of halogen. It has been found that polyolefins tend to be effectively varied in properties and behaviors such as activity during polymerization depending on the type of a transition metal compound used therefor. Nowadays, a strong demand has been arising for a clean polyolefin free of halogen in view of problems in environment and hygienic.

SUMMARY OF THE INVENTION

An object of the present invention is to provide a novel transition metal compound which is stable in nature and eligible for use of the components of a polymerization catalyst for olefins.

The novel transition metal compound according to the invention is represented by the formula

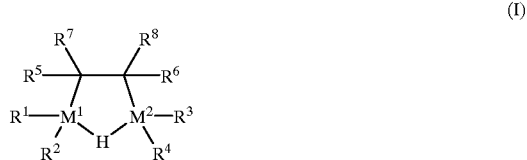

(I)

wherein $M^1$ is an element of Group IVB in the Periodic Table, $M^2$ is an element of Group IIIA in the Periodic Table, $R^1$ and $R^2$ each are a cyclopentadienyl group, a substituted cyclopentadienyl group, an indenyl group or a substituted indenyl group and may be bonded to each other through a $C_1$–$C_{18}$ hydrocarbon group and/or silylene group, $R^3$ and $R^4$ each are a hydrogen atom or a $C_1$–$C_{18}$ hydrocarbon group, $R^5$ and $R^6$ each are a hydrogen atom or a $C_1$–$C_{18}$ hydrocarbon group and $R^7$ and $R^8$ each are a hydrogen atom or a $C_1$–$C_{18}$ hydrocarbon group and may be bonded to each other to form one or more cyclic hydrocarbon group.

A typical example of the compound of the above formula (I) is represented by the formula

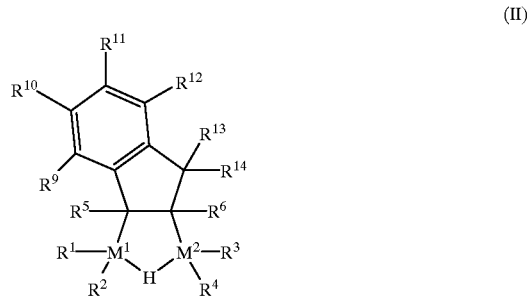

(II)

wherein $M^1$ is an element of Group IVB in the Periodic Table, $M^2$ is an element of Group IIIA in the Periodic Table, $R^1$ and $R^2$ each are a cyclopentadienyl group, a substituted cyclopentadienyl group, an indenyl group or a substituted indenyl group and may be bonded to each other through a $C_1$–$C_{18}$ hydrocarbon group and/or silylene group, $R^3$ and $R^4$ each are a hydrogen atom or a $C_1$–$C_{18}$ hydrocarbon group, $R^5$, $R^6$, $R^9$, $R^{10}$, $R^{11}$, $R^{12}$, $R^{13}$ and $R^{14}$ each are a hydrogen atom or a $C_1$–$C_{18}$ hydrocarbon group and may be bonded to each other through a hydrocarbon group to form a cyclic hydrocarbon group.

The present invention provides a novel transition metal compound which is capable of becoming a catalyst component exhibiting an excellent catalytic activity when applied to polymerization of olefins. This novel transition metal compound can be synthesized without using a halogen-containing substance as a starting material and is a novel transition metal complex having a 5-membered ring formed by a transition metal compound of Group IVB, two carbons, a metal of Group III and hydrogen and the existence of such a transition metal complex has not ever been known. Furthermore, it has not been known to use this transition metal complex as a component of a catalyst for polymerization of olefins.

The novel transition metal compound of the invention is represented by the above-mentioned formula (I) and one of the features of this compound is exemplified by the metallacycle (5-membered ring) formed through the bond of carbon, carbon, $M^2$ (an element of Group IIIA in the Periodic Table) and hydrogen to $M^1$ (an element of Group IVB in the Periodic Table).

It is well known that a zirconocenemonoalkylmonohydride compound of which hydrogen and alkyl are bonded to zirconium forms a divalent zirconocene by reductive elimination reaction caused by the coupling of hydrogen and the hydrocarbon, as reported in "Organozirconium Compounds in Organic Synthesis" written by E. Negishi, T. Takahashi in SYNTHESIS, 1–19, January 1988. Such a zirconocenemonoalkylmonohydride compound is susceptible to the reductive elimination reaction and thus is difficult to stabilize whereas the novel transition metal compound of the invention can suppress the occurrence of the reductive elimination by the formation of a metallacycle (five-membered ring).

The inventive compound is characterized by its stereostructure which is stabilized due to the formation of metaracycle (five-membered ring) containing hydrogen. The five-membered ring of cyclopentadienyl groups or indenyl groups can rotate and thus if two identical ligands are bonded thereto they can not be distinguished. As to $Cp_2ZrCl_2$ (Formula A below), it is reported in J. Organomet. Chem., 1964, 2,329 that the 10 hydrogen atoms ($H^1$ of Formula A) bonding to the cyclopentadienyl group are classified of one single kind by $^1$H-NMR. As to $Cp_2Zr(Cl)CH_2SiMe_3$ (Formula B below), it is reported in J. Chem. Soc. Dalton Trans., 1973, 445 that the 10 hydrogen atoms ($H^2$ of Formula B below) bonding to the cyclopentadienyl group are likewise classified of one single kind by $^1$H-NMR. Furthermore, as to $Ind_2ZrCl_2$ (Formula C below), Bull. Soc. Chim. Fr., 1966, 3548 describes that the 6 hydrogen atoms ($H^3$, $H^4$ of Formula C) bonding to the 5-membered rings of the indenyl group are observed of two types by $^1$H-NMR.

(A)

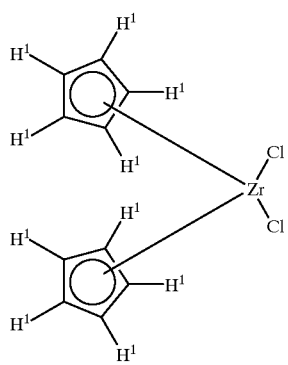

(B)

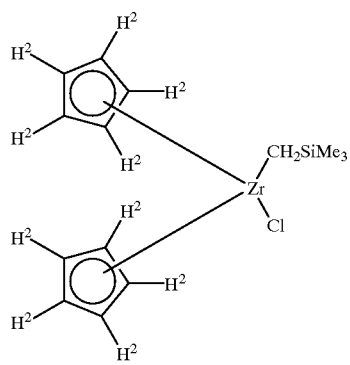

(C)

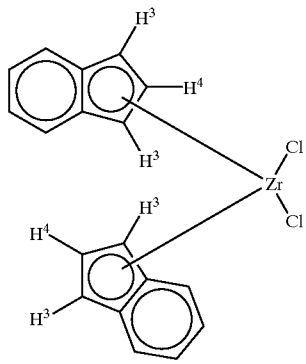

(D)

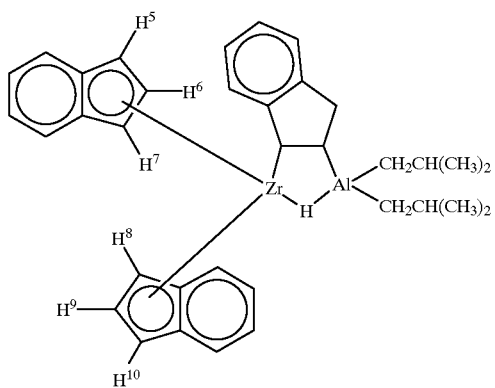

(E)

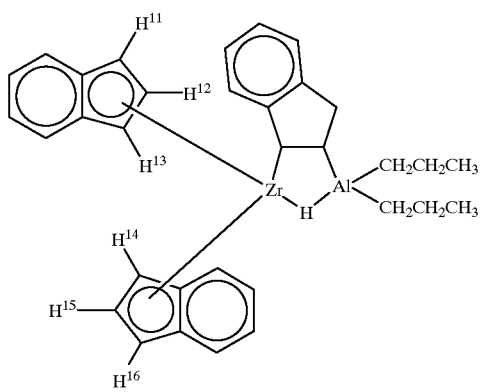

Whereas, as proved in Examples 1 and 2 hereinafter described, $^1$H-NMR analysis of the novel compounds as represented by Formulae D and E above, of the invention reveals that the 6 hydrogen atoms in total ($H^5$, $H^6$, $H^7$, $H^8$, $H^9$ and $H^{10}$ of Formula D and $H^{11}$, $H^{12}$, $H^{13}$, $H^{14}$, $H^{15}$ and $H^{16}$ of Formula E) are observed individually. $^1$H-NMR data of Examples 1 indicates that these hydrogens are present at a peak of 5.8 ppm, 5.5 ppm, 5.4 ppm, 5.1 ppm, 4.6 ppm, and 4.3 ppm, while $^1$H-NMR data of Examples 2 indicates that these hydrogens are present at a peak of 5.6 ppm, 5.4 ppm, 5.3 ppm, 5.3 ppm, 4.7 ppm and 4.4 ppm.

By these facts meant is that all of these 6 hydrogens are distinguished by the time scale of NMR and the rotation of the indenyl group is restrained. These facts has been confirmed by X-ray diffraction.

The features of the novel transition metal compound according to the invention are summarized as follows:

1. $M^1$ of an element of Group IVB in the Periodic Table bonding through hydrogen to $M^2$ of an element of Group IIIA in the Periodic Table
2. The stabilized stereostructure of the compound by the formation of metallacycle
3. No use of halogen in the process of synthesizing

BREIF DESCRIPTION OF THE DRAWING

FIG. 1 is a projectional view of the zirconium compound synthesized in Example 1, drawn by a computer based on the data of X-ray crystallography.

DETAILED DESCRIPTION OF THE INVENTION

In the above-described formula (I), $M^1$ denotes an element of Group IVB in the Periodic Table and is preferably zirconium, titanium and hafnium, among which zirconium is particularly preferred. $M^2$ denotes an element of Group IIIA in the Periodic Table and is preferably aluminum and boron, among which aluminum is particularly preferred.

$R^1$ and $R^2$ may be the same or different and each are a cyclopentadienyl, substituted cyclopentadienyl, indenyl or substituted indenyl group. The substituent of each of the substituted cyclopentadienyl and substituted indenyl groups may be a $C_1$–$C_{18}$, preferably $C_1$–$C_{12}$ hydrocarbon group including an alkyl group such as methyl, ethyl, propyl, isopropyl, butyl, isobutyl, t-butyl, pentyl, hexyl, and octyl groups, an alkenyl group such as vinyl and allyl, an aryl group such as phenyl, tolyl and xylyl, an aralkyl group such as benzyl, phenethyl, styryl and neophyl. $R^1$ and $R^2$ may be bonded to each other via a silylene group or a $C_1$–$C_{18}$ hydrocarbon including an alkylene group such as methylene, ethylene and isopropylene; an alkylene group with an aryl substituent such as diphenylmethylene, methylphenylmethylene and ditolylmethylene; an alkylene group with an alkenyl substituent such as divinylmethylene and diallylmethylene; and an alkylene group with an aralkyl substituent such as benzyl, phenethyl, styryl and neophyl. The silylene group may be a silylene group with an alkyl group such as dimethylsilylene and diethylsilylene; a silylene group with an aryl substituent such as diphenysilylene, methylphenysilylene and ditolylsilylene; a silylene group with an alkenyl substituent such as divinylsilylene and diallylsilylene; and a silylene group with an aralkyl substituent such as benzyl, phenethyl, styryl and neophyl.

$R^3$ and $R^4$ may be the same or different and each denote a hydrogen atom and a $C_1$–$C_{12}$, preferably $C_1$–$C_8$ hydrocarbon group. Such a hydrocarbon group includes an alkyl group such as methyl, ethyl, propyl, isopropyl, cyclopropyl, butyl, isobutyl, t-butyl, pentyl, isopentyl, neopentyl, cyclopentyl, hexyl, isohexyl, cyclohexyl, heptyl, octyl decyl, and dodecyl; an alkenyl group such as vinyl and allyl; an aryl group such as phenyl, tolyl, xylyl, mesityl, indenyl and naphthyl; and an aralkyl group such as benzyl, trityl, phenethyl, styryl, benzhydril, phenylbutyl, phenylpropyl and neophyl.

$R^5$, $R^6$, $R^7$ and $R^8$ may be the same or different and each denote a hydrogen atom or a $C_1$–$C_{18}$, preferably $C_1$–$C_{12}$, more preferably $C_1$–$C_8$ hydrocarbon group including an alkyl group such as methyl, ethyl, propyl, isopropyl, cyclopropyl, butyl, isobutyl, t-butyl, pentyl, isopentyl, neopentyl, cyclopentyl, hexyl, isohexyl, cyclohexyl, heptyl, octyl, decyl and dodecyl; an alkenyl group such as vinyl and allyl; an aryl group such as phenyl, tolyl, xylyl, mesityl, indenyl and naphthyl; and an aralkyl group such as benzyl, trityl, phenethyl, styryl, benzhydril, phenylbutyl, phenylpropyl and neophyl.

$R^5$, $R^6$, $R^7$, $R^8$ may be bonded to each other via a $C_1$–$C_{18}$, preferably $C_1$–$C_{12}$, more preferably $C_1$–$C_8$ hydrocarbon group including an alkyl group such as methyl, ethyl, propyl, isopropyl, cyclopropyl, butyl, isobutyl, t-butyl, pentyl, isopentyl, neopentyl, cyclopentyl, hexyl, isohexyl, cyclohexyl, heptyl, octyl, decyl, and dodecyl; an alkenyl group such as vinyl and allyl; an aryl group such as phenyl, tolyl, xylyl, mesityl, indenyl and naphthyl; and an aralkyl group such as benzyl, trityl, phenethyl, styryl, benzhydril, phenylbutyl, phenylpropyl and neophyl.

In the above-described formula (II), $M^1$ denotes an element of Group IVB in the Periodic Table and is preferably zirconium, titanium and hafnium, among which zirconium is particularly preferred. $M^2$ denotes an element of Group IIIA in the Periodic Table and is preferably aluminum and boron, among which aluminum is particularly preferred.

$R^1$ and $R^2$ may be the same or different and each are a cyclopentadienyl, substituted cyclopentadienyl, indenyl or substituted indenyl group. The substituent group of each of the substituted cyclopentadienyl and substituted indenyl groups may be a $C_1$–$C_{18}$, preferably $C_1$–$C_{12}$ hydrocarbon group including an alkyl group such as methyl, ethyl, propyl, isopropyl, butyl, isobutyl, t-butyl, pentyl, hexyl, and octyl groups, an alkenyl group such as vinyl and allyl, an aryl group such as phenyl, tolyl and xylyl, an aralkyl group such as benzyl, phenethyl, styryl and neophyl. These substituent groups may be present more than two in the number and not restricted to position. $R^1$ and $R^2$ may be bonded to each other via a silylene group or a $C_1$–$C_{18}$ hydrocarbon including an alkylene group such as methylene, ethylene and isopropylene; an alkylene group with an aryl substituent such as diphenylmethylene, methylphenylmethylene and ditolylmethylene; an alkylene group with an alkenyl substituent such as divinylmethylene and diallylmethylene; and an alkylene group with an aralkyl substituent such as benzyl, phenethyl, styryl and neophyl. The silylene group may be a silylene group with an alkyl group such as dimethylsilylene and diethylsilylene; a silylene group with an aryl substituent such as diphenysilylene, methylphenysilylene and ditolylsilylene; a silylene group with an alkenyl substituent such as divinylsilylene and diallylsilylene; and a silylene group with an aralkyl substituent such as benzyl, phenethyl, styryl and neophyl.

$R^3$ and $R^4$ may be the same or different and each denote a hydrogen atom and a $C_1$–$C_{18}$, preferably $C_1$–$C_{12}$, more preferably $C_1$–$C_8$ hydrocarbon group. Such a hydrocarbon group includes an alkyl group such as methyl, ethyl, propyl, isopropyl, cyclopropyl, butyl, isobutyl, t-butyl, pentyl, isopentyl, neopentyl, cyclopentyl, hexyl, isohexyl, cyclohexyl, heptyl, octyl, decyl and dodecyl; an alkenyl group such as vinyl and allyl; an aryl group such as phenyl, tolyl, xylyl, mesityl, indenyl and naphthyl; and an aralkyl group such as benzyl, trityl, phenethyl, styryl, benzhydril, phenylbutyl, phenylpropyl and neophyl.

$R^5$, $R^6$, $R^9$, $R^{10}$, $R^{11}$, $R^{12}$, $R^{13}$ and $R^{14}$ may be the same or different and each are a hydrogen atom or a $C_1$–$C_{18}$, preferably $C_1$–$C_{12}$, more preferably $C_1$–$C_8$ hydrocarbon group including an alkyl group such as methyl, ethyl, propyl, isopropyl, cyclopropyl, butyl, isobutyl, t-butyl, pentyl, isopentyl, neopentyl, cyclopentyl, hexyl, isohexyl, cyclohexyl, heptyl, octyl, decyl and dodecyl; an alkenyl group such as vinyl and allyl; an aryl group such as phenyl, tolyl, xylyl, mesityl, indenyl and naphthyl; and an aralkyl group such as benzyl, trityl, phenethyl, styryl , benzhydril, phenylbutyl, phenylpropyl and neophyl.

Two adjacent groups among $R^9$, $R^{10}$, $R^{11}$ and $R^{12}$ may be bonded to each other so as to form one or more cyclic compound.

Specific examples of the compound represented by formula (I) are give below

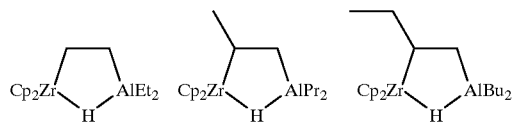

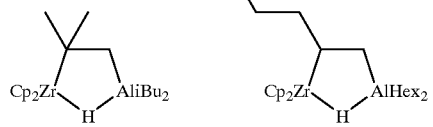

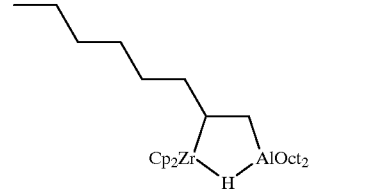

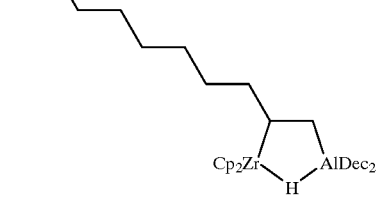

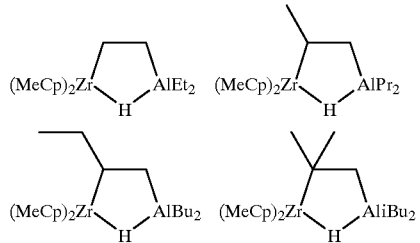

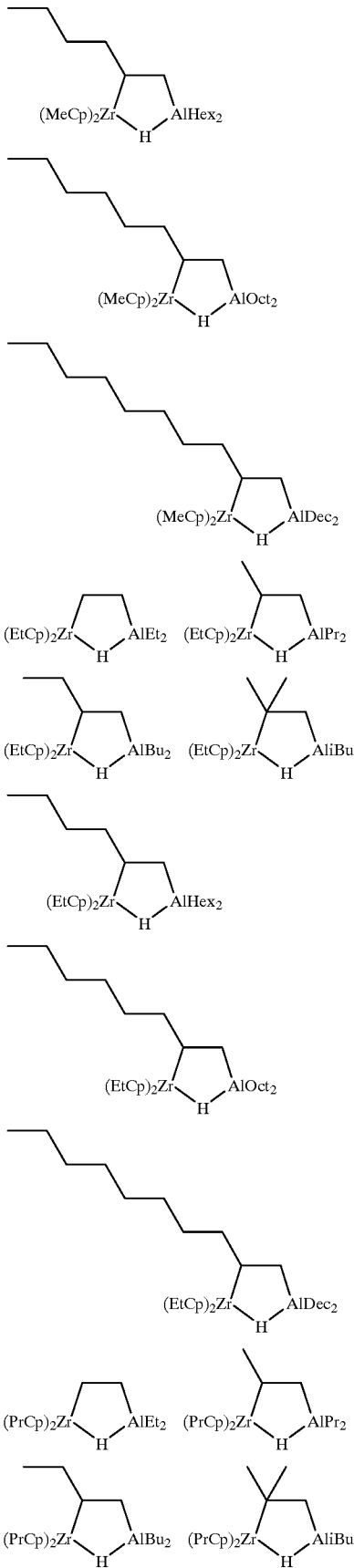

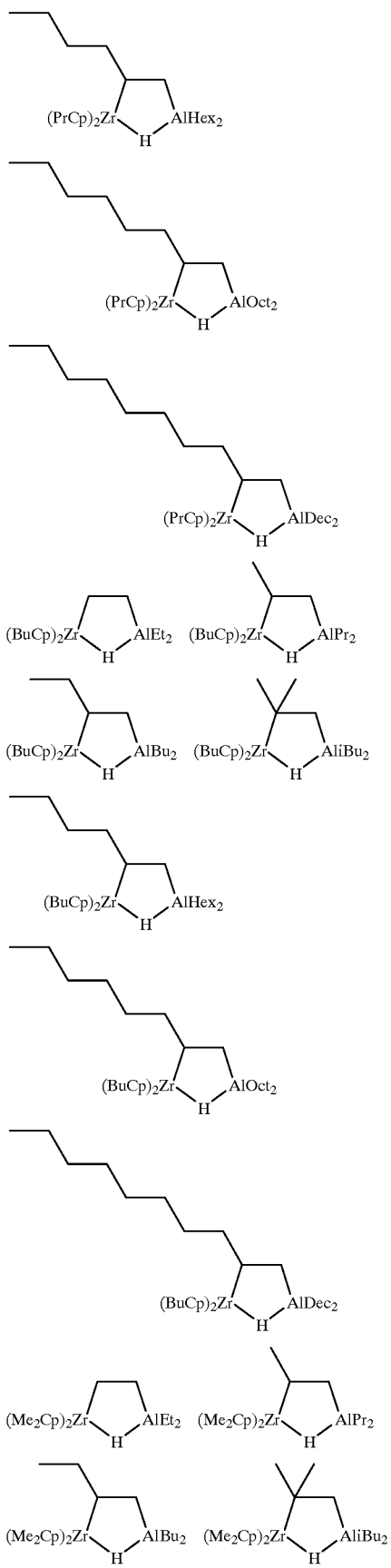
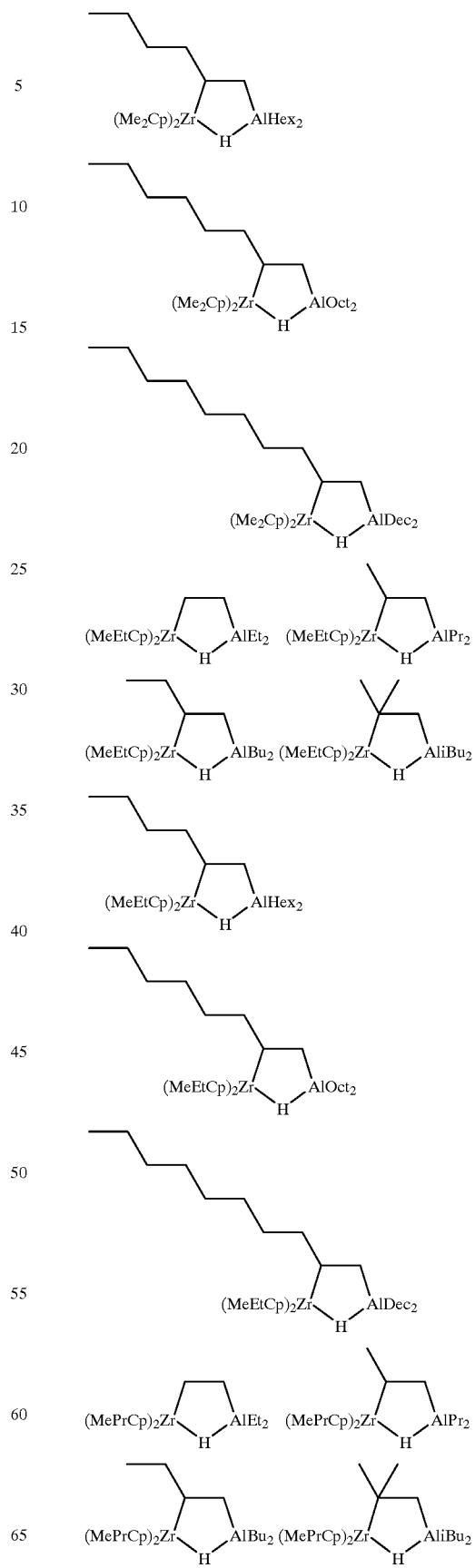

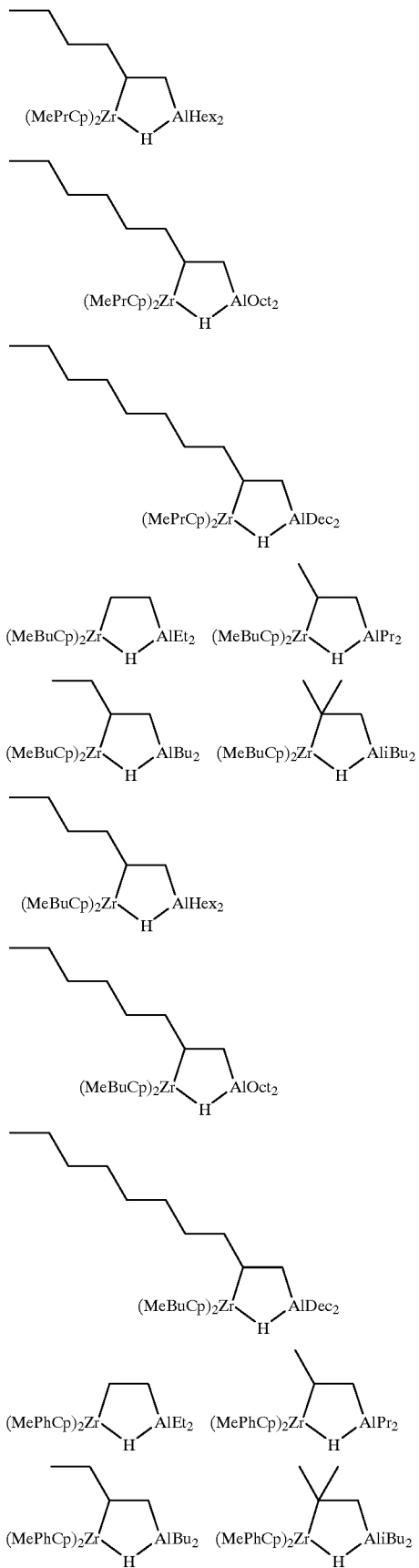
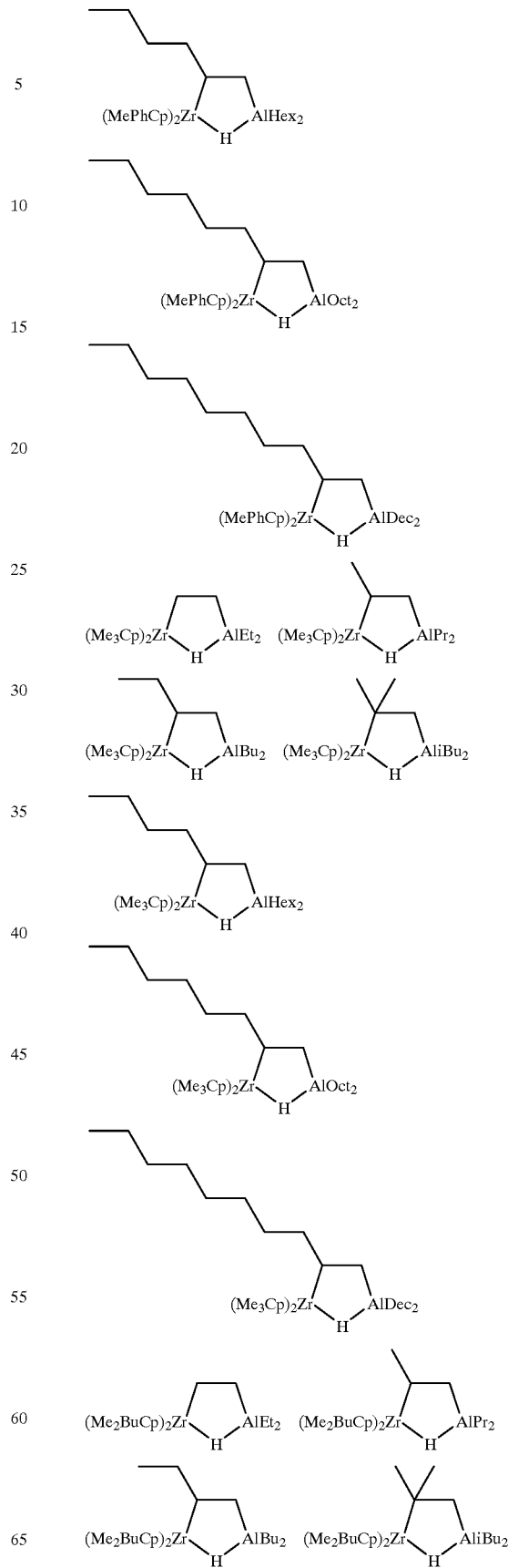

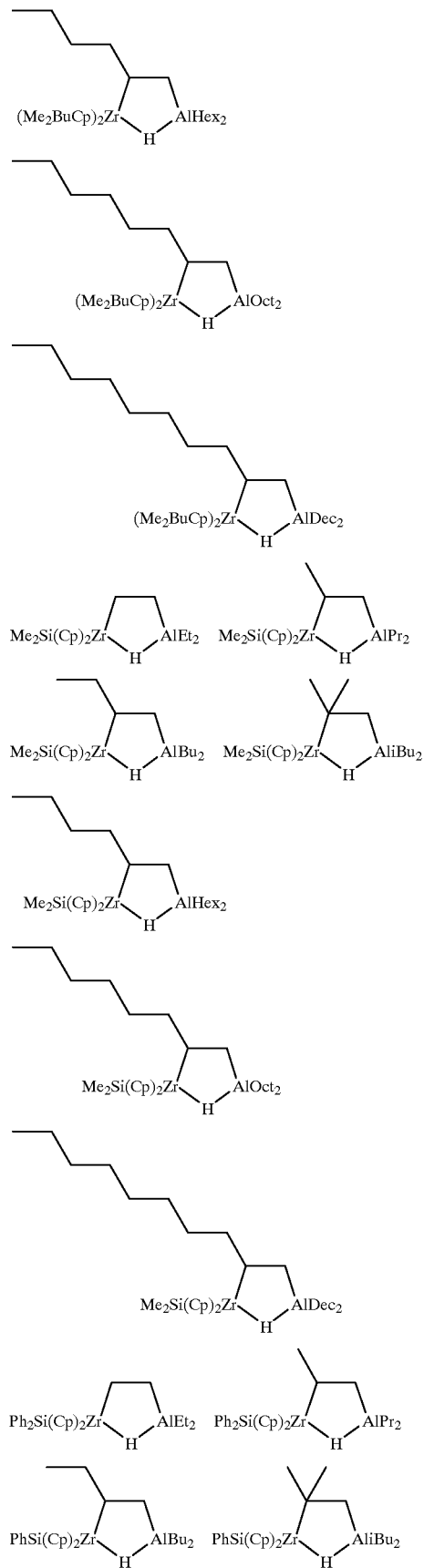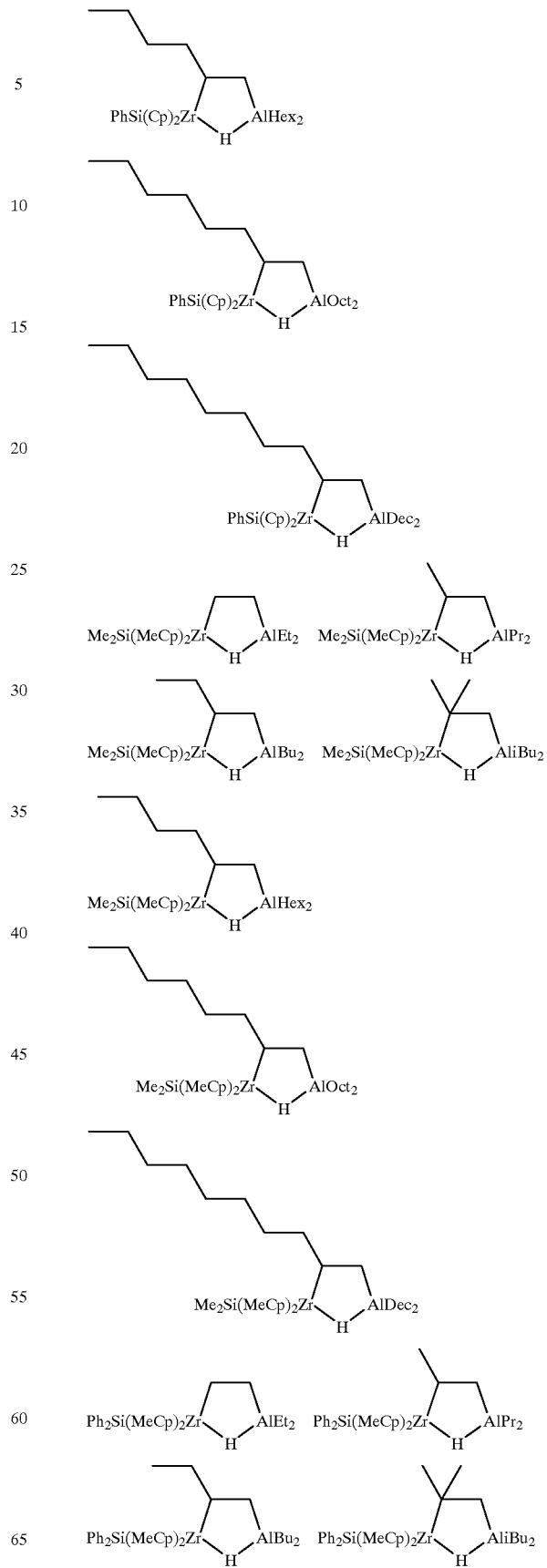

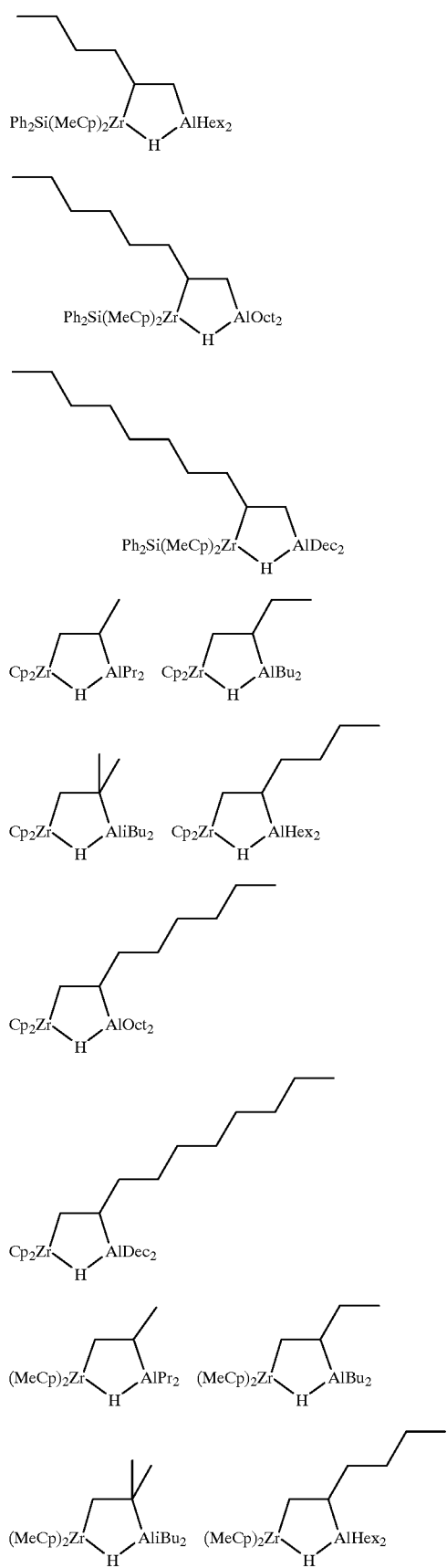
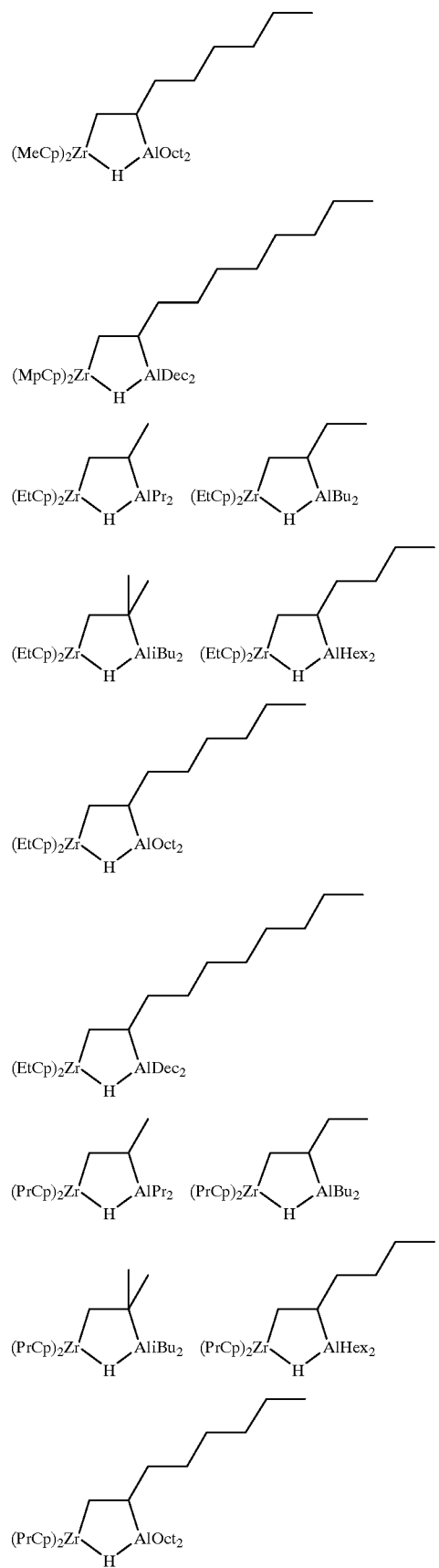

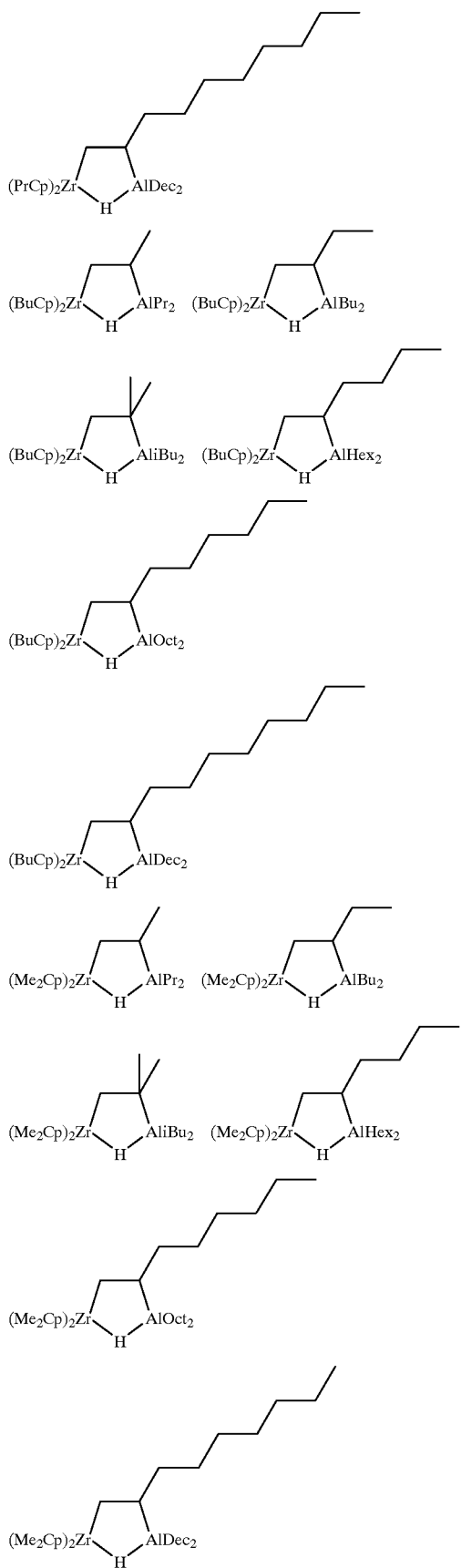
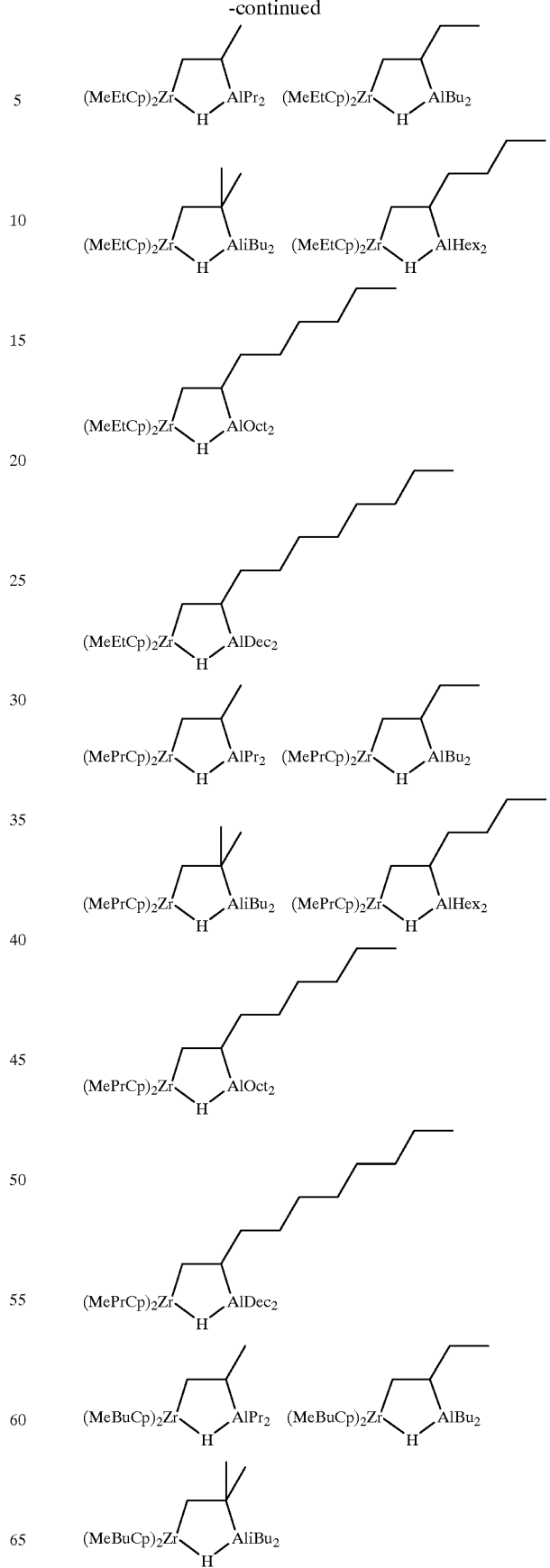

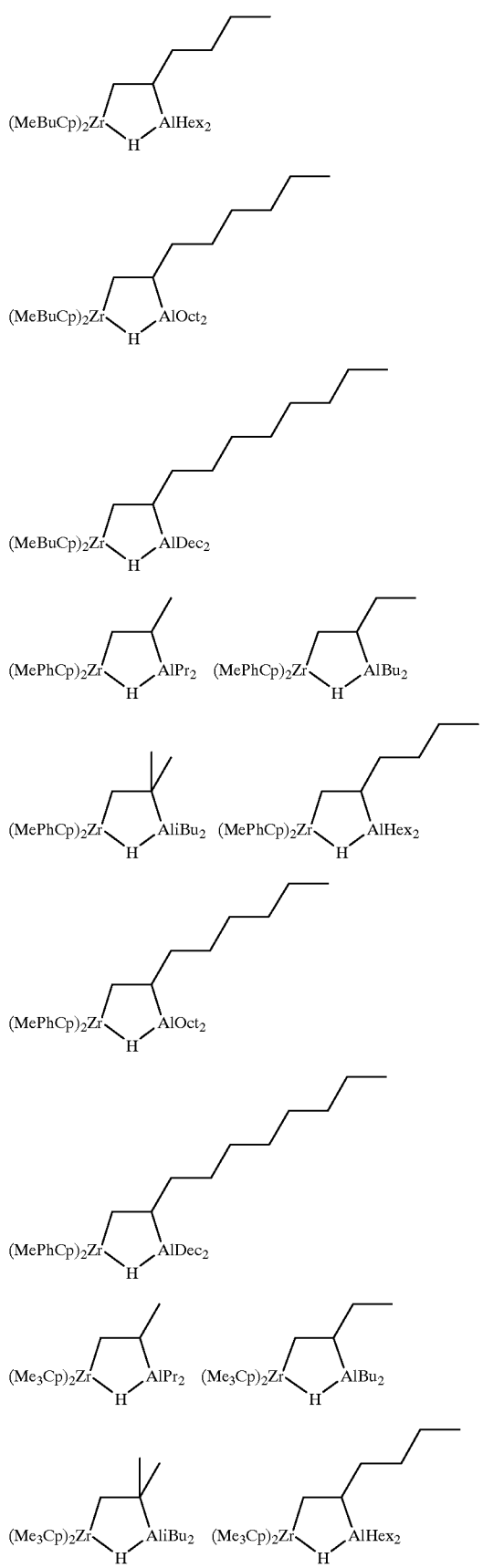
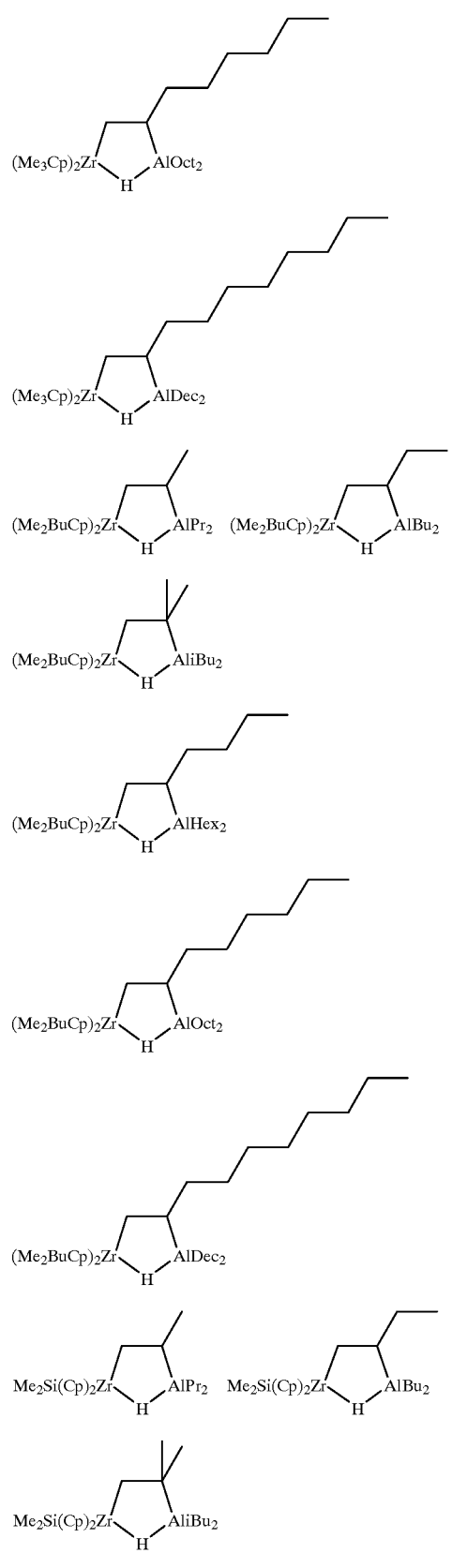

-continued
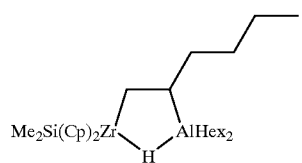
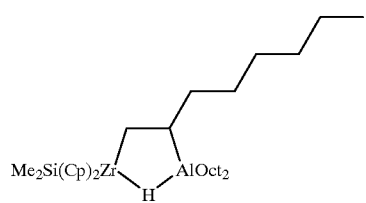
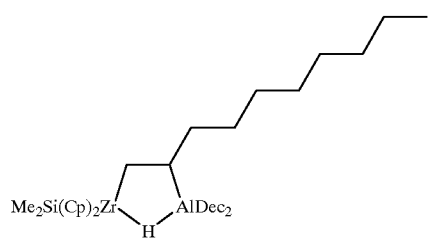
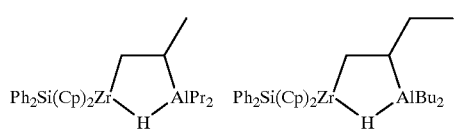
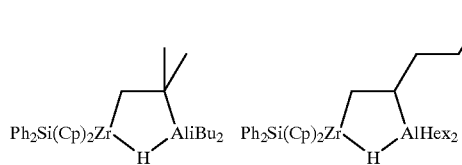
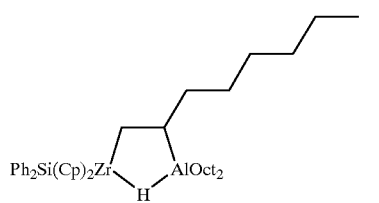
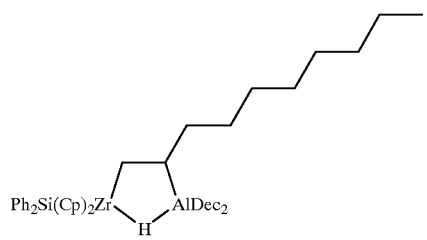
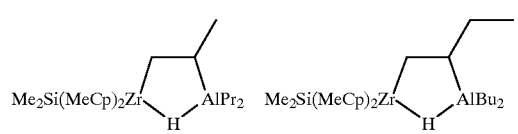
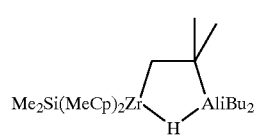
-continued
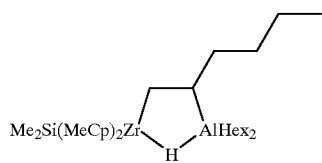
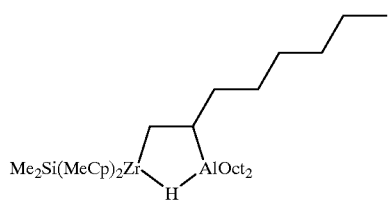
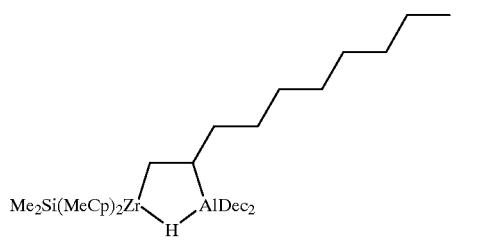
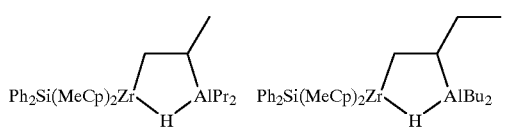
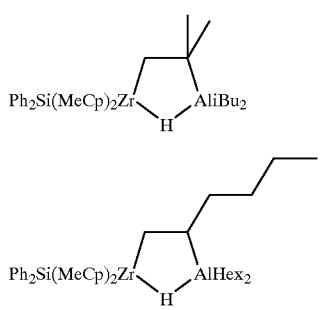
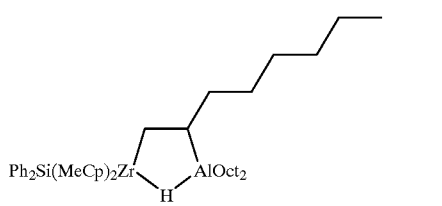
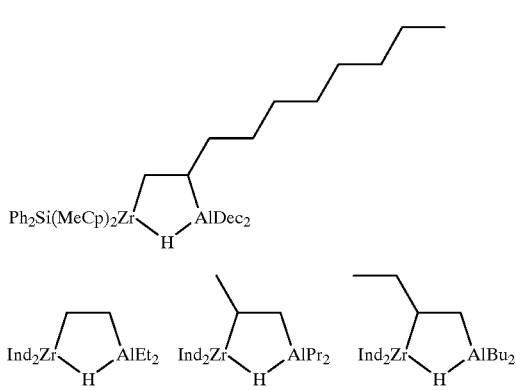

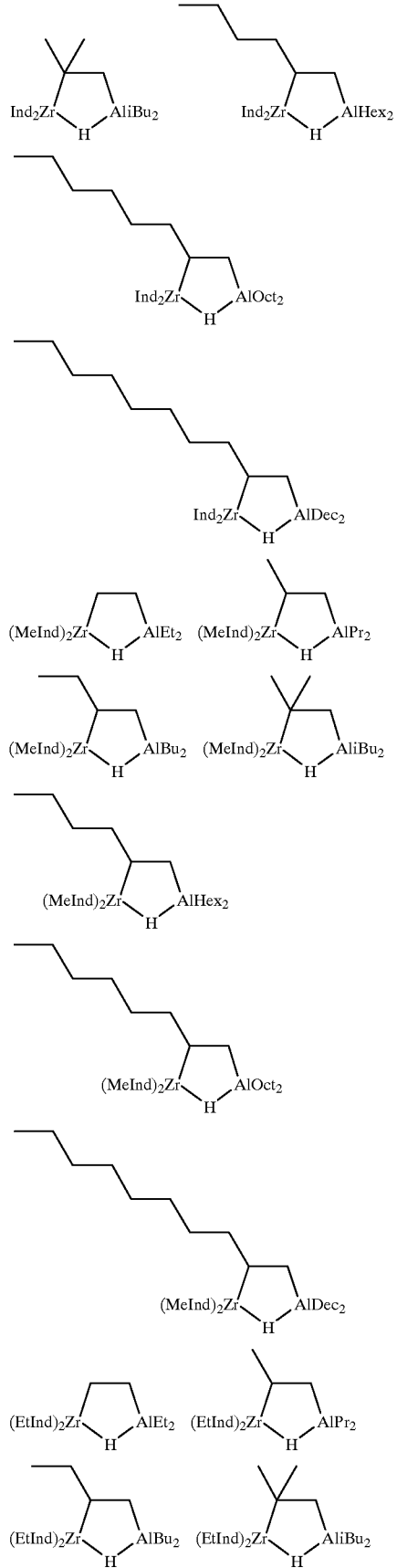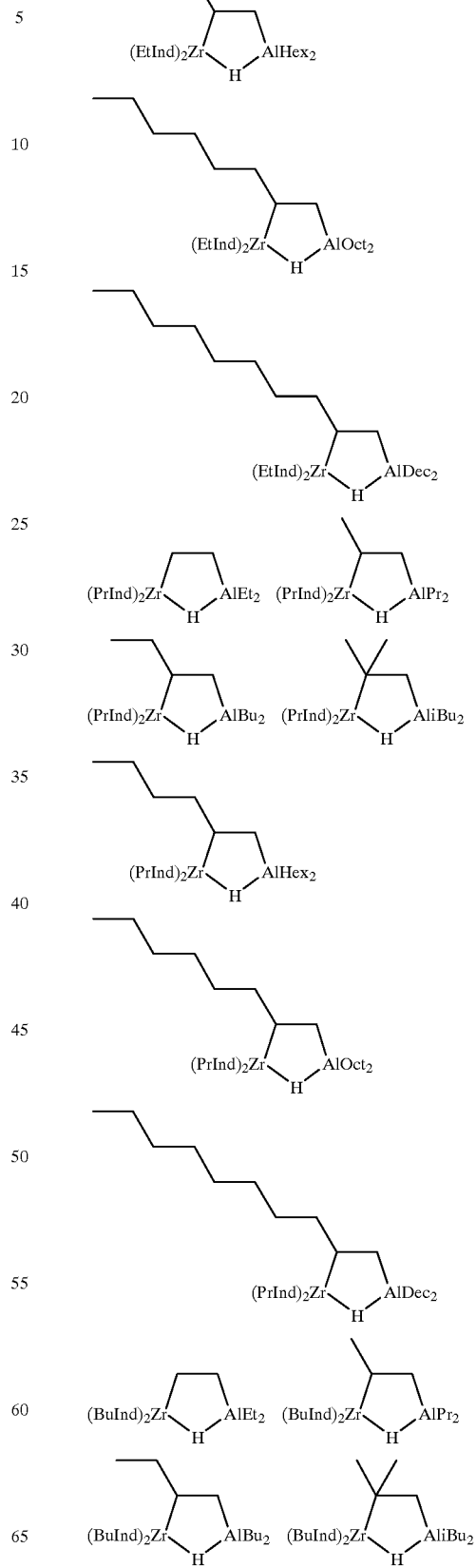

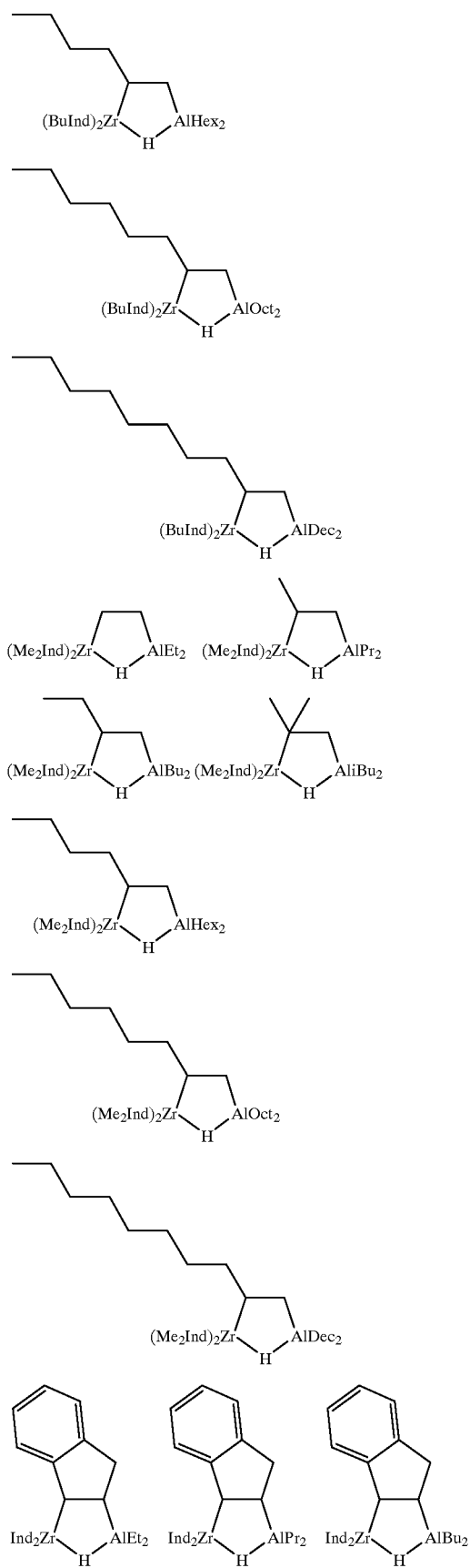
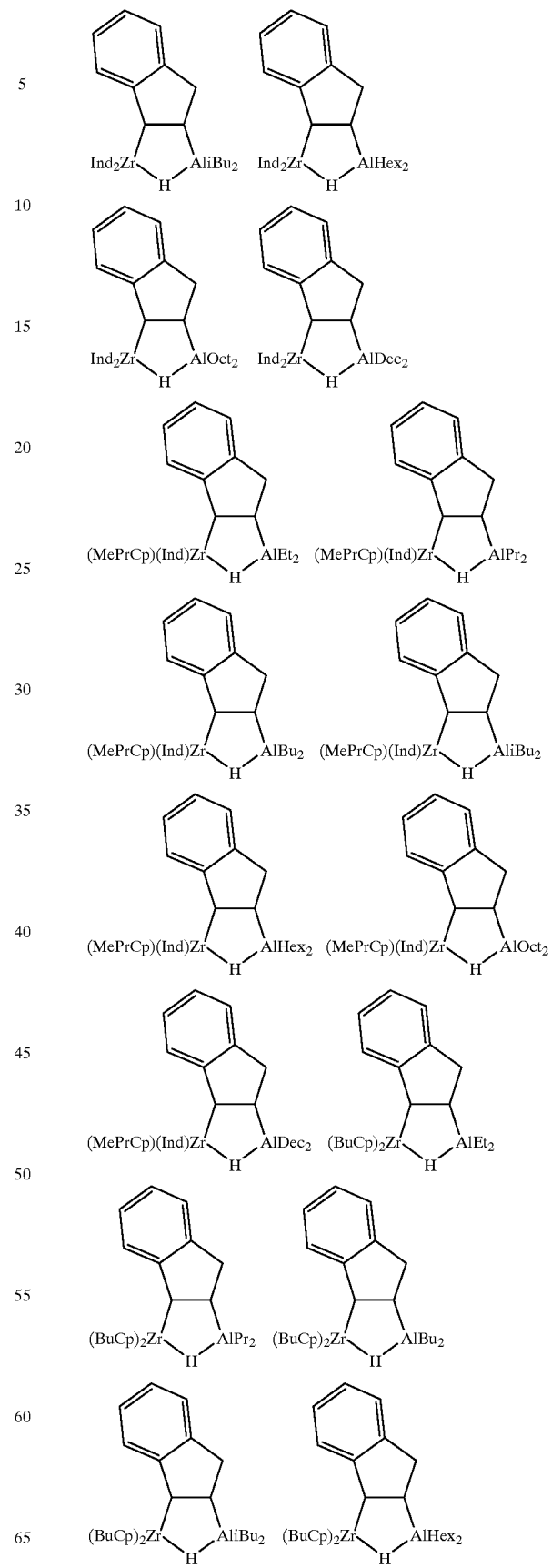

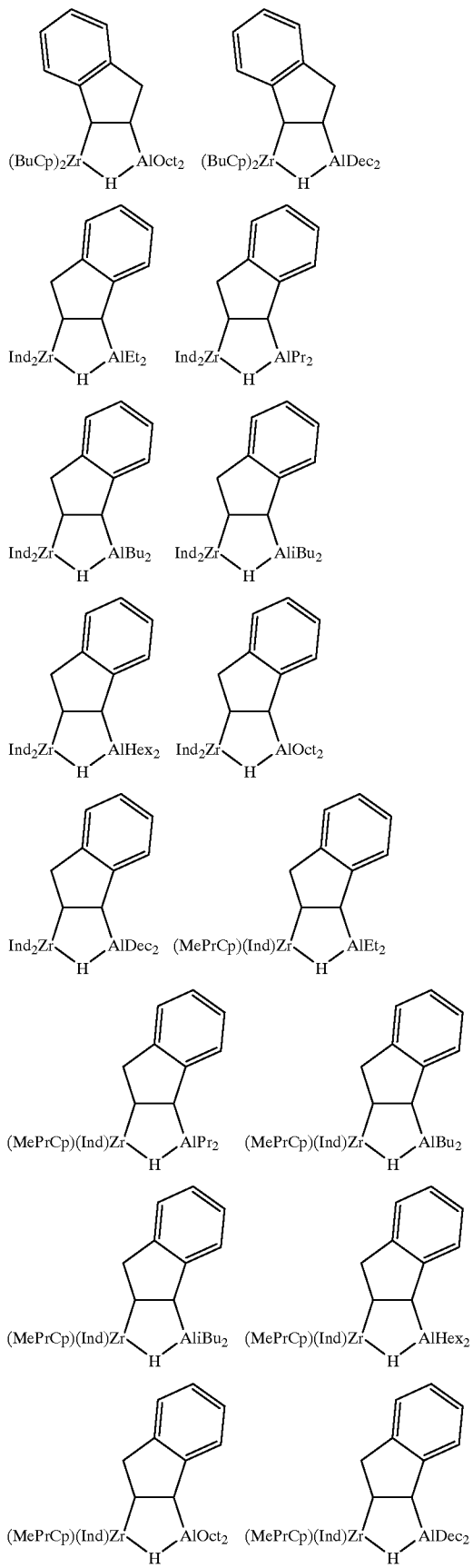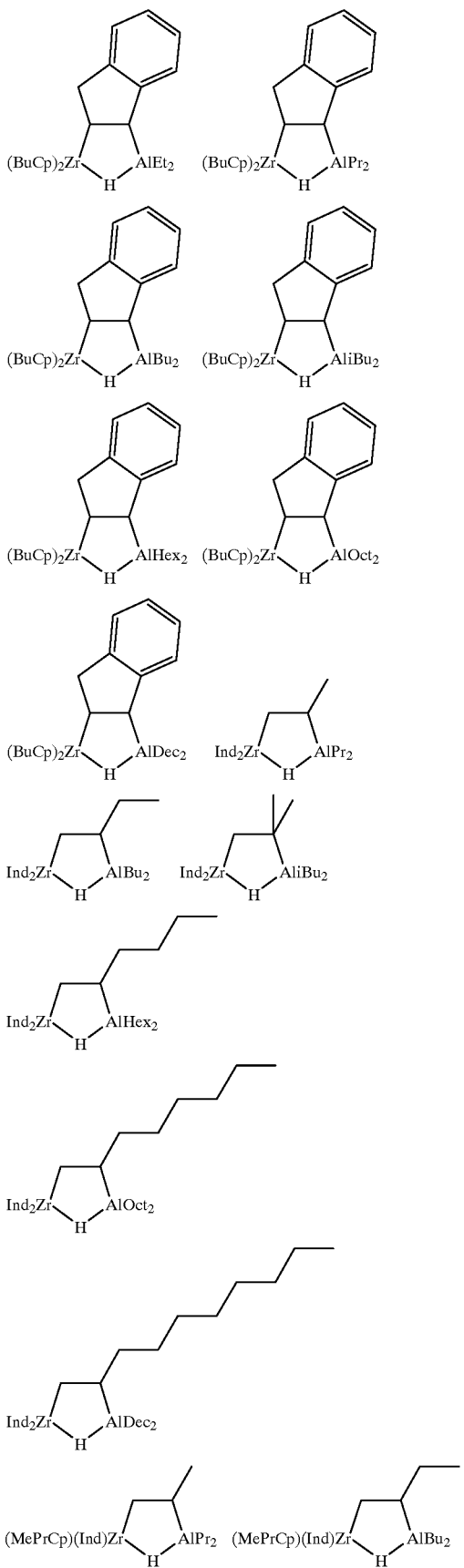

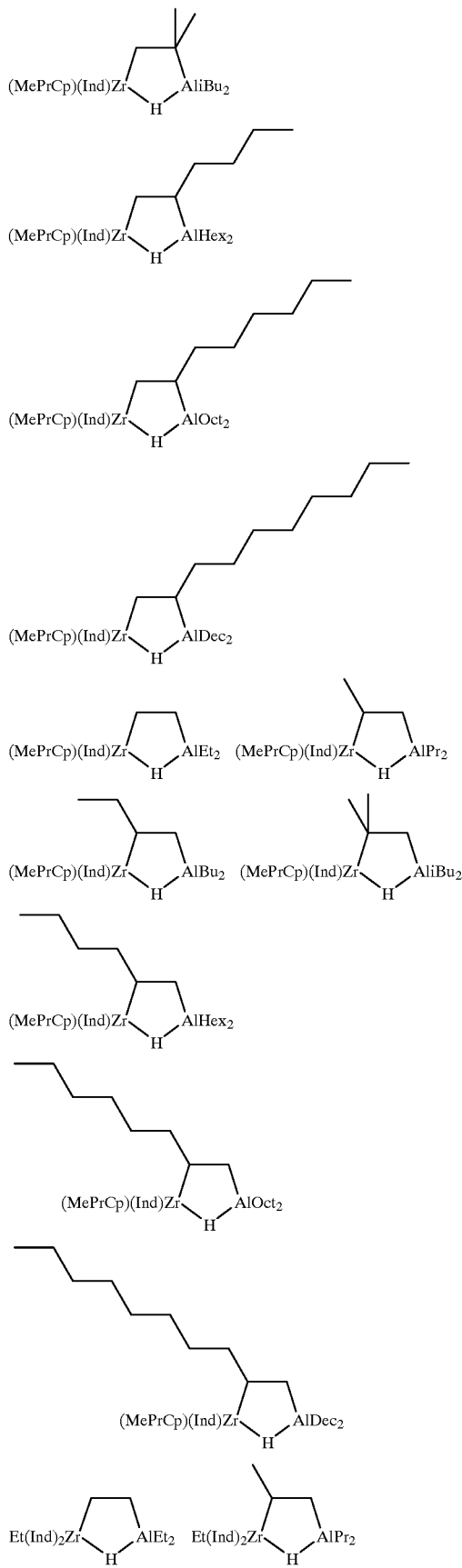
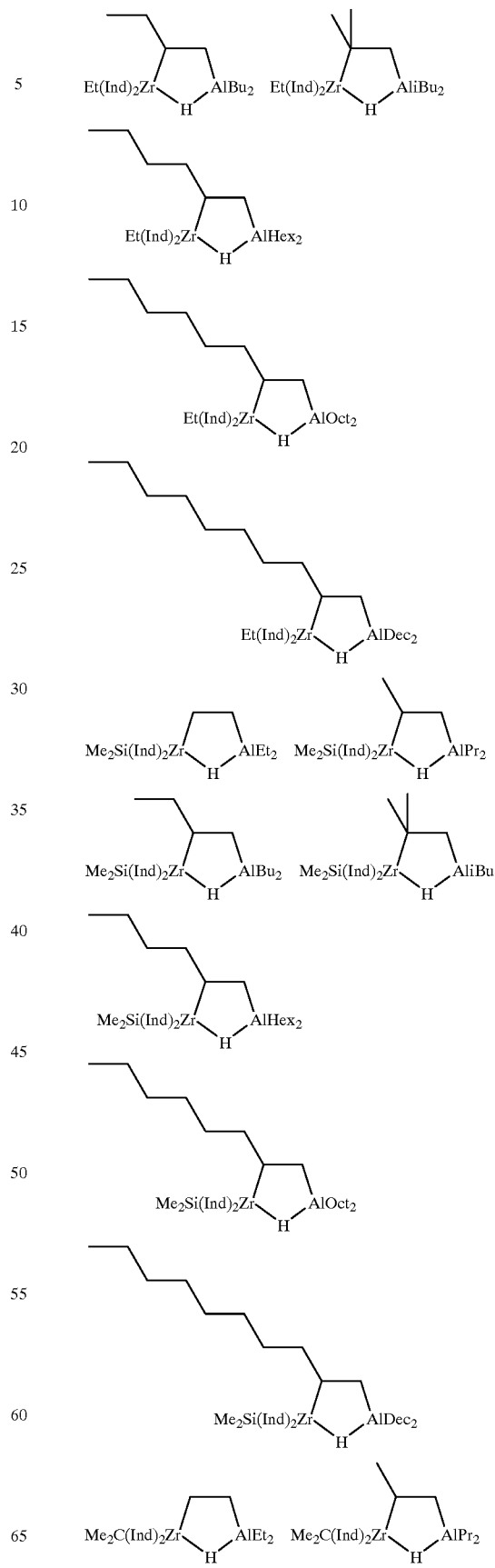

-continued
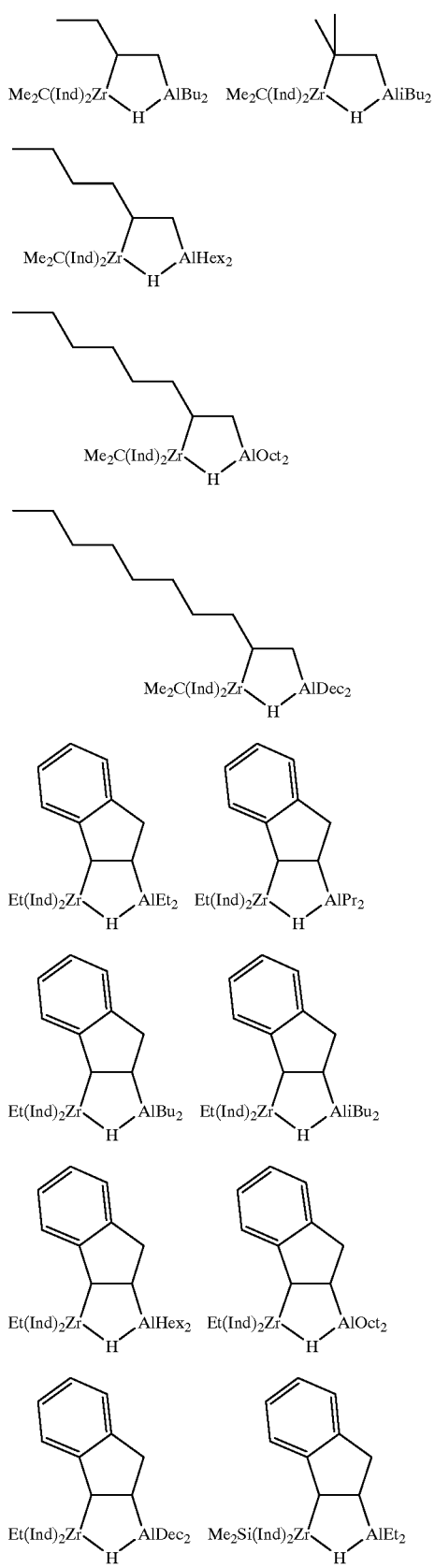
-continued
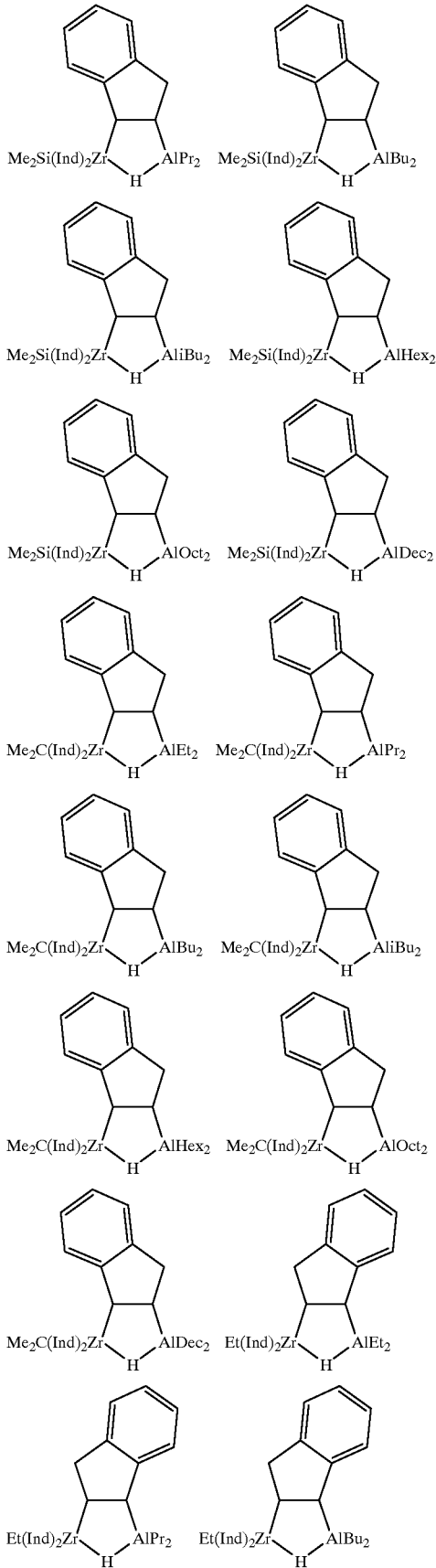

-continued
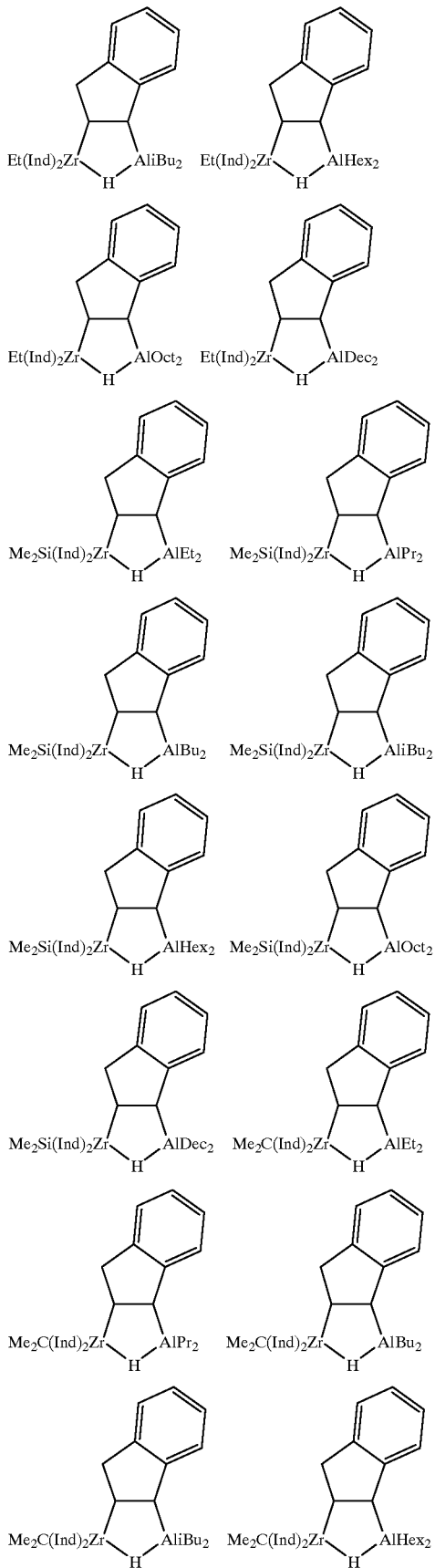
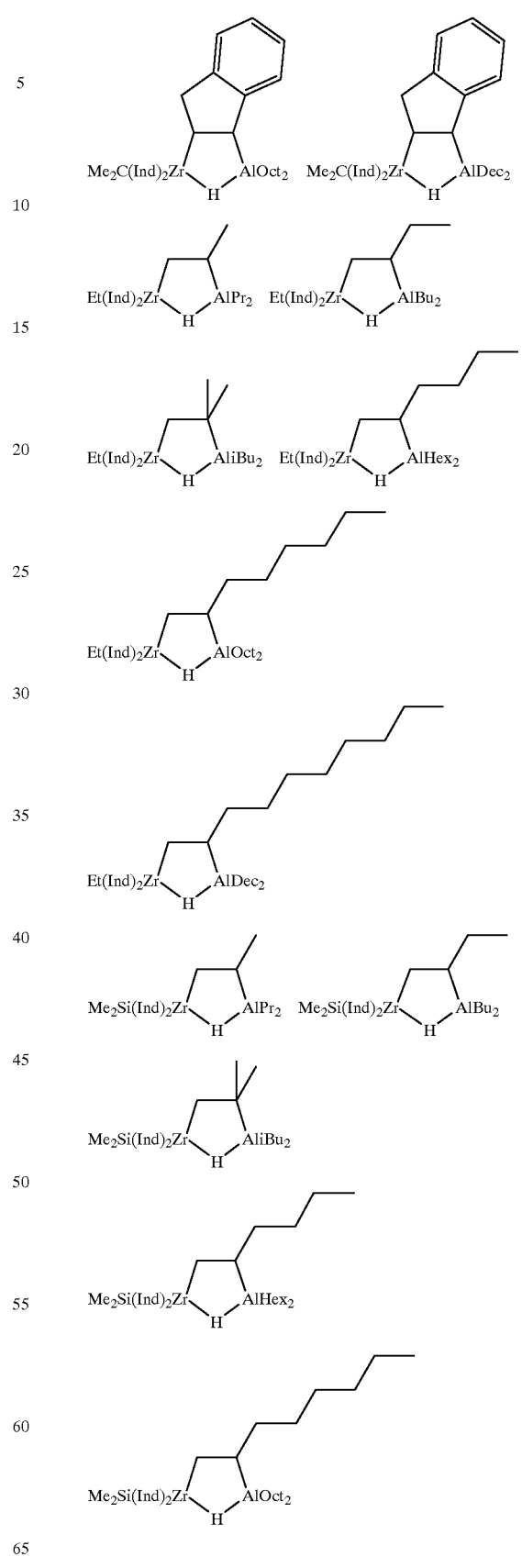

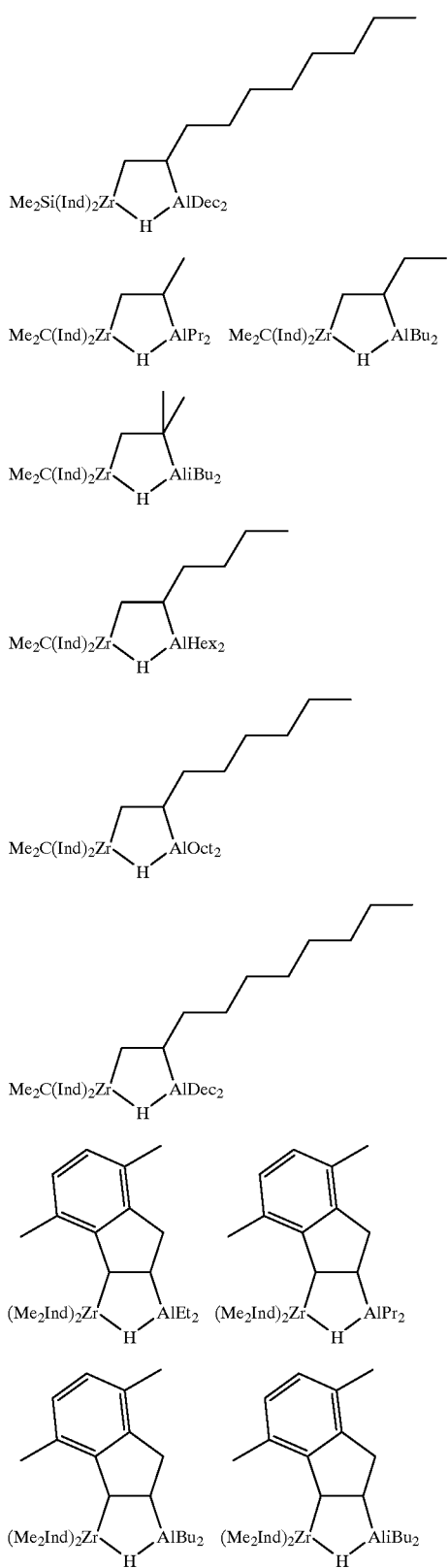
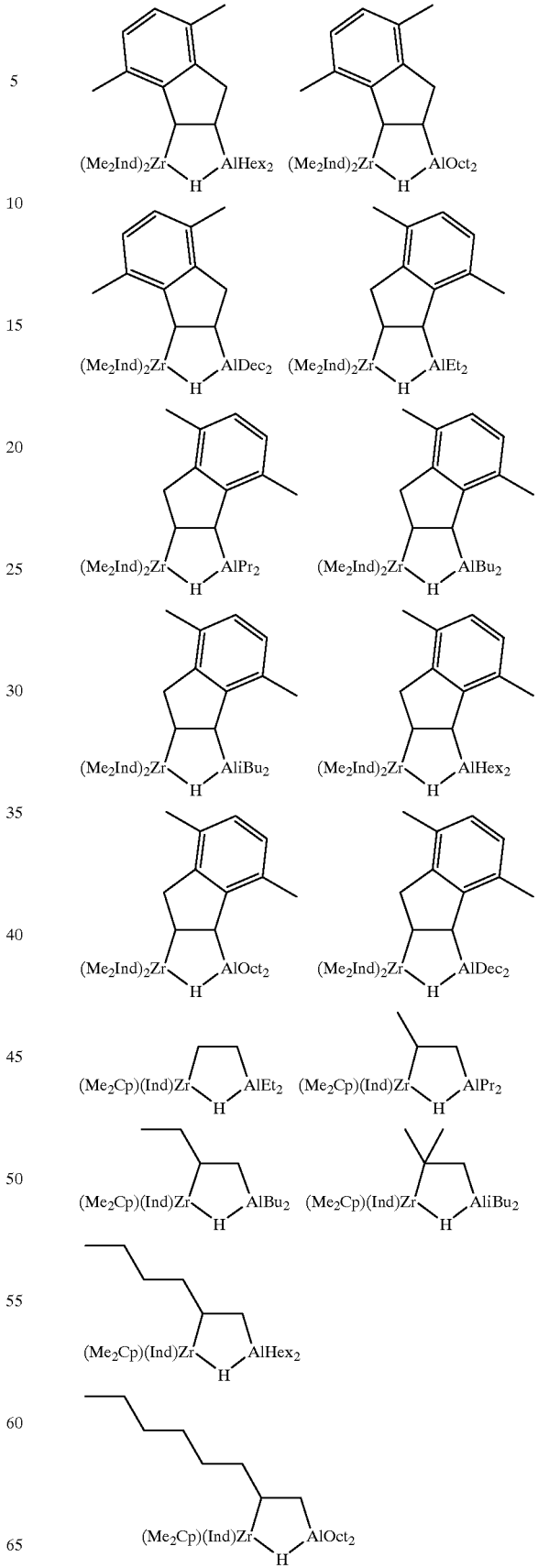

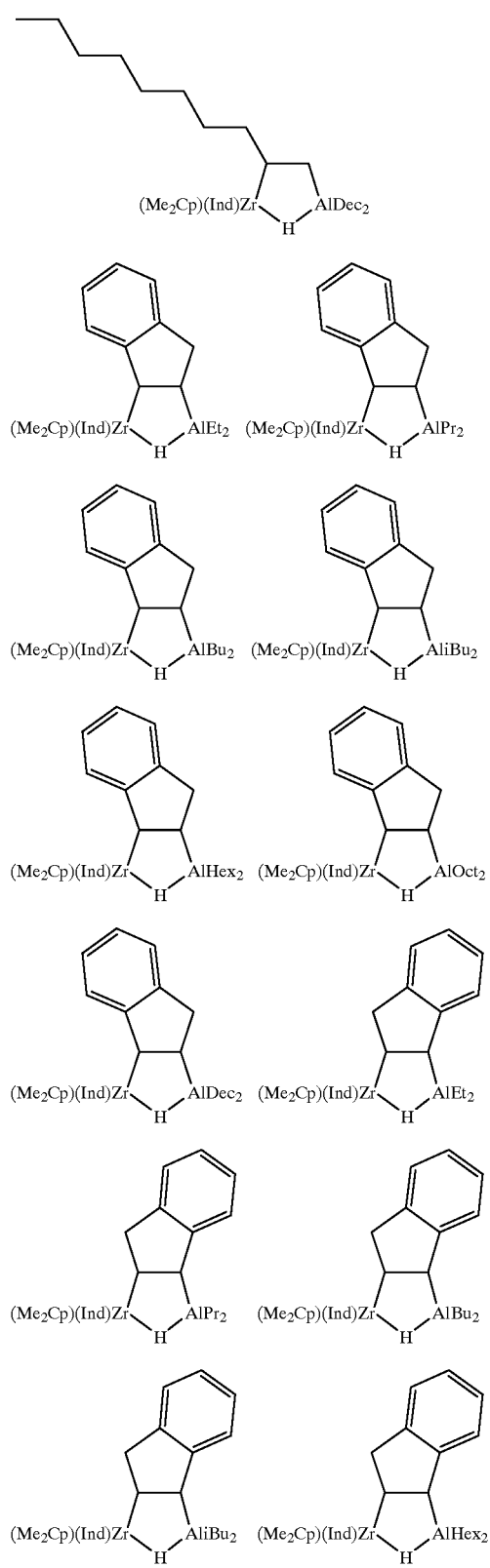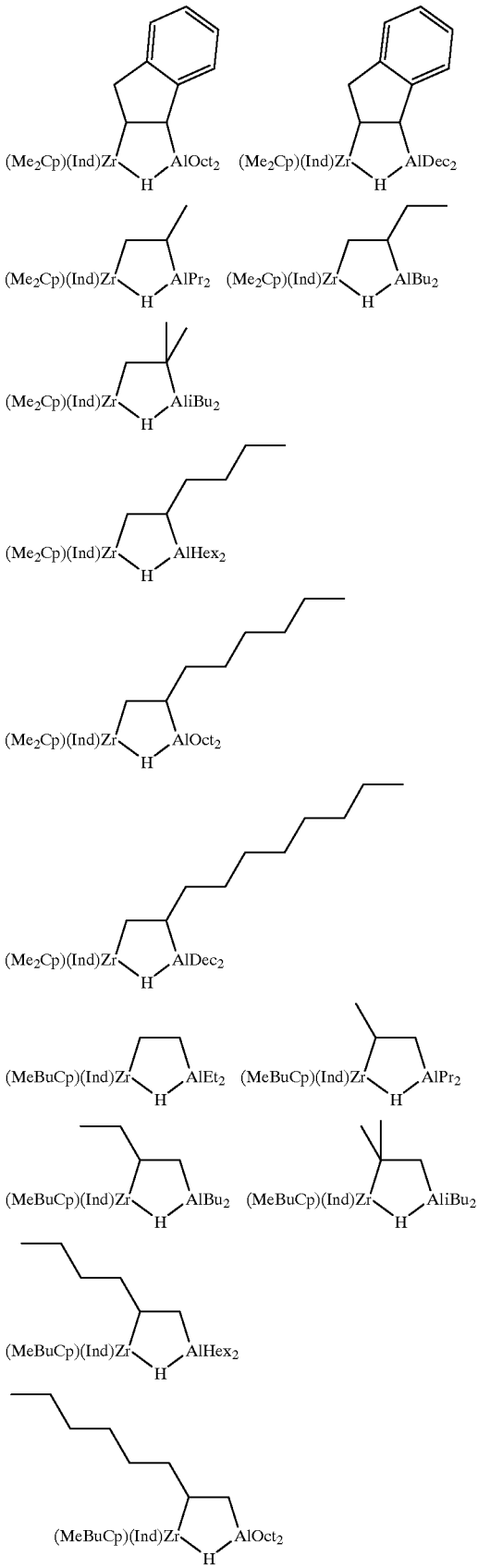

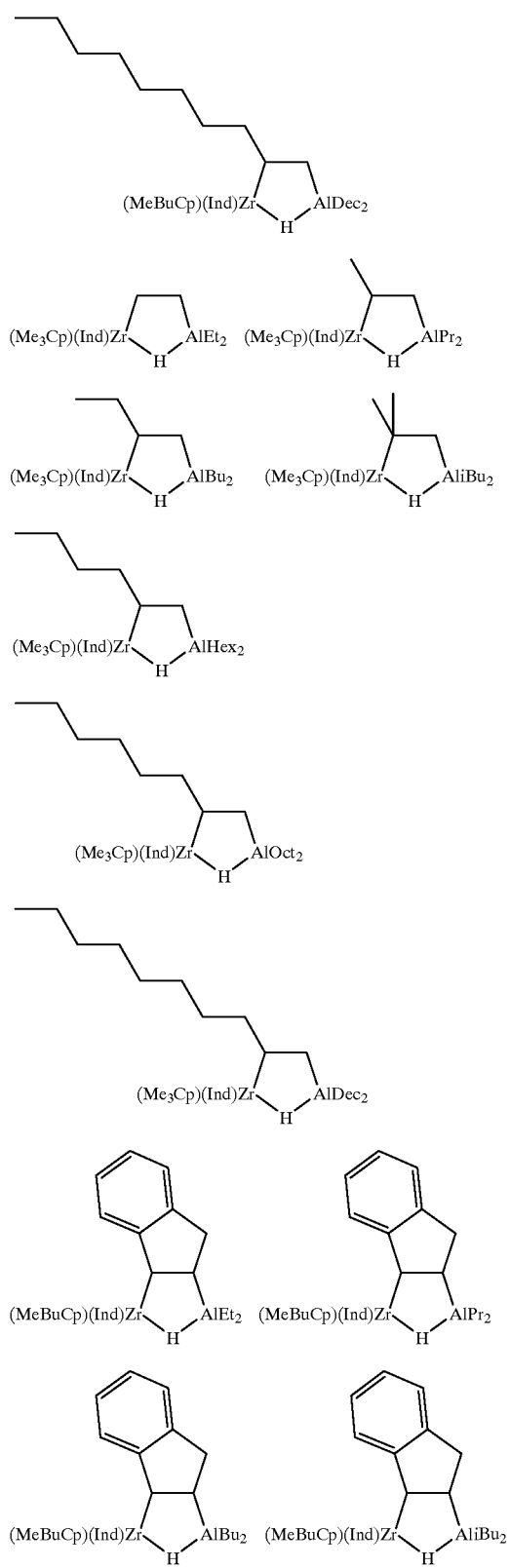
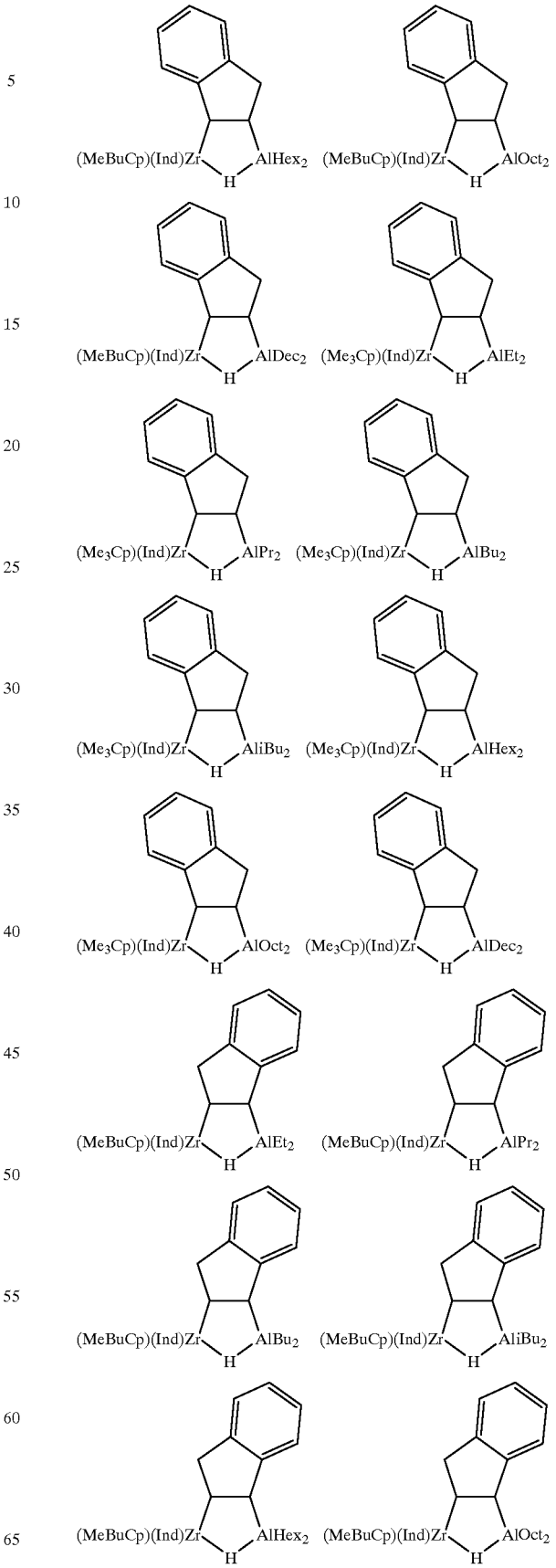

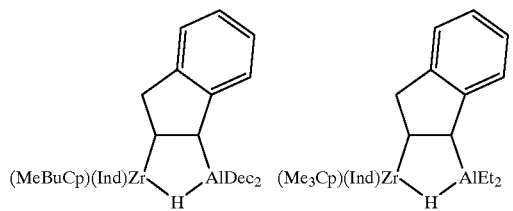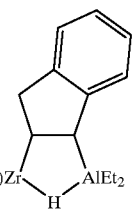
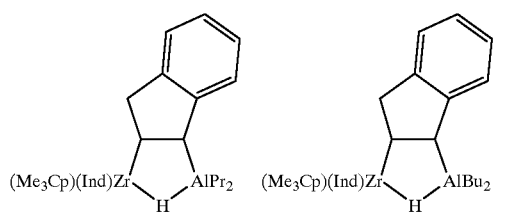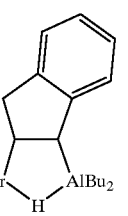
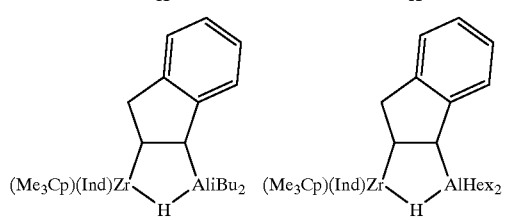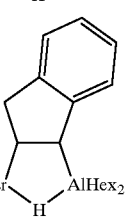
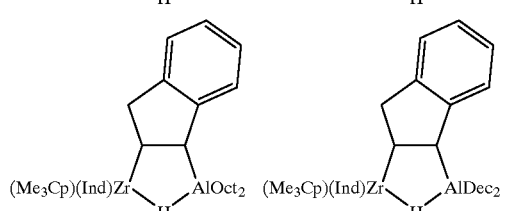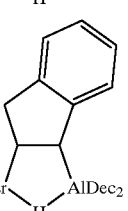
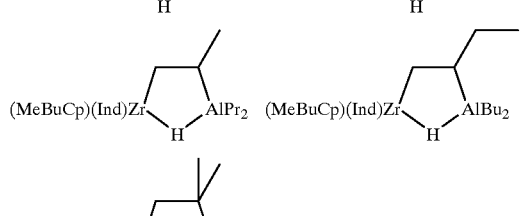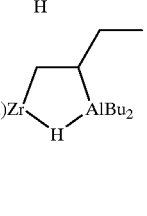
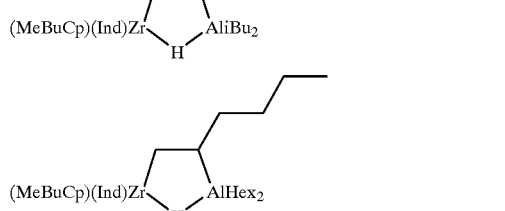
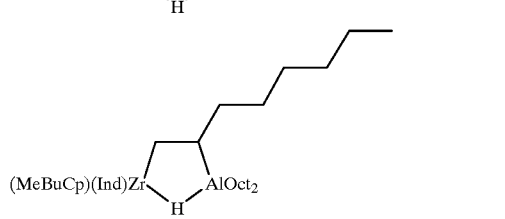
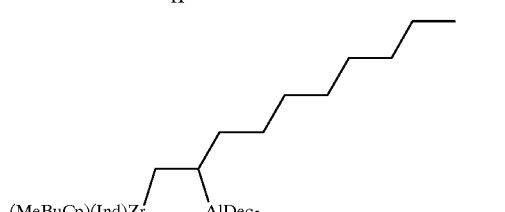
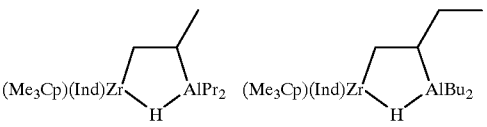
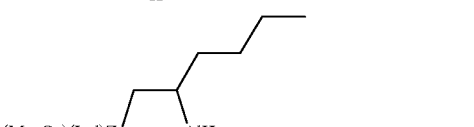
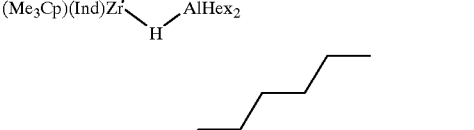
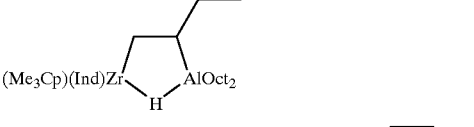
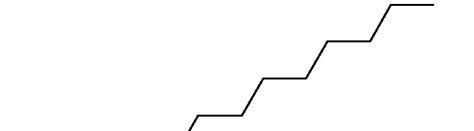
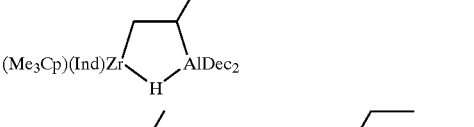
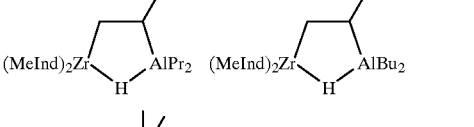
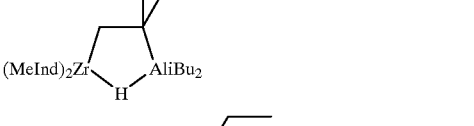
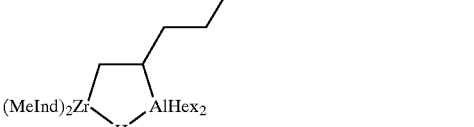
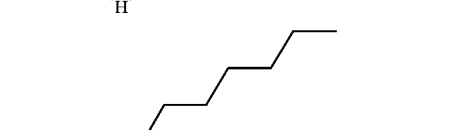
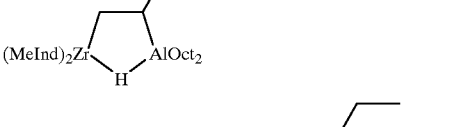
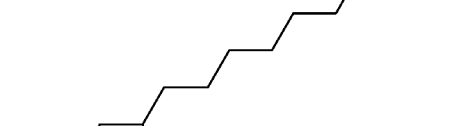
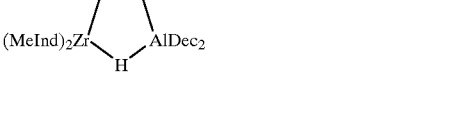

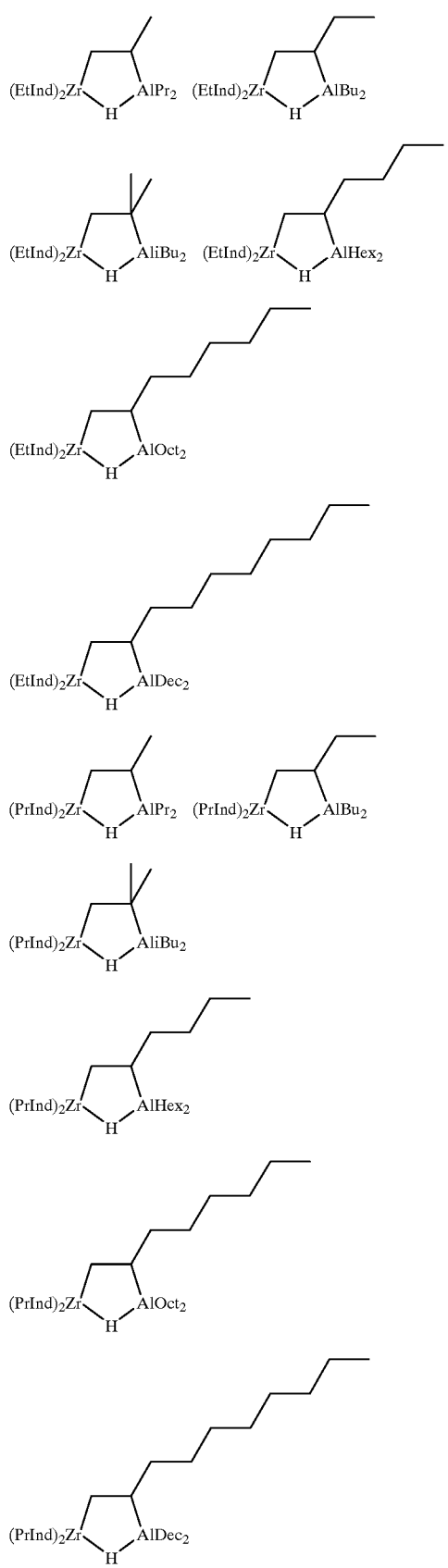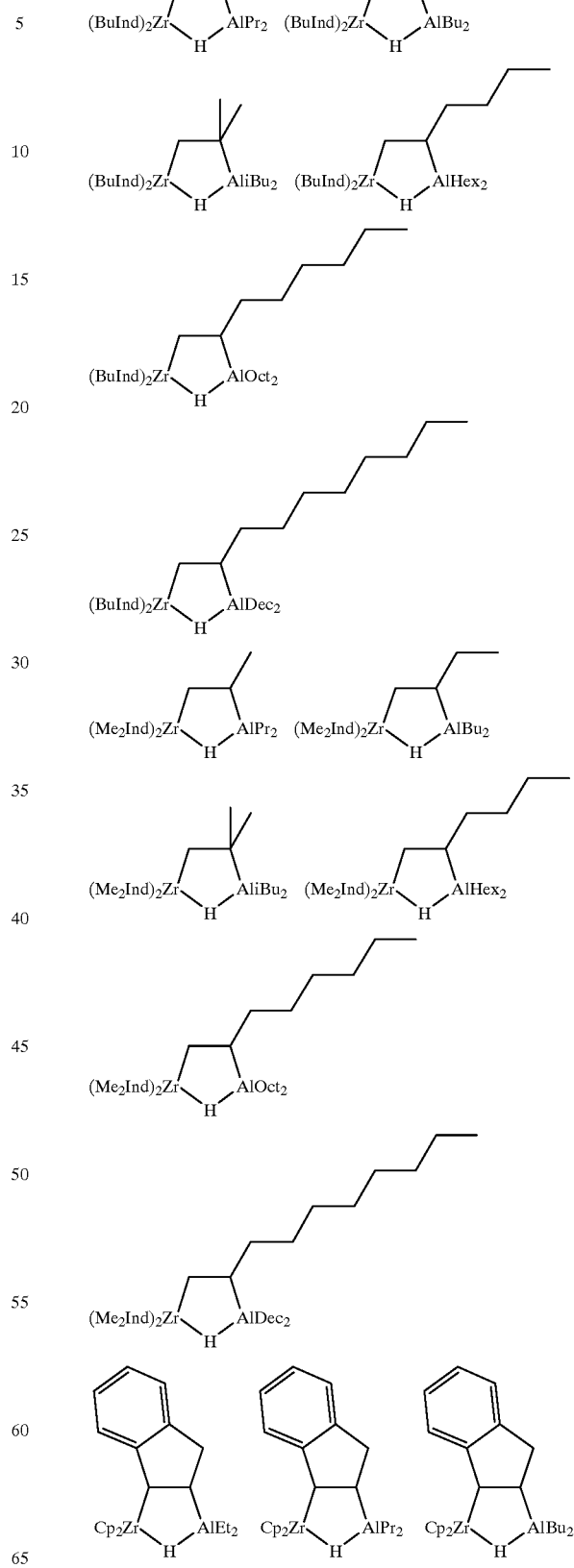

-continued
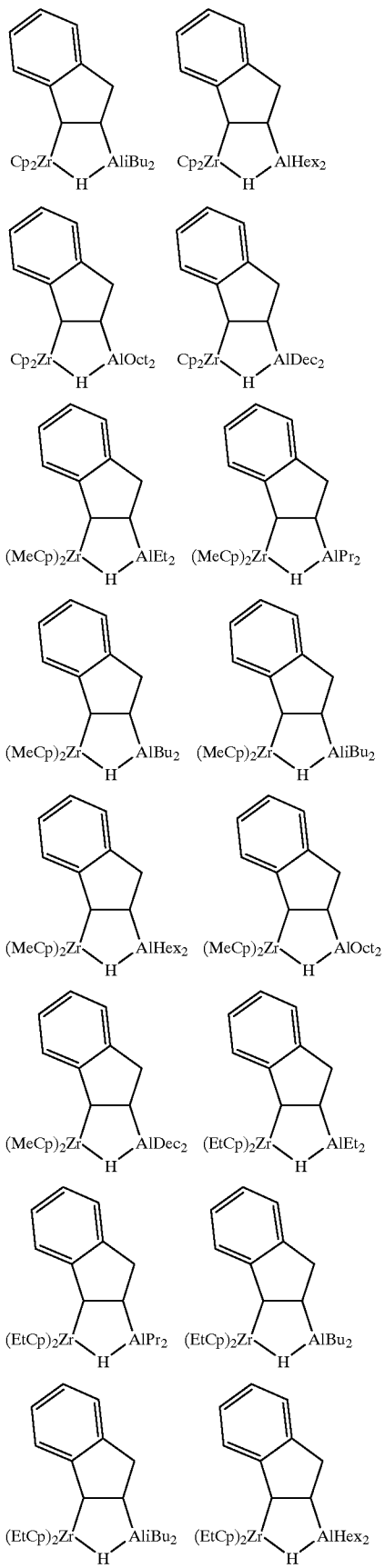
-continued
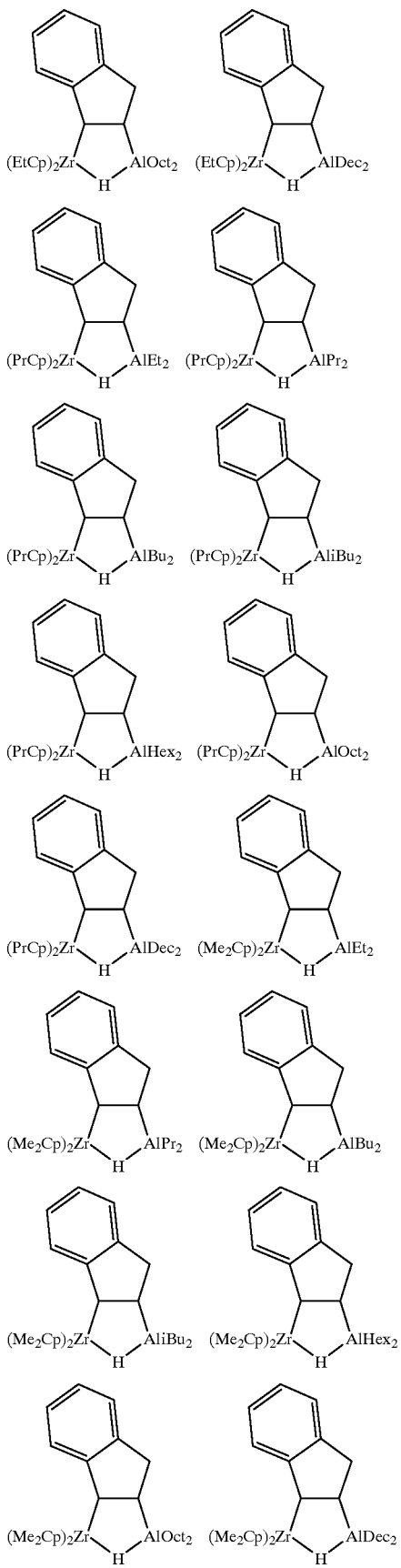

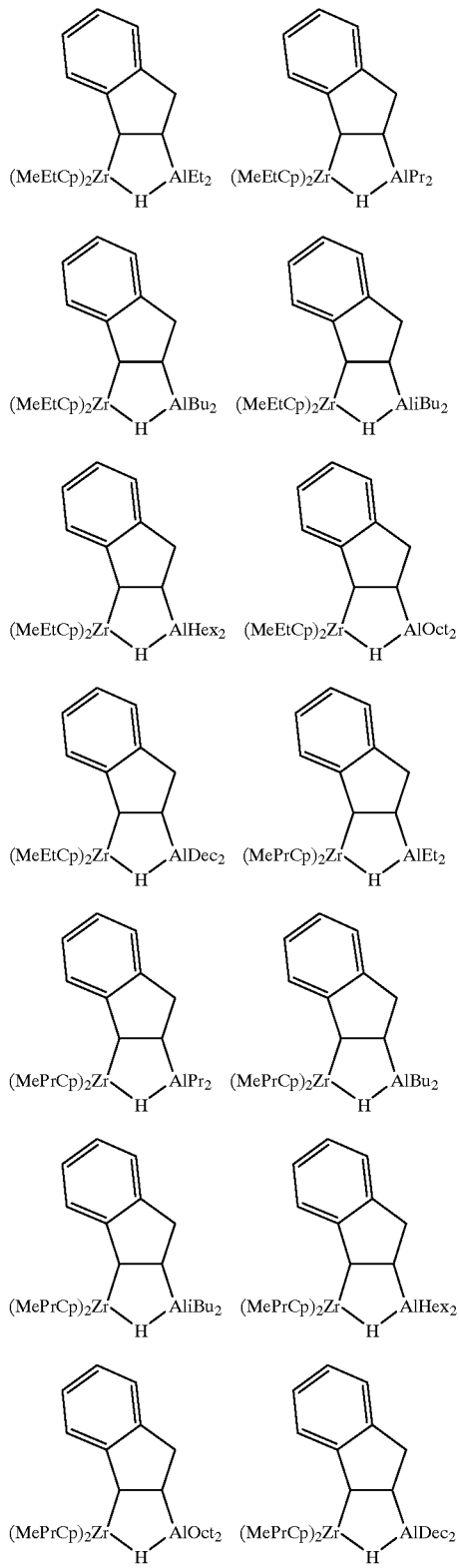
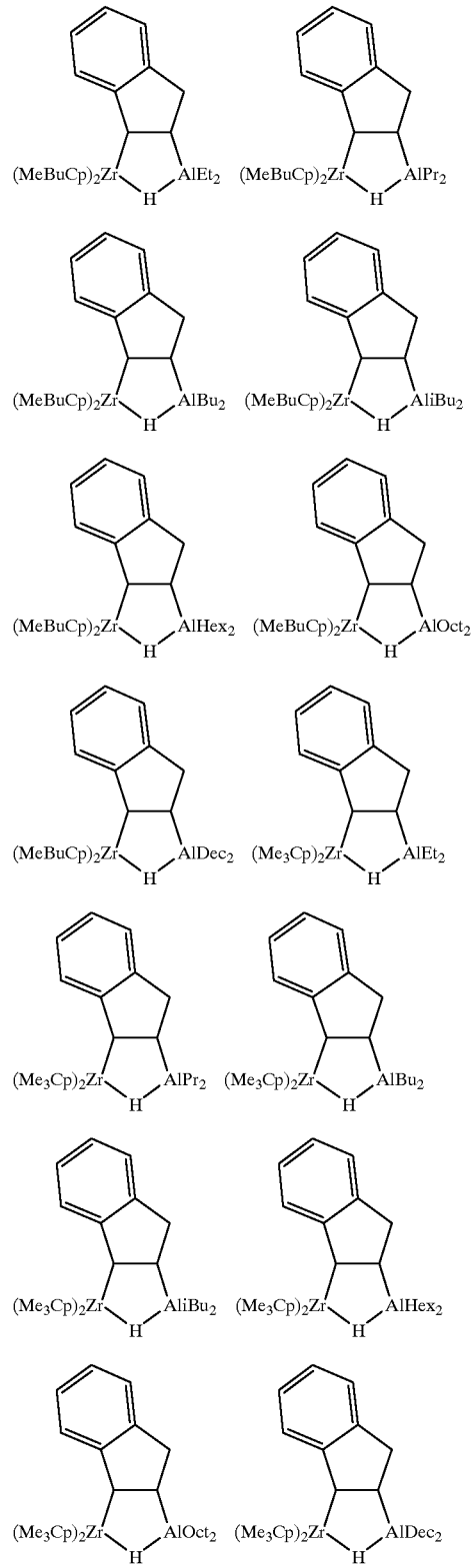

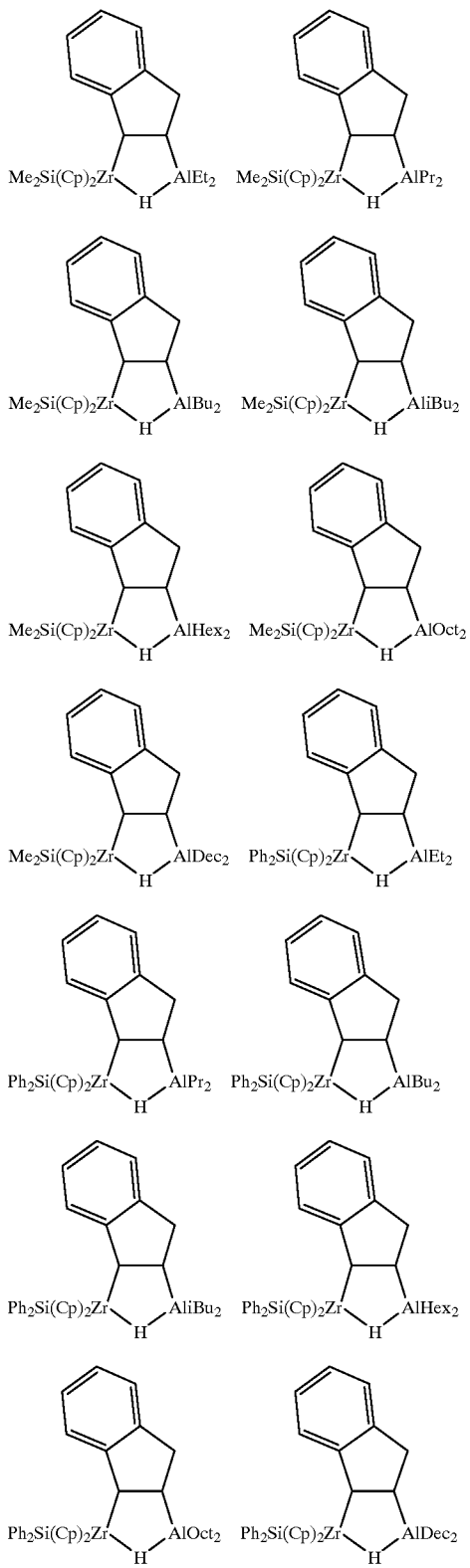
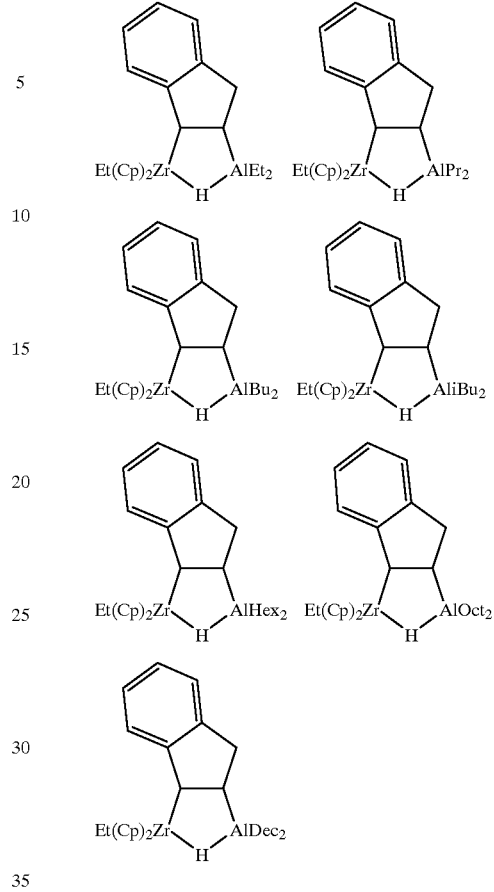
Among the above exemplified compounds, particularly preferred for use as a component for polymerization of olefins are as follows
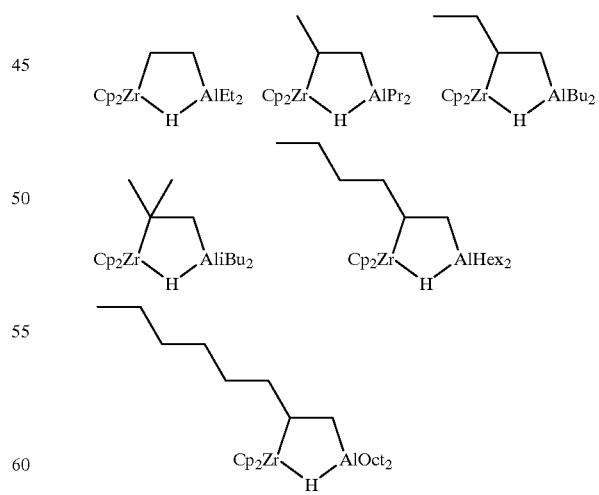

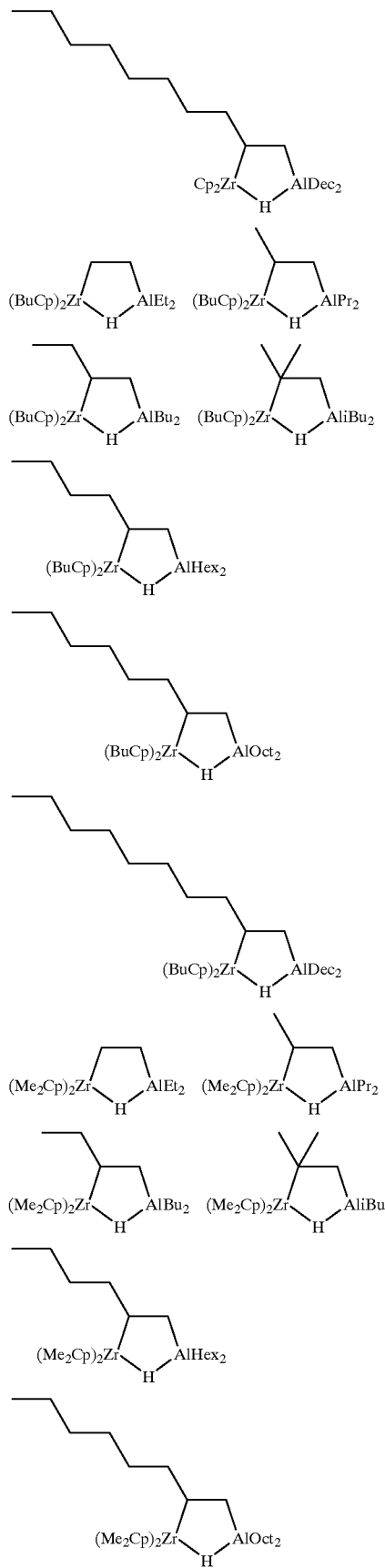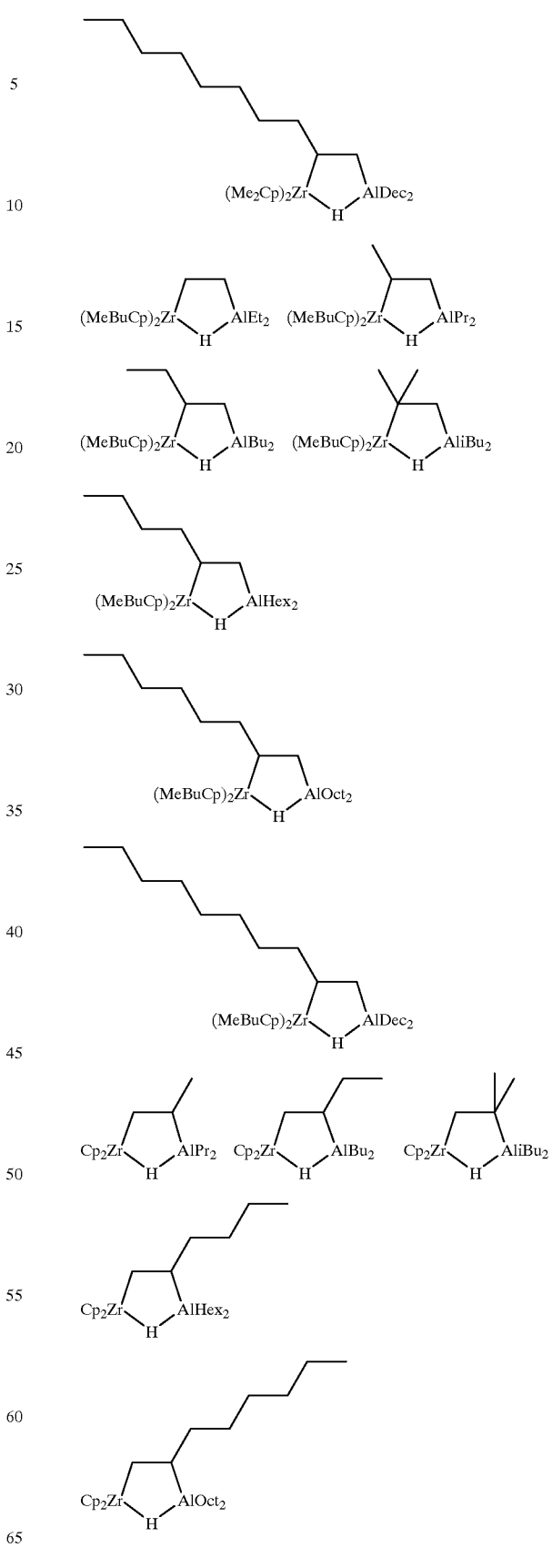

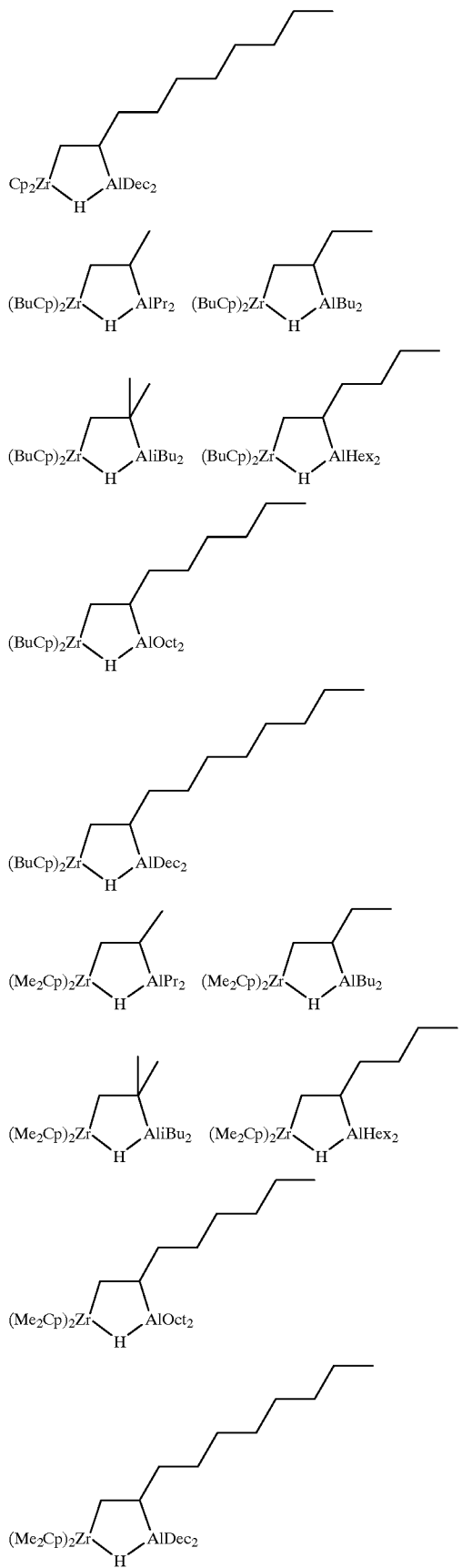
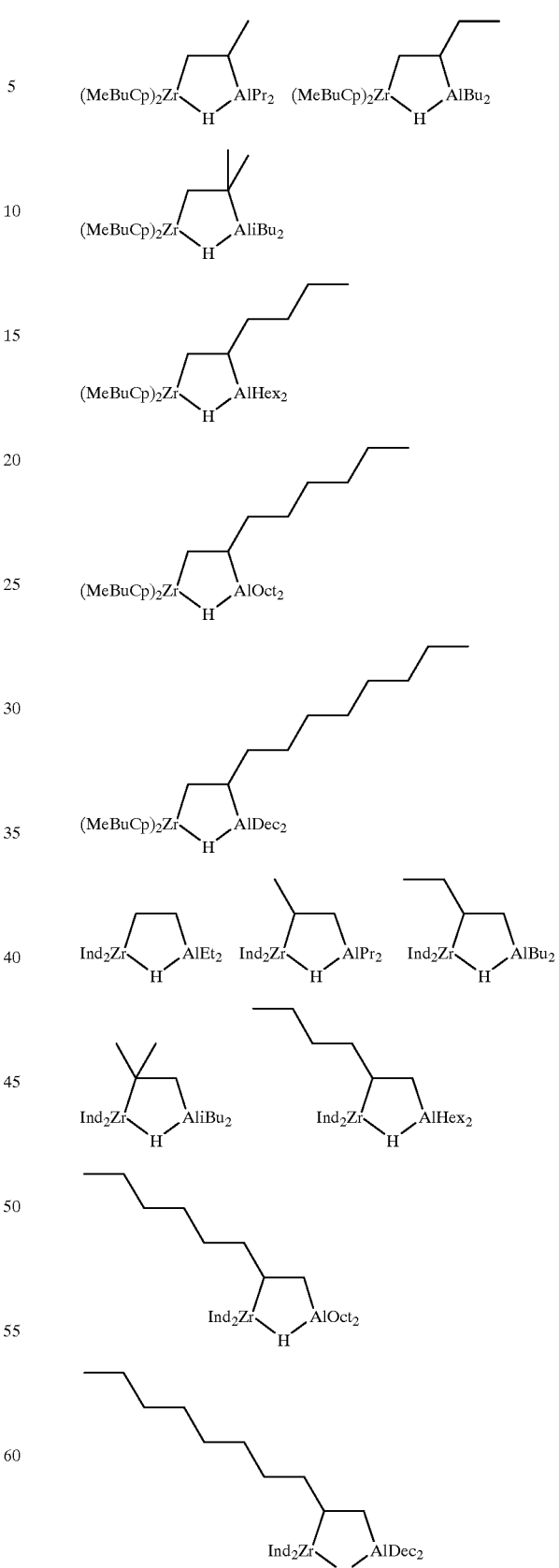

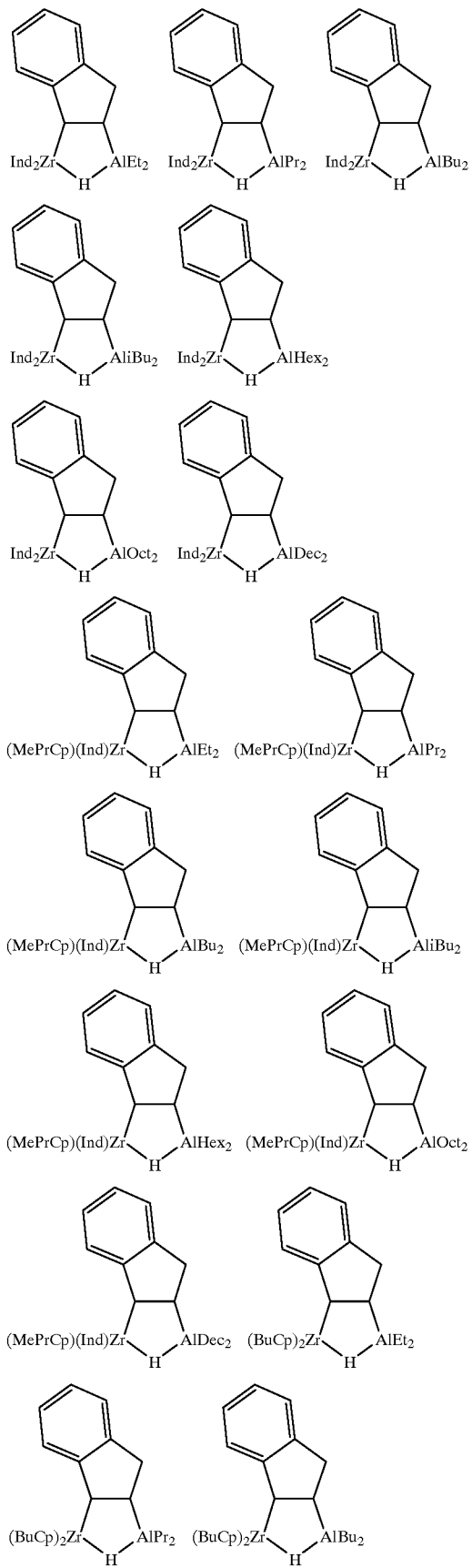
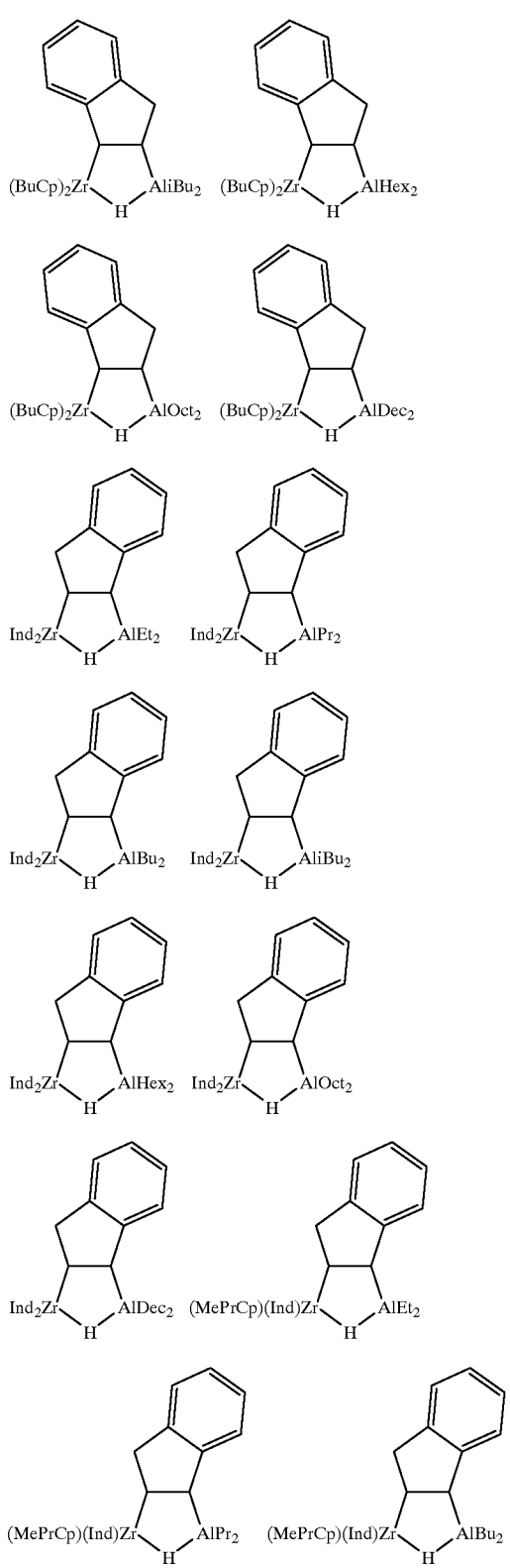

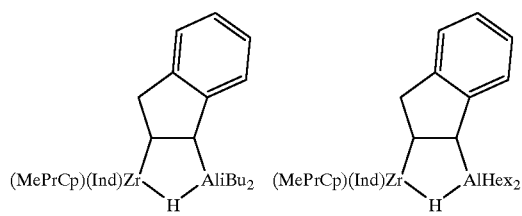
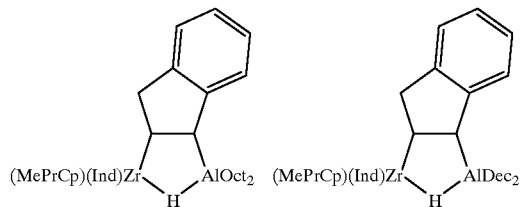
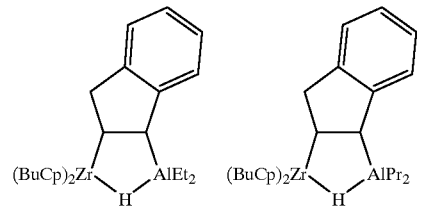
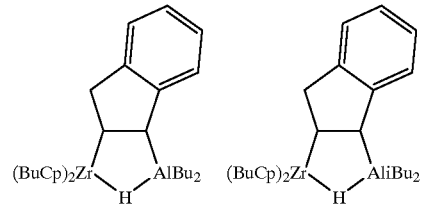
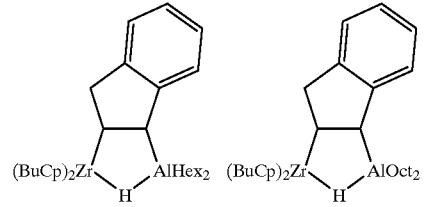
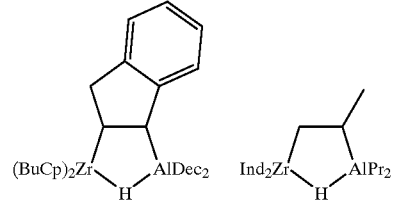
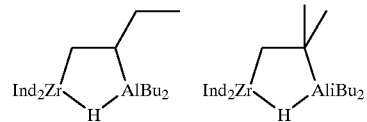
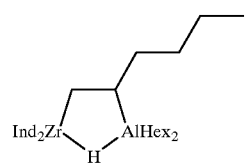
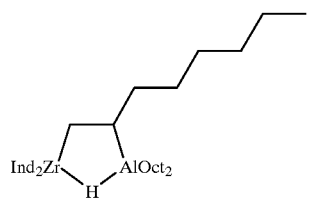
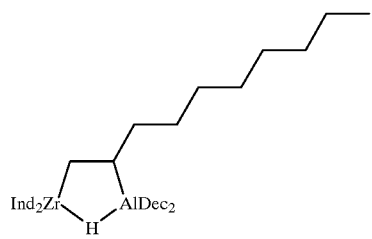
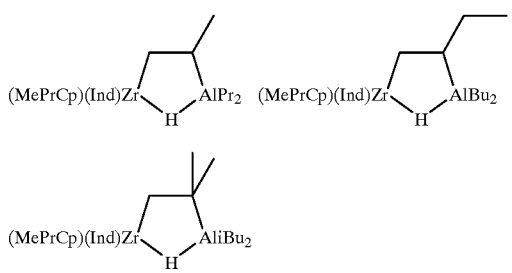
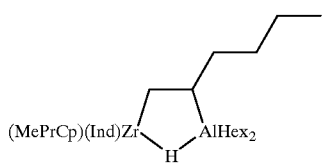
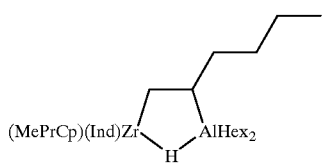
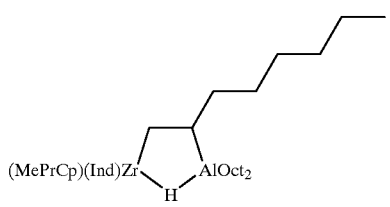
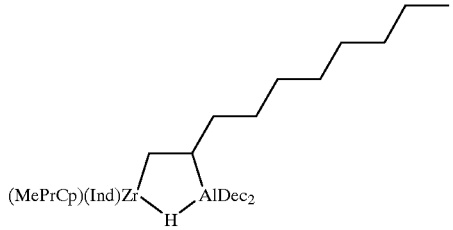
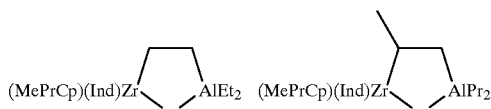
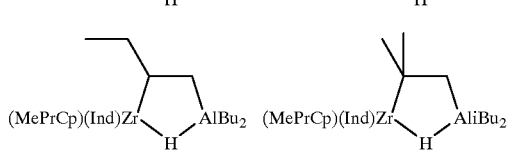

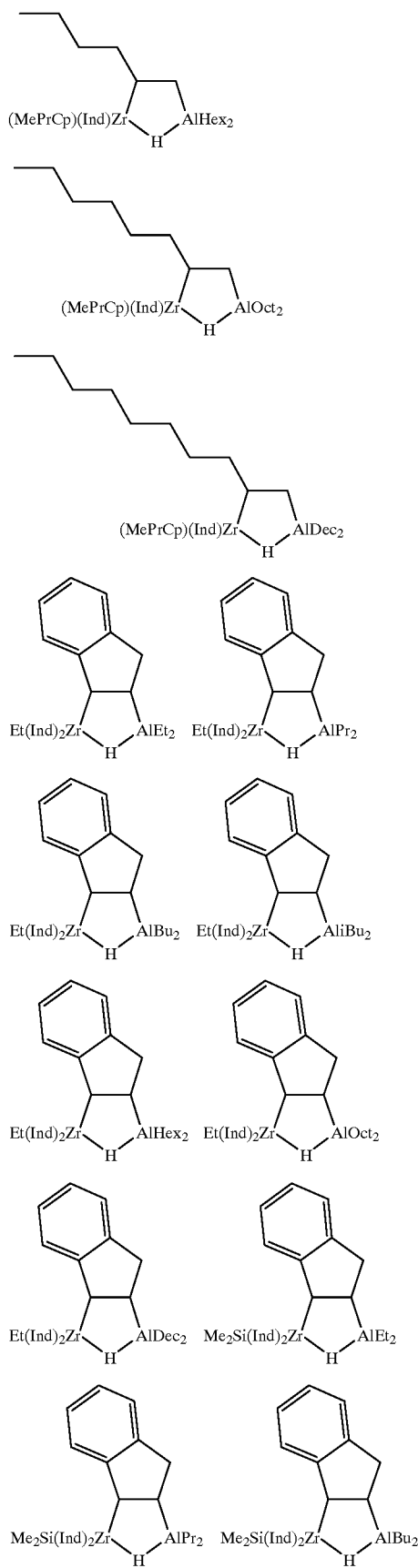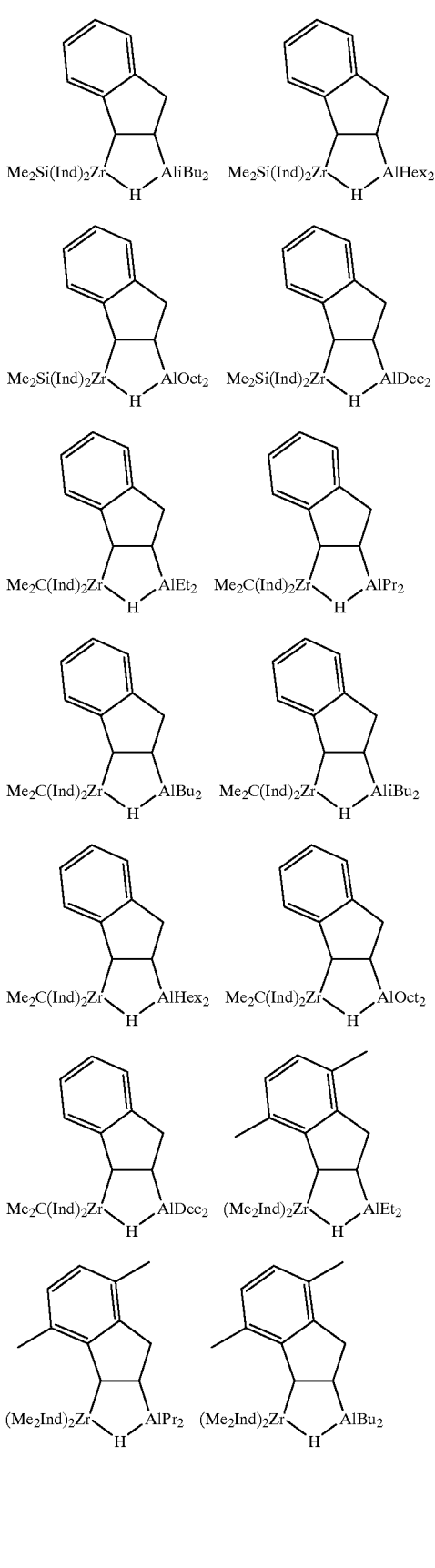

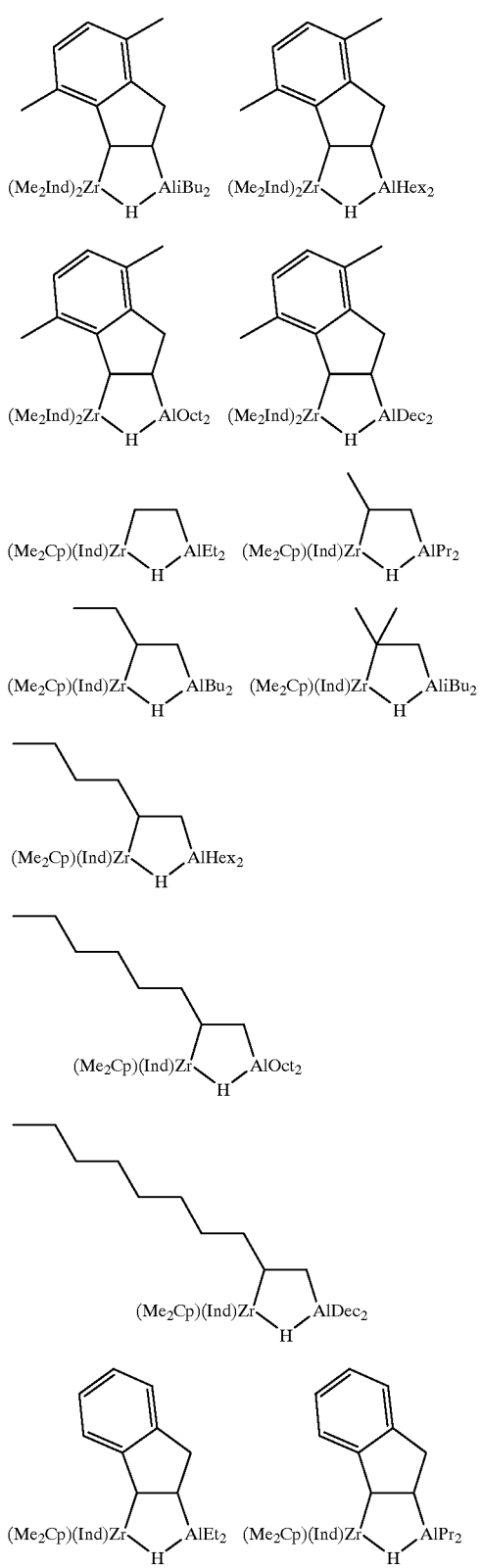
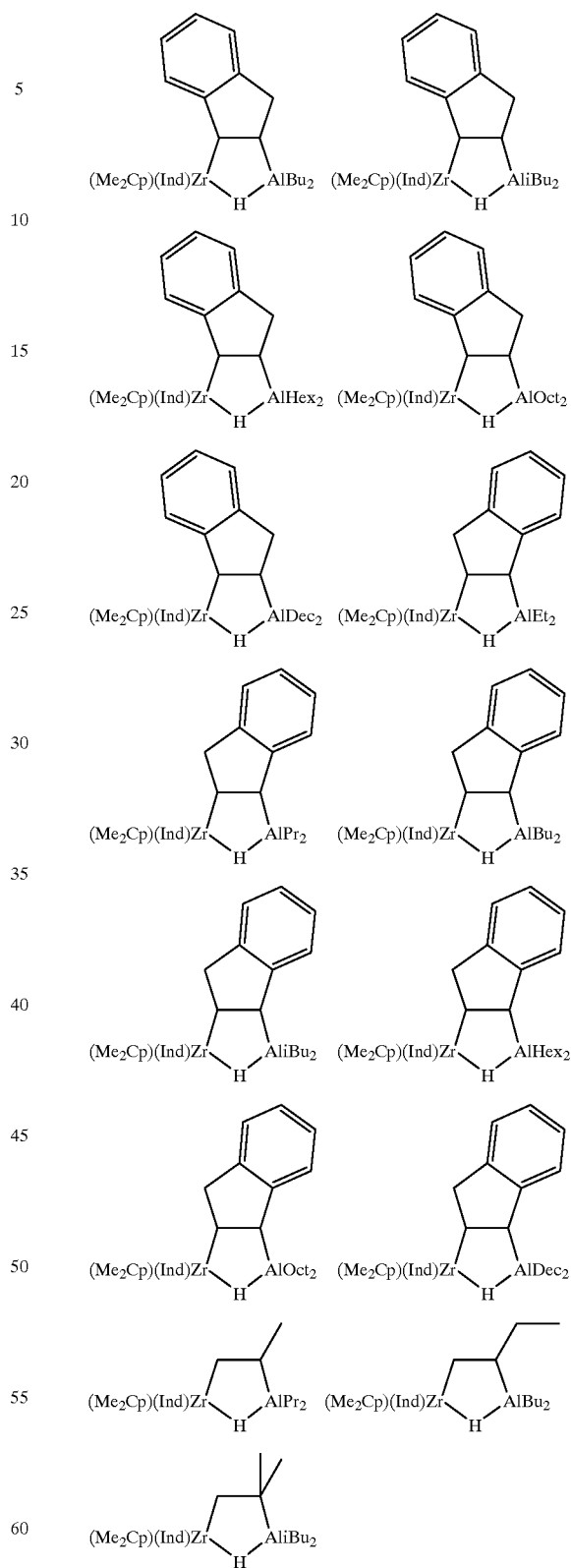

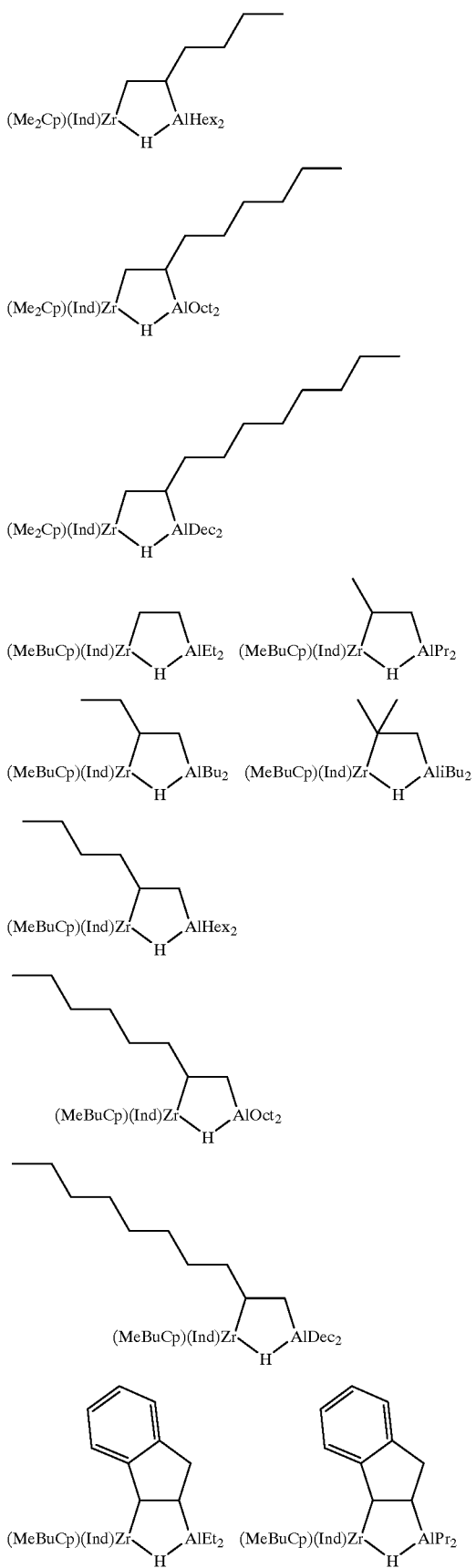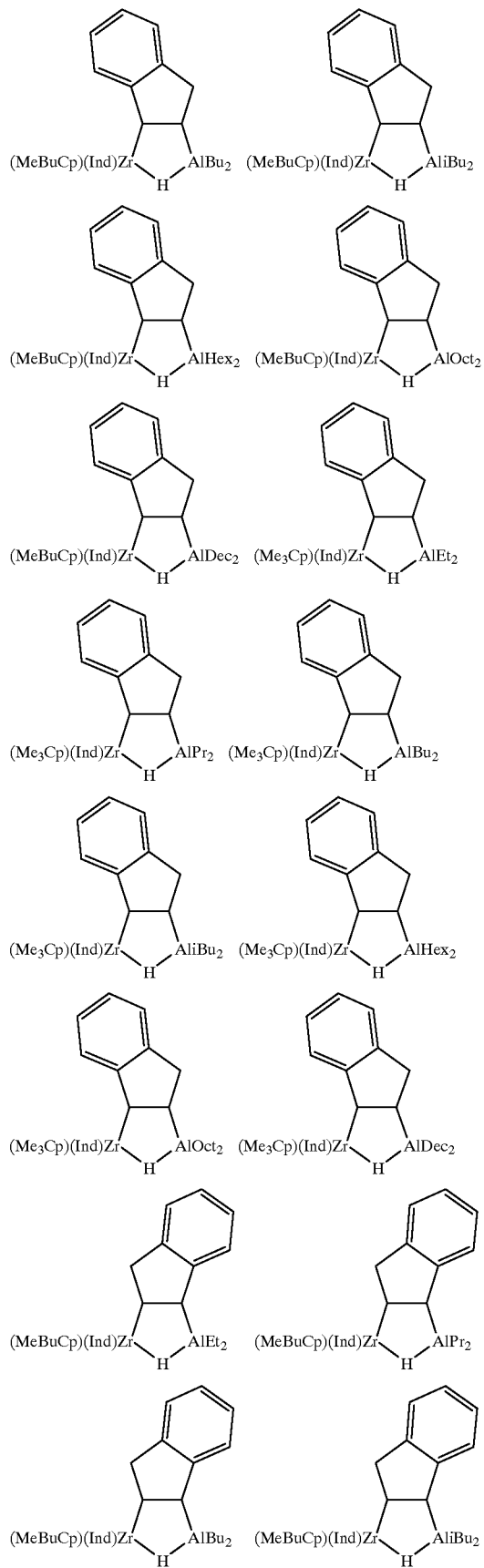

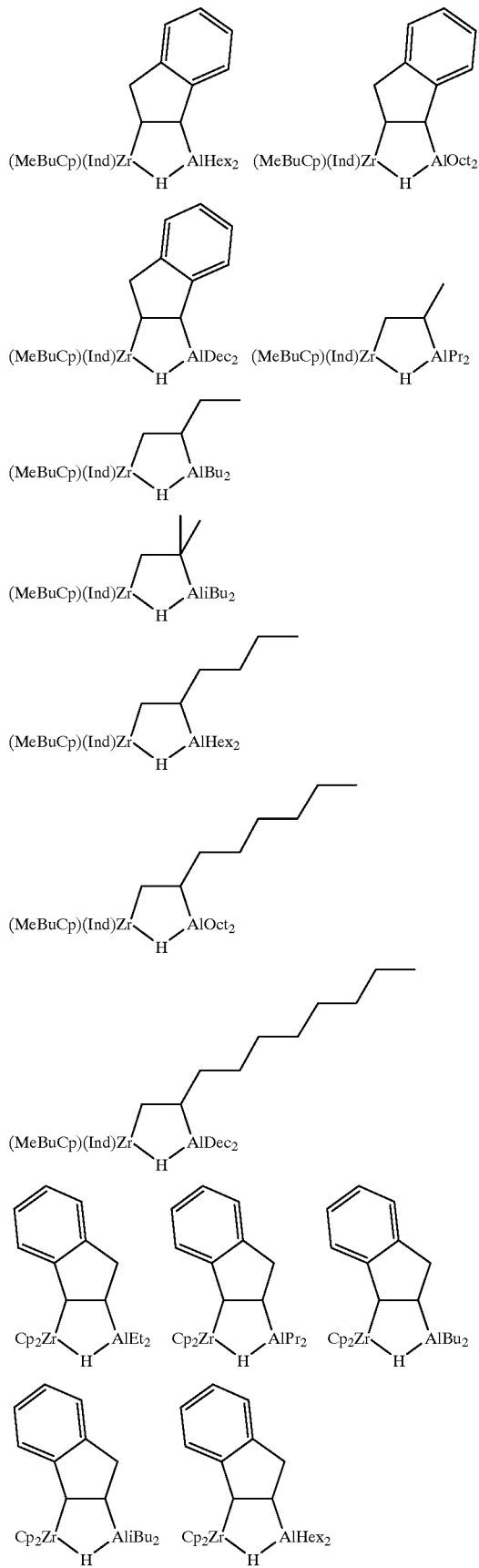
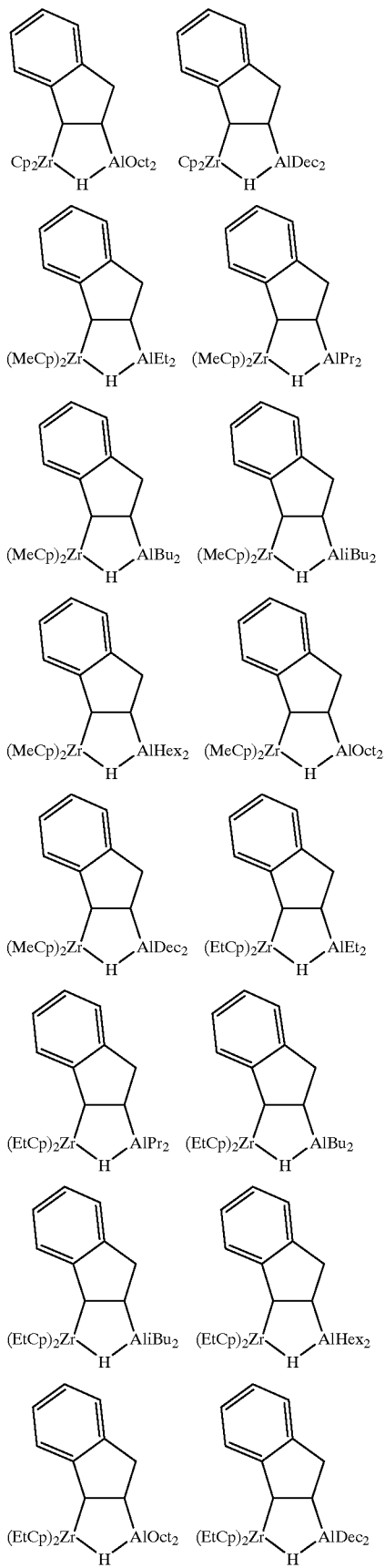

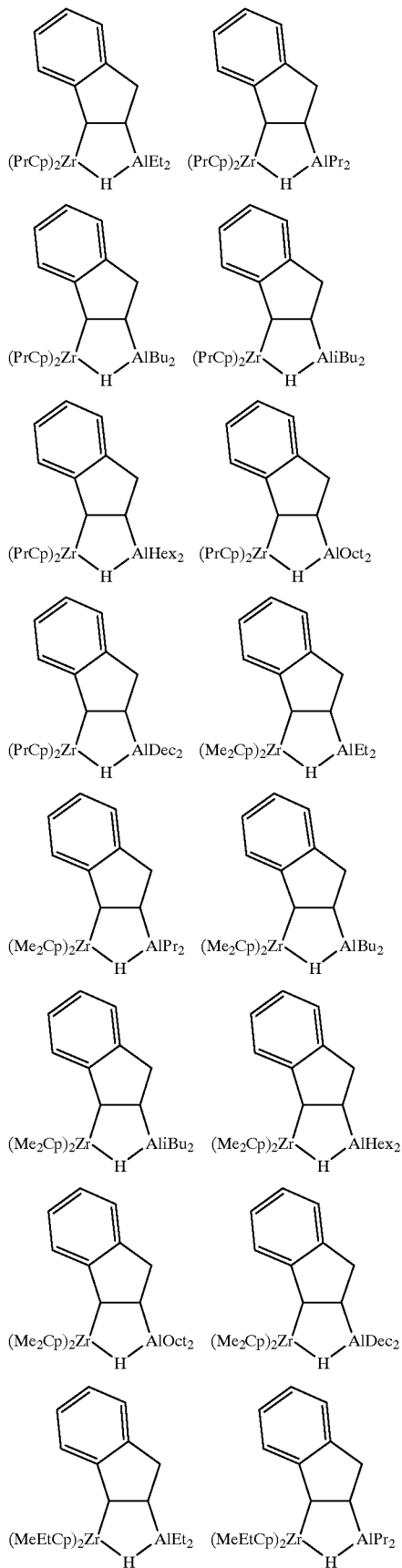
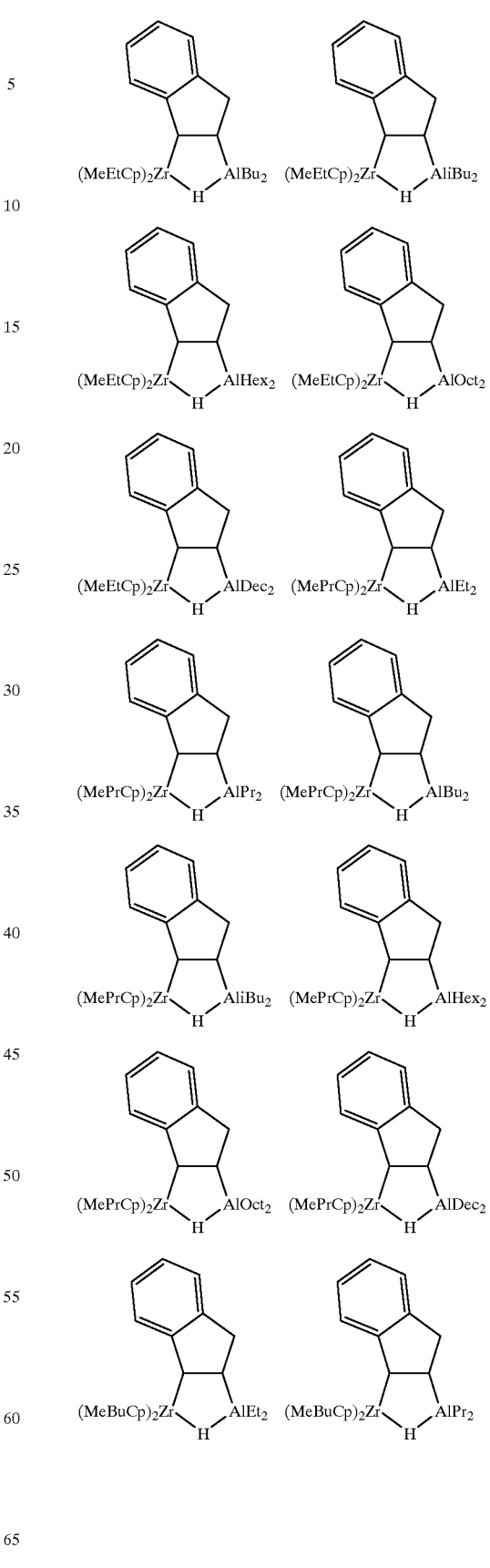

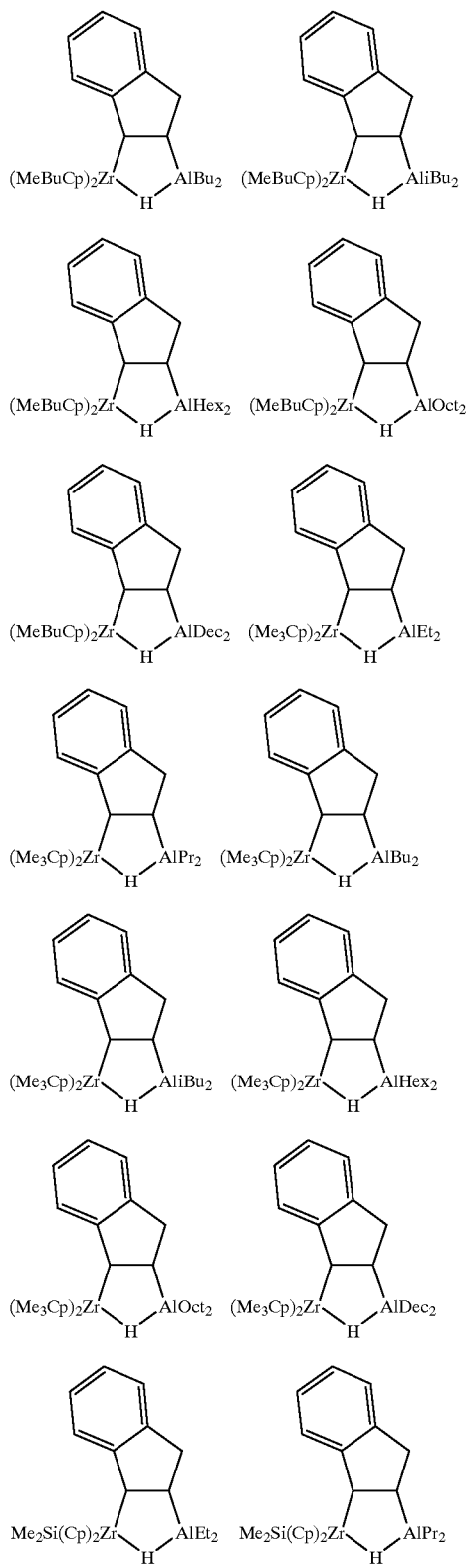
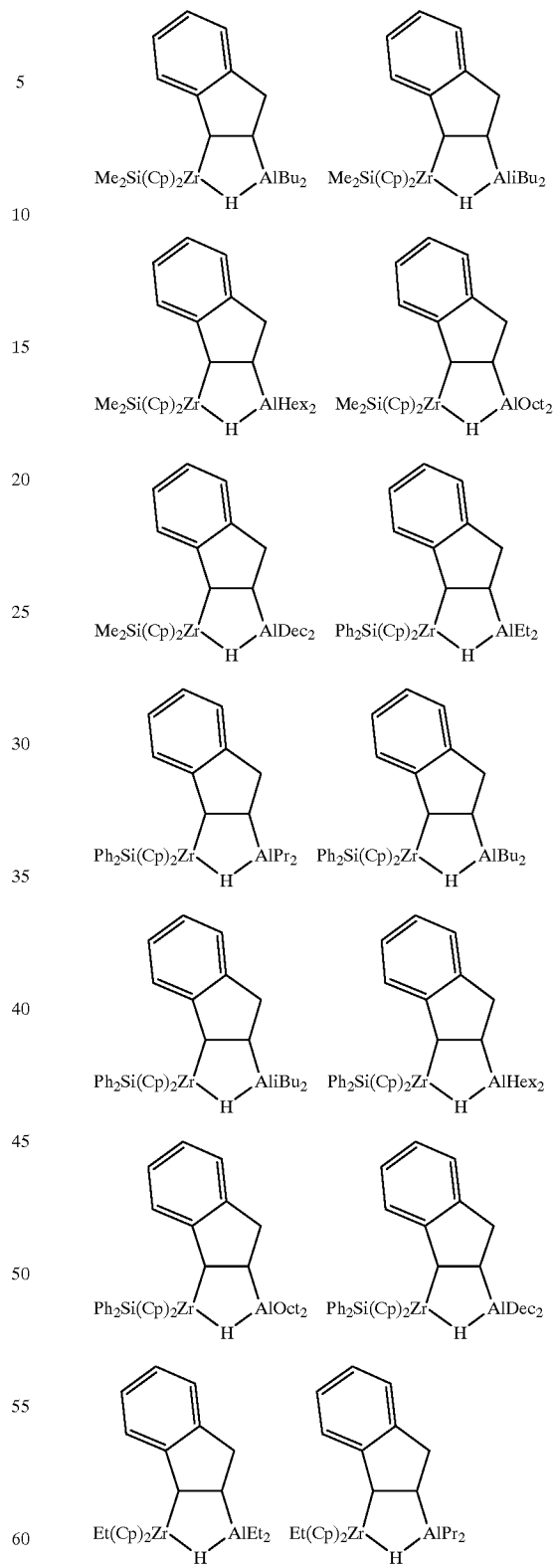

-continued

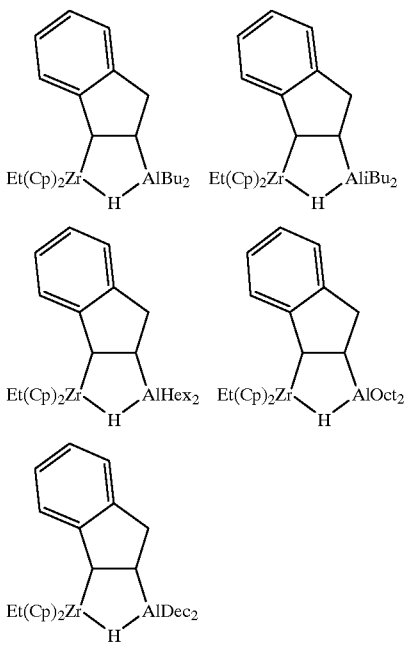

The novel transition metal compound according to the invention may be produced by the following methods.

Production Method 1

Compounds (a), (b) and (c) given below are subjected to mutual contact.

(a) $M^1R^{15}{}_p(OR^{16})_{4-p}$ (b) $M^2R^3{}_mR^4{}_{3-m}$ (c) at least one compound selected from cyclopentadiene, substituted cyclopentadiene, indene and substituted indene In the above formula representing compound (a), $M^1$ is the same as that of formula (I) or (II), namely, denotes an element of Group IVB in the Periodic Table such as zirconium, titanium or hafnium, among which zirconium is particularly preferred.

$R^{15}$ and $R^{16}$ each are a $C_1$–$C_{24}$, preferably $C_1$–$C_{12}$, more preferably $C_1$–$C_8$ hydrocarbon group. Such a hydrocarbon groups includes an alkyl group such as methyl, ethyl, propyl, isopropyl, cyclopropyl, butyl, isobutyl, tert-butyl, cyclobutyl, pentyl, isopentyl, neopentyl, cyclopentyl, hexyl, isohexyl, cyclohexyl, heptyl and octyl; an alkenyl group such as vinyl and allyl; an aryl group such as phenyl, tolyl, xylyl, mesityl, indenyl and naphthyl; and an aralkyl group such as benzyl, trityl, phenethyl, styryl , benzhydril, phenylbutyl, phenylpropyl and neophyl. These groups may have branched chains. p is $0 \leq p \leq 4$.

Specific examples of compound (a) are tetramethylzirconium, tetrabenzylzirconium, tetramethoxyzirconium, tetraethoxyzirconium, tetrapropoxyzirconium, tetrabutoxyzirconium, tetrahexyloxyzirconium, tetraoctyloxyzirconium, tetra(2-ethylhexyloxy) zirconium, tetraphenoxyzirconium, tribenzylmonomethoxyzirconium, tribenzylmonoethoxyzirconium, tribenzylmonopropoxyzirconium, tribenzylmonobutoxyzirconium, dibenzyldimethoxyzirconium, dibenzyldiethoxyzirconium, dibenzyldipropoxyzirconium, dibenzyldibutoxyzirconium, monobenzyltrimethoxyzirconium, monobenzyltriethoxyzirconium, monobenzyltripropoxyzirconium, monobenzyltributoxyzirconium, tetramethyltitanium, tetrabenzyltitanium, tetramethoxytitanium, tetraethoxytitanium, tetrapropoxytitanium, tetrabutoxytitanium, tetrahexyloxytitanium, tetraoctyloxytitanium, tetra(2-ethythexyloxy)titanium, tetraphenoxytitanium, tribenzylmonomethoxytitanium, tribenzylmonoethoxytitanium, tribenzylmonopropoxytitanium, tribenzylmonobutoxytitanium, dibenzylmethoxytitanium, dibenzyldiethoxytitanium, dibenzyldipropoxytitanium, dibenzyldibutoxytitanium, monobenzyltrimethoxytitanium, monobenzyltriethoxytitanium, monobenzyltripropoxytitanium, monobenzytributoxytitanium, tetramethylhafnium, tetrabenzylhafnium, tetramethoxyhafnium, tetraethoxyhafnium, tetrapropoxyhafnium, tetrabutoxyhafnium, tetrahexyloxyhafnium, tetraoctyloxyhafnium, tetra(2-ethylhexyloxy)hafnium, tetraphenoxyhafnium, tribenzylmonomethoxyhafnium, tribenzyltmonoethoxyhafnium, tribenzylmonopropoxyhafnium, tribenzylmonobutoxyhafnium, dibenzyldimethoxyhafnium, dibenzyldiethoxyhafnium, dibenzyldipropoxyhafnium, dibenzyldibutoxyhafnium, monobenzyltrimethoxyhafnium, monobenzyltriethoxyhafnium, monobenzyltripropoxyhafnium and monobenzyltributoxyhafnium.

The above-exemplified compounds (a) encompass those of which $R^{15}$ and $R^{15}$ are not only n- but also a variety of structural isomers such as iso-, s-, t-, neo- types.

Among these compounds, tetramethylzirconium, tetrabenzylzirconium, tetramethylzirconium, tetrapropoxyzirconium, tetrabutoxyzirconium, tetrabutoxytitanium and tetrabutoxyhafnium are preferred. Particularly preferred are those represented by $Zr(OR)_4$ such as tetraethoxyzirconium, tetrapropoxyzirconium and tetrabutoxyzirconium. Two or more of the above compounds may be used in combination.

In the above formula representing compound (b), $M^2$, $R^3$ and $R^4$ are the same as those of formula (I) or (II). Namely, $M^2$ denotes an element of Group IIIA in the Periodic Table and is preferably aluminum or boron, among which aluminum is particularly preferred. $R^3$ and $R^4$ may be the same or different and each are a hydrogen atom or a $C_2$–$C_{18}$, preferably $C_2$–$C_{12}$ more preferably $C_2$–$C_8$ hydrocarbon group. Such a hydrocarbon group includes an alkyl group such as ethyl, propyl, isopropyl, cyclopropyl, butyl, isobutyl, t-butyl, pentyl, isopentyl, neopentyl, cyclopentyl, hexyl, isohexyl, cyclohexyl, heptyl, octyl , decyl, and dodecyl; an alkenyl group such as vinyl and allyl; and an aralkyl group such as phenethyl, styryl, phenylbutyl and phenylpropyl. m is $0 \leq m \leq 3$.

Specific examples of compound (b) are triethylboron, tripropylboron, tributylboron, tripentylboron, trioctylboron, triphenylboron, tribenzylboron, triethylaluminium, tripropylaluminium, tributylaluminium, trihexylaluminium, trioctylaluminium, tridecylaluminium, dimethylaluminiumhydride, diethylaluminiumhydride, dipropylaluminiumhydride, dibutylaluminiumhydride, dihexylaluminiumhydride and dioctylaluminiumhydride.

Needless to mention, the above-exemplified compounds encompass those of which $R^3$ and $R^4$ are not only n-type but also a variety of structural isomers such as iso-, s-, t- and neo- type.

Among these specific compounds, triethylaluminium, tripropylaluminium, tributylaluminium, triisobutylaluminium, trihexylaluminium, trioctylaluminium and tridecylaluminium are preferred. Two or more of the above compounds may be used in combination.

Eligible for compound (c) includes cyclopentadiene, substituted cyclopentadiene, indene and substituted indene. The substituent of each substituted cyclopentadiene and substituted indene includes a $C_1$–$C_{18}$, preferably $C_{1-C12}$ hydrocarbon group. Such a hydrocarbon group includes an alkyl group such as methyl, ethyl, propyl, isopropyl, butyl, isobutyl, t-butyl, pentyl, hexyl and octyl; an alkenyl group such as vinyl and allyl; an aryl group such as phenyl, tolyl and xylyl; and an aralkyl group such as benzyl, phenethyl, styryl and neophyl.

There may be used a compound obtained by forming two or more of the above compounds (c) through a $C_1$–$C_{18}$ hydrocarbon group and/or a silylene group. Such a hydrocarbon group includes an alkylene group such as methylene, ethylene and isopropylene; an alkylene group with an aryl substituent such as diphenylmethylene, methylphenymethylene and ditolylmethylene; an alkylene group with an alkenyl substituent such as divinylmethylene and diallylmethylene; and an alkylene group with an aralkyl substituent such as benzyl, phenethyl, styryl and neophyl. Eligible silylene groups are a silylene group with an alkyl group such as dimethylsilylene and diethylsilylene; a silylene group with an aryl substituent such as diphenysilylene, methylphenysilylene and ditolylsilylene; a silylene with an alkenyl substituent such as divinylsilylene and diallylsilylene; and a silylene group with an aralkyl substituent such as benzyl, phenethyl, styryl and neophyl.

Specific examples of compound (c) are cyclopentadiene, methylcyclopentadiene, ethylcyclopentadiene, propylcyclopentadiene, butylcyclopentadiene, hexylcyclopentadiene, octylcyclopentadiene, dimethylcyclopentadiene, methylethylcyclopentadiene, methylpropylcyclopentadiene, methylbutylcyclopentadiene, trimethylcyclopentadiene, dimethylethylcyclopentadiene, dimethylpropylcyclopendaiene, dimethylbutylcyclopentadiene, methyldiethylcyclopentadiene, methyldipropylcyclopentadiene, methyldibutylcyclopentadiene, triethylcyclopentadiene, diethylpropylcyclopentadiene, diethylbutylcyclopentadiene, ethyldipropylcyclopentadiene, ethyldibutylcyclopentadiene, tripropylcyclopentadiene, tributylcyclopentadiene, tetramethylcyclopentadiene, pentamethylcyclopentadiene, indene, methylindene, ethylindene, propylindene, butylindene, dimethylindene and 4,5,6,7-tetrohydroindene.

Needless to mention, the above-exemplified compounds (c) encompass those of which substituent is not only n-type isomer but also is a variety of structural isomers such as iso-, s-, t- and neo- types. Furthermore, the above examples encompass those of all positional isomers. These compounds may be used in combination.

There may be used a compound obtained by the bond between any of the above compounds through an alkylene group having usually 2–8, preferably 2–3 carbon atoms. For example, ethylenebiscyclopentadiene, ethylenbisindene, propylenebiscyclopentadiene, propylenebisindene, ethylene (indenyl)cyclopentadiene and propylene(indenyl) cyclopentadiene are also eligible for use as compound (c).

Two or more of the above compounds bonded through a silylene group having an alkyl or aryl group are also eligible for use of compound (c). For example, biscyclopentadienyldimethylsilan, biscyclopentadienyldiphenylsilan, bisindenyldimethylsilan, bisindenyldiphenylsilan, cyclopentadienylindenyldimethylsilan and cyclopentadienylindenyldiphenylsilan are eligible for compound (c).

Preferred for compound (c) are cyclopentadiene; substituted cyclopentadiene such as, methylcyclopentadiene, ethylcyclopentadiene, propylcyclopentadiene, butylcyclopentadiene, 1,3-dimethylcyclopentadiene, 1-methyl-3-ethylcyclopentadiene, 3-methyl-1-ethylcyclopentadiene, 1-methyl-3-propylcyclopentadiene, 3-methyl-1-propylcyclopentadiene, 1-methyl-3-butylcyclopentadiene and 3-methyl-1-butylcyclopentadiene; indene; and substituted indene such as methylindene, ethylindene, propylindene and butylindene. These compounds may be used in combination.

The contacting operation may be carried out under an atmosphere of inert gas such as nitrogen and argon in the presence of a liquid inert hydrocarbon including an aromatic hydrocarbon such as benzene, toluene, xylene and ethylbenzene and an aliphatic or alicyclic hydrocarbon such as heptane, hexane, decane, dodecane and cyclohexane with or without stirring.

No particular limitation is imposed on the sequence of contacting each compound. Therefore, compounds (a)–(c) may be contacted in the following sequences.

(1) Compound (a) and (b) are contacted together and thereafter with compound (c)

(2) Compound (a) and (c) are contacted together and thereafter with compound (b)

(3) Compound (b) and (c) are contacted together and thereafter with compound (a)

It has been found that the sequence (2) are particularly preferred.

Upon contacting operation, each of the components may be added at the same time or over a certain period of time as well as at certain interval. The contact of each component may be repeated a number of times. The addition over a certain period of time is particularly preferred.

The contacting operation may be carried out at a temperature of −100 to 200° C., preferably −50 to 150° C., more preferably 50 to 130° C. for a time length of 5 minutes to 250 hours, preferably 30 minutes to 24 hours.

As mentioned above, the contacting operation of compounds (a), (b) and (c) may be conducted using a hydrocarbon solvent in which a certain component is soluble or an aliphatic or alicyclic hydrocarbon solvent in which a certain component is insoluble or hardly soluble. Preferred is the soluble aromatic hydrocarbon solvent. Particularly preferred method for preparing the inventive compound is conducted by adding compound (b) over a certain period of time to compounds (a) and (c) which have been heated to 50–130° C.

The amount of addition of each of compounds (b) and (c) is in the range of 0.01–1,000 mols, preferably 0.1–100 mols, more preferably 0.5–50 mols, per mol of compound (a) and in the range of 0.01–1,000 mols, preferably 0.1–100 mols, more preferably 4–15 mols, per mol of compound (a), respectively.

Upon production of the inventive novel transition metal compound in accordance with Production Method 1, it is preferred to use the following compounds as starting materials.

(a1) a compound of the general formula $Zr(OR^{17})_4$ wherein $R^{17}$ is a $C_2$–$C_{10}$ hydrocarbon group (b1) a compound of the general formula $AlR^{18}{}_3$ wherein $R^{18}$ is a $C_3$–$C_{10}$ hydrocarbon group (c1) a compound selected from indene and substituted indene (c2) a substituted cyclopentadiene compound of the general formula $R^{19}R^{20}C_5H_3$ wherein $R^{19}$ is a $C_1$–$C_{10}$ hydrocarbon and $R^{20}$ is hydrogen or a $C_1$–$C_{10}$ hydrocarbon group A method for producing the inventive transition metal compound using these compounds is conducted by mutually contacting 3 components of compounds (a1), (b1) and (c1) or 4 components of the 3 compounds with compound (c2) with the molar ratio of (b1) to (a1) being more than 5, under an atmosphere of an inert gas such as nitrogen and argon, in the presence of a liquid hydrocarbon such as an aromatic hydrocarbon, an aliphatic hydrocarbon or an alicylic hydrocarbon, at a temperature of 70–120° C.

One of the more preferred methods is conducted by initially mixing compounds (a1) and (c1) in the molar ratio therebetween of more than 4, under an atmosphere of an inert gas such as nitrogen and argon, in the presence of a liquid hydrocarbon such as an aromatic hydrocarbon, an aliphatic hydrocarbon or an alicylic hydrocarbon and then admixing compound (b1) to the resulting mixture in the molar ratio (b1)/(a1) of more than 5, at a temperature of 70–120° C. over at least 10 minutes. The other preferred method is conducted by mixing compounds (a1), (c1) and (c2) in the (c1)/(a1) molar ratio of more than 4, the (c2)/(a1) molar ratio of less than 8 and the (c2)/(c1) molar ratio of less than 1, under an atmosphere of an inert gas such as nitrogen and argon, in the presence of a liquid hydrocarbon such as an aromatic hydrocarbon, an aliphatic hydrocarbon or an alicylic hydrocarbon, followed by the addition of compound (b1) to the resulting mixture in the (b1)/(a1) molar ratio of more than 5, over at least 10 minutes at a temperature of 70–120° C.

In the general formula $Zr(OR^{17})_4$ representing compound (a1), $R^{17}$ is a $C_2$–$C_{10}$ hydrocarbon group which however, has 2–6, preferably 2–4 carbon atoms. Such a hydrocarbon group may be an alkyl group such as ethyl, propyl, butyl, pentyl, hexyl, cyclohexyl, heptyl, octyl, nonyl and decyl; an alkenyl group such as vinyl and allyl; an arylalkyl group such as trityl, phenethyl, styryl, benzhydril, phenylpropyl, phenylbutyl and neophyl; and an alkylaryl group such as tolyl, xylyl, mesityl, indenyl and naphthyl.

Specific examples of compound (a1) are tetraethoxyzirconium, tetrapropoxyzirconium, tetrabutoxyzirconium, tetrahexyloxyzirconium, tetraoctyloxyzirconium, tetra(2-ethylhexyloxy) zirconium and tetraphenoxyzirconium. Two or more of the above compounds may be used in combination. Among these compounds, particularly preferred is tetrabutoxyzirconium.

In the general formula $AlR^{18}_3$ representing compound (b1), $R^{18}$ is a $C_3$–$C_{10}$, preferably $C_3$–$C_8$, more preferably $C_3$–$C_6$ hydrocarbon group. Hydrocarbon groups eligible for $R^{18}$ are an alkyl group such as propyl, butyl, pentyl, hexyl, cyclohexyl, heptyl, octyl, nonyl and decyl; an alkenyl group such as vinyl and allyl; an arylalkyl group such as trityl, phenethyl, styryl benzhydril, phenylpropyl, phenylbutyl and neophyl; and an alkylaryl group such as tolyl, xylyl, mesityl, indenyl and naphthyl.

Specific examples of compound (b1) are tripropylaluminium, tributylaluminium, triisobutylaluminium, trihexylaluminium, trioctylaluminium and tridecylaluminium. Two or more of these compounds may be used in combination. Particularly preferred are tripropylaluminium, triisobutylaluminium and trihexylaluminium.

Compound (c1) is indene or substituted indene. The term "substituted inden" denotes indene having one or more of a $C_1$–$C_{10}$, preferably $C_1$–$C_6$, more preferably $C_1$–$C_4$ hydrocarbon group as a substituent. Such a hydrocarbon group may be an alkyl group such as methyl, ethyl, propyl, butyl, pentyl, hexyl, octyl, nonyl and decyl; an alkenyl group such as vinyl and allyl; an arylalkyl group such as trityl, phenethyl, styryl, benzhydril, phenylpropyl phenylbutyl and neophyl; and an alkylaryl group such as phenyl, tolyl, xylyl, mesityl, indenyl and naphthyl. These hydrocarbon groups may have branched chains.

Specific examples of compound (c1) are indene, 4-methylindene, 5-methylindene, 6-methylindene, 7-methylindene, 4-ethylindene, 5-ethylindene, 6-ethylindene, 7-ethylindene, 4-propylindene, 5-propylindene, 6-propylindene, 7-propylindene, 4-isopropylindene, 5-isopropylindene, 6-isopropylindene, 7-isopropylindene, 4-butylindene, 5-butylindene, 6-butylindene, 7-butylindene, 4-isobutylindene, 5-isobutylindene, 6-isobutylindene, 7-isobutylindene, 4-hexylindene, 5-hexylindene, 6-hexylindene, 7-hexylindene, 4-phenylindene, 5-phenylindene, 6-phenylindene, 7-phenylindene, 4,5-dimethylindene, 4,6-dimethylindene, 4,7-dimethylindene, 5,6-dimethylindene, 5,7-dimethylindene, 6,7-dimethylindene, 4,5-diethylindene, 4,6-diethylindene, 4,7-diethylindene, 5,6-diethylindene, 5,7-diethylindene, 6,7-diethylindene, 4,5-dipropylindene, 4,6-dipropylindene, 4,7-dipropylindene, 5,6-dipropylindene, 5,7-dipropylindene, 6,7-dipropylindene, 4-methyl-5-ethylindene, 4-ethyl-5-methylindene, 5-methyl-6-ethylindene, 5-ethyl-6-methylindene, 6-methyl-7-ethylindene, 6-ethyl-7-methylindene, 4-methyl-5-propylindene, 4-propyl-5-methylindene, 4-methyl-6-ethylindene, 4-ethyl-6-methylindene, 4-methyl-6-propylindene, 4-propyll-6-methylindene, 4methyl-7-ethylindene, 4-ethyl-7-methylindene, 4-methyl-7-propylindeene, and 4-propyl-7-methylindene, among which indene, 4-methylindene, 4-ethylindene, 7-phenylindene and 4,7-dimethylindene are particularly preferred.

In the general formula $R^{19}R^{20}C_5H_3$ representing compound (c2), $R^{19}$ and $R^{20}$ each are hydrogen or a $C_1$–$C_{10}$, preferably $C_1$–$C_6$, more preferably $C_1$–$C_4$ hydrocarbon group. Such a hydrocarbon may be an alkyl group such as methyl, ethyl, propyl, butyl, pentyl, hexyl, cyclohexyl, heptyl, octyl, nonyl and decyl; an alkenyl group such as vinyl and allyl; an arylalkyl group such as trityl, phenethyl, styryl benzhydril, phenylpropyl phenylbutyl and neophyl; and an alkylaryl group such as tolyl, xylyl, mesityl, indenyl and naphthyl. These hydrocarbon groups may have branched chains.

Specific examples of compound (c2) are methylcyclopentadiene, ethylcyclopentadiene, propylcyclopentadiene, butylcyclopentadiene, hexylcyclopentadiene, octylcyclopentadiene, dimethylcyclopentadiene, methylethylcyclopentadiene, methylpropylcyclopendadiene, methylbutylcyclopentadiene, methylhexylcyclopentadiene, methyloctylcyclopentadiene, diethylcyclopentadiene, ethylpropylcyclopentadiene, ethylbutylcyclopentadiene, ethylhexylcyclopentadiene, ethyloctylcyclopentadiene, dipropylcyclopentadiene, propylbutylcyclopentadiene, propylhexylcyclopentadiene, propyloctylcyclopentadiene, dibutylcyclopentadiene, butylhexylcyclopentadiene, butyloctylcyclopentadiene. Each of the substituents bonded to cyclopentadiene may be not only an n-type isomer but also a variety of structural isomers such as iso-, sec-, tert- and neo- types and are not restricted to position. Two or more of the above compounds may be used in combination.

Among the above compounds, particularly preferred are butylcyclopentadiene, 1,3-dimethylcyclopentadiene, 1-methyl-3-ethylcyclopentadiene, 3-methyl-1-ethylcyclopentadiene, 1-methyl-3-propylcyclopentadiene, 3-methyl-1-propylcyclopentadiene, 1-methyl-3-butylcyclopentadiene and 3-methyl-1-butylcyclopentadiene.

Eligible aromatic hydrocarbon solvents for use of the invention are benzene, toluene, xylene and ethylbenzene, while eligible aliphatic or alicyclic hydrocarbon solvents are hexane, heptane, octane, decane, dodecane, and cyclohexane, among which toluene, hexane and cyclohexane are most preferred.

Production Method 2

Method 2 is carried out by mutually contacting the following compounds (d), (b) and (c).

(d) $M^1R^{21}_q(NR^{22}R^{23})_{4-q}$ (b) $M^2R^3_m R^4_{3-m}$ (c) at least one compound selected from cyclopentadiene, substituted cyclopentadiene, indene and substituted indene Compounds (b) and (c) are identical with those used for the above-described Method 1.

In the general formula representing compound (d), $M^1$ is identical with that of formulae (I) and (II), and $R^{21}$, $R^{22}$ and $R^{23}$ each are a $C_1$–$C_{24}$, preferably $C_1$–$C_{12}$, more preferably $C_1$–$C_8$ hydrocarbon group. Such a hydrocarbon group includes an alkyl group such as methyl, ethyl, propyl, isopropyl, cyclopropyl, butyl, isobutyl, tert-butyl, cyclobutyl, pentyl, isopentyl, neopentyl, cyclopentyl, hexyl, isohexyl, cyclohexyl, heptyl and octyl; an alkenyl group such as vinyl and allyl; an aryl group such as phenyl, tolyl, xylyl, mesityl, indenyl and naphthyl; and an aralkyl group such as benzyl, trityl, phenethyl, styryl, benzhydril, phenylbutyl, phenylpropyl and neophyl. These hydrocarbon groups may have branched chains. q is $0 \leq q \leq 4$.

Specific examples of compound (d) are tetra(dimethylamino) zirconium, tetra(diethylamino) zirconium, tetra(dipropoxyamino) zirconium, tetra(dibutylamino) zirconium, tribenzylmono(dimethylamino) zirconium, tribenzylmono(diethylamino) zirconium, tiribenzylmono(dipropoxyamino)zirconium, tribenzylmono(dibutylamino)zirconium, dibenzyldi(dimethylamino)zirconium, dibenzyldi(diethylamino)zirconium, dibenzyldi(dipropylamino)zirconium, dibenzyldi(dibutylamino)zirconium, monobenzyltri(dimethylamino)zirconium, monobenzyltri(diethylamino)zirconium, monobenzyltri(dipropylamino)zirconium, monobenzyltri(dibutylamino)zirconium, tetra(dimethylamino)titanium, tetra(diethylamino)titanium, tetra(dipropylamino)titanium, tetra(dibutylamino)titanium, tribenzylmono(dimethylamino)titanium, tribenzylmono(diethylamino)titanium, tribenzylmono(dipropoxyamino)titanium, tiribenzylmono(dibutylamino)titanium, dibenzyldi(dimethylamino)titanium, dibenzyldi(diethylamino)titanium, dibenzyldi(dipropoxyamino)titanium, dibenzyldi(dibutylamino)titanium, monobenzyltri(dimethylamino)titanium, monobenzyltri(diethylamino)titanium, monobenzyltri(dipropoxyamino)titanium, monobenzyltri(dibutylamino)titanium, tetra(dimethylamino)hafnium, tetra(diethylamino)hafnium, tetra(dipropoxyamino)hafnium, tetra(dibutylamino)hafnium, tribenzylmono(dimethylamino)hafnium, tribenzylmono(diethylamino)hafnium, tribenzylmono(dipropoxyamino)hafnium, tribenzylmono(dibutylamino)hafnium, dibenzyldi(dimethylamino)hafnium, dibenzyldi(diethylamino)hafnium, dibenzyldi(dipropoxyamino)hafnium, dibenzyldi(dibutylamino)hafnium, monobenzyltri(dimethylamino)hafnium, monobenzyltri(diethylamino)hafnium, monobenzyltri(dipropoxyamino)hafnium and monobenzyltri(dibutylamino)hafnium.

Needless to mention, the above-exemplified compounds (d) encompass those of which $R^{21}$, $R^{22}$ and $R^{23}$ are not only n-type but also a variety of structural isomers such as iso-, s-, t- and neo- type.

Among these compounds, preferred are tetra(dimethylamino)zirconium, tetra(diethylamino)zirconium, tetra(dipropoxyamino)zirconium, tetra(dibutylamino) zirconium, tetra(dimethylamino)titanium, tetra(dimethylamino)hafnium and more preferred are $Zr(NR_2)_4$ compounds such as tetra (dimethylamino)zirconium, tetra(diethylamino)zirconium, tetra(dipropoxyamino)zirconium and tetra(dibutylamino)zirconium.

The contacting operation is generally conducted under an atmosphere of an inert gas such as nitrogen and argon in the presence of a liquid inert hydrocarbon such as an aromatic hydrocarbon such as benzene, toluene, xylene and ethylbenzene; or an aliphatic or alicyclic hydrocarbon such as heptane, hexane, decane, dodecane and cyclohexane, with or without stirring.

No particular limitation is imposed on the sequence of contacting each compound. Therefore, compounds (a)–(c) may be contacted in the following sequences.

(1) Compound (d) and (b) are contacted together and thereafter with compound (c)

(2) Compound (d) and (c) are contacted together and thereafter with compound (b)

(3) Compound (b) and (c) are contacted together and thereafter with compound (d)

It has been found that the sequence (2) are particularly preferred.

Upon contacting operation, each of the components may be added at the same time or over a certain period of time as well as at a certain interval. The contact of each component may be repeated a number of times. The addition over a certain period of time is particularly preferred.

The contacting operation may be carried out at a temperature of –100 to 200° C., preferably –50 to 150° C., more preferably 50 to 130° C. for a time length of 5 minutes to 250 hours, preferably 30 minutes to 24 hours.

As mentioned above, the contacting operation of compounds (d), (b) and (c) may be conducted using a hydrocarbon solvent in which a certain component is rendered soluble or an aliphatic or alicyclic hydrocarbon solvent in which a certain component is rendered insoluble or hardly soluble. Preferred is the soluble aromatic hydrocarbon solvent.

The amount of addition of each of compounds (b) and (c) is in the range of 0.01–1,000 mols, preferably 0.1–100 mols, more preferably 0.5–50 mols, per mol of compound (a) and in the range of 0.01–1,000 mols, preferably 0.1–100 mols, more preferably 0.5–50 mols, per mol of compound (d), respectively.

Upon production of the inventive novel transition metal compound in accordance with Production Method 2, it is preferred to use the following compounds as starting materials.

(d1) a compound of the general formula $Zr(OR^{24}_2)_4$ wherein $R^{24}$ is a $C_1$–$C_{10}$ hydrocarbon group (b1) a compound of the general formula $AlR^{18}_3$ wherein $R^{18}$ is a $C_3$–$C_{10}$ hydrocarbon group (c1) a compound selected from indene and substituted indene (c2) a substituted cyclopentadiene compound of the general formula $R^{19}R^{20}C_5H_3$ wherein $R^{19}$ is a $C_1$–$C_{10}$ hydrocarbon and $R^{20}$ is hydrogen or a $C_1$–$C_{10}$ hydrocarbon group A method for producing the inventive transition metal compound using these compounds is conducted by mutually contacting 3 components of compounds (d1), (b1) and (c1) or 4 components of these 3 compounds with an additional compound (c2) in the (b1)/(d1) molar ratio of more than 5, under an atmosphere of an inert gas such as nitrogen and argon, in the presence of a liquid hydrocarbon such as an aromatic hydrocarbon, an aliphatic hydrocarbon or an alicylic hydrocarbon, at a temperature of 70–120° C.

One of the more preferred methods is conducted by initially mixing compounds (d1 and (c1) in the molar ratio therebetween of more than 4, under an atmosphere of an inert gas such as nitrogen and argon, in the presence of a liquid hydrocarbon such as an aromatic hydrocarbon, an aliphatic hydrocarbon or an alicylic hydrocarbon and then admixing compound (b1) to the resulting mixture in the molar ratio (b1)/(d1) of more than 5, at a temperature of 70–120° C. over at least 10 minutes. The other preferred method is conducted by mixing compounds (d1), (c1) and (c2) in the (c1)/(d1) molar ratio of more than 4, the (c2)/(d1) molar ratio of less than 8 and the (c2)/(c1) molar ratio of less than 1, under an atmosphere of an inert gas such as nitrogen and argon, in the presence of a liquid hydrocarbon such as an aromatic hydrocarbon, an aliphatic hydrocarbon or an alicylic hydrocarbon, followed by the addition of compound (b1) to the resulting mixture in the (b1)/(d1) molar ratio of more than 5, over at least 10 minutes at a temperature of 70–120° C.

In the general formula $Zr(NR^{24}_2)_4$ representing compound (d1), $R^{24}$ is a $C_2$–$C_{10}$, preferably $C_2$–$C_6$, more preferably $C_2$–$C_4$ hydrocarbon group. Such a hydrocarbon group includes an alkyl group such as ethyl, propyl, butyl, pentyl, hexyl, cyclohexyl, heptyl, octyl, nonyl and decyl; an alkenyl group such as vinyl and allyl; an arylalkyl group such as trityl, phenethyl, styryl, benzhydril, phenylpropyl, phenylbutyl and neophyl and an alkylaryl group such as tolyl, xylyl, mesityl, indenyl and naphthyl.

Specific examples of compound (d1) are tetra(dimethylamino)zirconium, tetra(diethylamino)zirconium, tetra(dipropylamino)zirconium, tetra(dibutylamino)zirconium, tetra(dihexylamino)zirconium, tetra(dioctylamino)zirconium, tetra(di2-ethylhexylamino)zirconium and tetra(diphenoxyamino)zirconium, among which tetra(dimethylamino)zirconium is particularly preferred. Two or more of the above compounds may be used in combination.

The foregoing explanations as to Compounds (b1), (c1) and (c2) and the hydrocarbon solvent are applied here.

In the above-described Methods 1 and 2, there may be used a variety of methods for isolating the novel transition metal compound form the reaction mixture, in which instance a liquid inert hydrocarbon (for example an aliphatic or an alicyclic hydrocarbon such as pentane, hexane, decane, dodecane and cyclohexane) or a liquid silicon compound (for example, tetramethylsilane, hexamethyldisilane or hexamethyldisiloxane) in both of which the novel transition metal compound is insoluble or hardly soluble, is added to the reaction mixture to recover a solid. There may be employed a conventional recrystallization method so as to recover the intended novel compound of high purity.

The novel transition metal compound according to the invention in combination with the following components (III-1) and/or (III-2) can be used as a catalyst for polymerization of olefins.

Component (III-1): an organoaluminiumoxy compound
Component (III-2): a compound forming ion pairs by reacting with the novel transition metal In this case, the novel transition metal compound can be put in use for a polymerization catalyst component without being isolated from the reaction mixture but should be put in use after being isolated. When such isolation is omitted, the amount of the novel compound formed in the mixture is more than 0.3 mol, preferably more than 0.6 mol, more preferably 0.8 mol, per mol of the charged metallic atom "$M^1$".

The organoaluminiumoxy compound (III-1) has in its molecule an Al—O—Al bond within the number of 1 to 100, preferably 1 to 50. This compound results from the reaction of an organoaluminium compound with water. This reaction is effected usually in the presence of an inert hydrocarbon, typically an aliphatic hydrocarbon such as pentane, hexane and heptane, an alicyclic hydrocarbon such as cyclohexane or the like, or an aromatic hydrocarbon such as benzene, toluene, xylene or the like. Particularly preferred are aliphatic and aromatic hydrocarbons.

Suitable organoaluminum compounds are those of the formula

wherein $R^{25}$ is a $C_1$–$C_{18}$, preferably $C_1$–$C_{12}$ hydrocarbon group such as an alkyl, alkenyl, aryl and aralkyl group, $X^3$ is a hydrogen or halogen atom and s is an integer of $1 \leq s \leq 3$. Ttrialkylaluminums are preferred in which the alkyl group is a methyl, ethyl, propyl, isopropyl, butyl, isobutyl, pentyl, hexyl, octyl, decyl or dodecyl group among which the methyl group is particularly preferred. Two or more of the organoaluminum compounds may be used in combination.

The molar ratio of water to the organoaluminum compound is in the range of 0.25:1 to 1.2:1, preferably 0.5:1 to 1:1. Reaction conditions may be at from –70 to 100° C., preferably –20 to 20° C., and for 5 minutes to 24 hours, preferably 10 minutes to 5 hours. There may be used a water of crystallization contained in a hydrate such as copper sulfate hydrate and aluminum sulfate hydrate or the like. Alternatively, a supply of water may be sought from such components which can produce water in the reaction system.

It has been found that methylaluminoxane, a reaction product of an alkylaluminum and water, is particularly suitable for use as component (III-1).

Needless to mention, two or more of the above aluminumoxy compounds may be used in combination. Alternatively, there may be used a solution obtained by solving or dispersing the aluminumoxy compound in an inert hydrocarbon solvent.

Compound (III-2) is a compound forming ion pairs by reacting with the inventive novel transition metal compound, and typically is borate or borane. A first example of borate is represented by the formula

 (III-2-1)

wherein $L^1$ is a neutral Lewis base, H is a hydrogen atom, [$L^1$-H] is Brönsted acid such as ammonium, anilinium and phosphonium. The ammonium here designates a trialkyl-substituted ammonium such as trimethylammonium, triethylammonium, tripropylammonium, tributylammonium and tri(n-butyl)ammonium; and a dialkylammonium such as di(n-propyl)ammonium and dicyclohexylammounium. The anilinium includes N,N- dialkylanilinium such as N,N-dimethylanilinium, N,N-diethylanilinium and N,N-2,4,6-pentamethylanilinium. The phosphonium includes triarylphosphonium or trialkylphosphonium such as triphenylphosphonium, tirbutylphosphonium, tir(methylphenyl)phosphoniu and tri(dimethylphenyl)

phosphonium. $R^{26}$ and $R^{27}$ may be the same or different and each are an aromatic hydrocarbon group or substituted aromatic hydrocarbon group of $C_6$ to $C_{20}$, preferably $C_6$ to $C_{16}$ which may be cross-linked to one another. The substituents are an alkyl groups such as methyl, ethyl, propyl and isopropyl, and a halogen such as fluorine, chlorine, bromine and iodine. $X^4$ and $X^5$ each are a hydride group, a halide group, a hydrocarbyl including 1 to 20 carbon atoms and a $C_1$–$C_{20}$ substituted hydrocarbyl group of which one or more hydrogen atom is substituted by a halogen atom.

Specific examples of the borate are tributylammoniumtetra(p-tolyl)borate, tributylammoniumtetra(m-tolyl)borate, tributylammoniumtetra(o-fluorophenyl)borate, tributylammoniumtetra(p-fluorophenyl)borate, tributylammoniumtetra(m-fluorophenyl)borate, tributylammoniumtetra(3,5-difluorophenyl)borate, dimethylaniliniumtetra(o-tolyl)borate, dimethylaniliniumtetra(p-tolyl)borate, dimethylaniliniumtetra(m-tolyl)borate, dimethylaniliniumtetra(o-fluorophenyl)borate, dimethylaniliniumtetra(p-fluorophenyl)borate, dimethylaniliniumtetra(m-fluorophenyl)borate, dimethylaniliniumtetra(3,5-difluorophenyl)borate, dimethylaniliniumtetra(pentafluorophenyl)borate, triphenylphosphoniumtetraphenylborate, triphenylphosphoniumtetra(o-tolyl)borate, triphenylphosphoniumtetra(p-tolyl)borate, triphenylphosphoniumtetra(m-tolyl)borate, triphenylphosphoniumtetra(o-fluorophenyl)borate, triphenylphosphoniumtetra(p-fluorophenyl)borate, triphenylphosphoniumtetra(m-fluorophenyl)borate, triphenylphosphoniumtetra(3,5-difluorophenyl)borate and triphenylphosphoniumtetra(pentafluorophenyl)borate.

Furthermore, the borate may be trialkyl-substituted ammonium salts such as triethylammoniumtetra(o-fluorophenyl)borate, triethylammoniumtetra(pentafluorophenyl)borate, triethylammoniumtetra(phenyl)borate, tripropylammoniumtetraphenylborate, tri(n-butyl)ammoniumtetraphenylborate, trimethylammoniumtetra(p-tolyl)borate, tripropylammoniumtetra(o,p-dimethylphenyl)borate, tributylammoniumtetra(p-tifluoromethylphenyl)borate, tributylammoniumtetra(pentafluorophenyl)borate and tri(n-butyl)ammoniumtetra(p-tolyl)borate; N,N-dialkylanilinium salt such as N,N-dimethylaniliniumtetra(phenyl)borate, N,N-diethylaniliniumtetra(phenyl)borate and N,N-2,4,6pentamethylaniliniumtetra(phenyl)borate; and dialkylammonium salt such as di(1-propyl)ammoniumtetra(pentafluorophenyl)borate and dicyclohexylammoniumtetraphenylborate.

Among these compounds, preferred are tributylammoniumtetra(o-fluorophenyl)borate, tributylammoniumtetra(p-fluorophenyl)borate, tributylammoniumtetra(m-fluorophenyl)borate, tributylammoniumtetra(3,5-difluorophenyl)borate, tributylammoniumtetra(pentafluorophenyl)borate, dimethylaniliniumtetra(o-fluorophenyl)borate, dimethylaniliniumtetra(p-fluorophenyl)borate, dimethylaniliniumtetra(m-fluorophenyl)borate, dimethylaniliniumtetra(3,5-difluorophenyl)borate and dimethylaniliniumtetra(pentafluorophenyl)borate and particularly preferred are tributylammoniumtetra(pentafluorophenyl)borate and dimethylaniliniumtetra(pentafluorophenyl)borate.

A second examples of the borate is represented by the formula $$[L^3]^+[BR^{26}R^{27}X^4X^5]^- \qquad (\text{III-2-2})$$

wherein $L^3$ is a carbocation, methylcation, ethylcation, propylcation, isopropylcation, butylcation, isobutylcation, tert-butylcation, pentylcation, tropynumcation, benzylcation and tritylcation and $R^{26}$, $R^{27}$, $X^4$ and $X^5$ each are the same as defined in formula (III-2-1).

Specific examples are trityltetraphenylborate, trityltetra(o-tolyl)borate, trityltetra(p-tolyl)borate, trityltetra(m-tolyl)borate, trityltetra(o-fluorophenyl)borate, trityltetra(p-fluorophenyl)borate, tritltetra(m-fluorophenyl)borate, trityltetra(3,5-difluorophenyl)borate, trityltetra(pentafluorophenyl)borate, tropyniumtetraphenylborate, tropyniumtetra(o-tolyl)borate, tropyniumtetra(p-tolyl)borate, tropyniumtetra(m-tolyl)borate, tropyniumtetra(o-fluorophenyl)borate, tropyniumtetra(p-fluorophenyl)borate, tropyniumtetra(o-fluorophenyl)borate, tropyniumtetra(3,5-difluorophenyl)borate and tropyniumtetra(pnetafluorophenyl)borate. Preferred are trityltetra(o-fluorophenyl)borate, trityltetra(p-fluorophenyl)borate, trityltetra(m-fluorophenyl)borate, trityltetra(pentafluorophenyl)borate, tropyliumtetra(o-fluorophenyl)borate, tropyliumtetra(p-fluorophenyl)borate, tropyliumtetra(m-fluorophenyl)borate, tropyliumtetra(3,5-difluorophenyl)borate and tropyliumtetra(pnetafluorophenyl)borate. More preferred are trityltetra(pentafluorophenyl)borate and tropyniumtetra(pentafluorophenyl)borate.

Specific examples of the borane compound are triphenylborane, tri(o-tolyl)borane, tri(p-tolyl)borane, tri(m-tolyl)borane, tri(o-fluorophenyl)borane, tri(p-fluorophenyl)borane, tri(m-fluorophenyl)borane, tri(3,5-difluorophenyl)borane and tri(pentafluorophenyl)borane. Preferred are tri(m-fluorophenyl)borane, tri(3,5-difluorophenyl)borane and tri(pentafluorophenyl)borane. More preferred is tri(pentafluorophenyl)borane.

The olefin-polymerization catalyst of the inventive novel transition metal in combination with components (III-1) and/or the component (III-2) may be supported on a carrier so as to be a solid catalyst.

Eligible for use as such a carrier are an inorganic carrier and/or a particulate polymer carrier. The inorganic carrier may be a metal, a metal oxide, a metal chloride, a metal carbonate or a carbonaceous material. Suitable metal for use as the inorganic carrier are iron, aluminum, nickel or the like.

Eligible metal oxide are sole oxides or double oxides of Groups I to VIII in the Periodic table such as natural or synthetic double oxides represented by the following formulae:

$SiO_2$, $Al_2O_3$, MgO, CaO, $B_2O_3$, $TiO_2$, $ZrO_2$, $Fe_2O_3$, $Al_2O_3$.MgO, $Al_2O_3$.CaO, $Al_2O_3$.SiO_2, $Al_2O_3$.MgO.CaO, $Al_2O_3$.MgO.SiO_2, $Al_2O_3$.CuO, $Al_2O_3$.Fe_2O_3, $Al_2O_3$.NiO, $SiO_2$.MgO

These formulae are not molecular formulae but indicate the compositions.

There is no particular limitation imposed on the structure and ratio of component of the double oxides.

The metal oxides may have absorbed thereto small quantities of moisture and may further a small amount of impurities.

Eligible metal chloride for use as the carrier are preferably the chlorides of alkaline metals and alkaline earth metals and are specifically $MgCl_2$ and $CaCl_2$.

Eligible metal carbonate are the carbonates of alkaline metals and alkaline earth metals and are specifically magnesium carbonate, calcium carbonate and barium carbonate. Eligible carbonaceous materials are carbon black and activated carbon. Particularly preferred inorganic carriers are the metal oxides, silica and alumina.

The inorganic carrier is preferably put in use after the amount of the surface hydroxyl group is adjusted to 0.8 to 1.5 mmol/g by calcination at a temperature of 200–800° C., preferably 400–600° C. in the air or under an atmosphere of an inert gas such as nitrogen or argon.

Although no particular limitation imposed on the properties of these inorganic carriers, they should preferably have an average particle size of 5 to 200 $\mu$m, preferably 10 to 150 $\mu$m, a specific surface of 150 to 1,000 m$^2$/g, preferably 200 to 500 m$^2$/g, a pore volume of 0.3 to 2.5 cm$^3$/g, preferably 0.5 to 2.0 cm$^3$/g and an apparent specific gravity of 0.20 to 0.50 g/cm$^3$, preferably 0.25 to 0.45 g/cm$^3$. Although these inorganic carriers may be used as they are, the may be put in use after being contacted with an organoaluminum compound such as trimethylaluminum, triethylaluminum, trisiobutylaluminum and trihexylaluminum or an organoaluminumoxy compound having an Al—O—Al bond.

No particular limitation is imposed on the sequence of contacting the inventive transition metal compound, components (III-1) and/or (III-2) and the carrier (IV). The following sequences may be arbitrary selected.

(1) The transition metal compound and compound (III-1) and/or (III-2) are contacted together and thereafter with compound (IV)

(2) The transition metal compound and compound (IV) are contacted together and thereafter with compound (III-1) and/or (III-2)

(3) Compound (III-1) and/or (III-2) and compound (IV) are contacted together and thereafter with the transition metal compound It has been found that the sequence (1) is particularly preferred. The contacting operation may be carried out under an atmosphere of an inert gas such as nitrogen or argon in the presence of a liquid inert hydrocarbon including a $C_6$–$C_{12}$ aromatic hydrocarbon such as benzene, toluene, xylene and ethylbenzene or a $C_5$–$C_{12}$ aliphatic or alicyclic hydrocarbon such as heptane, hexane, decane, dodecane and cyclohexane, with or without being stirred. This contacting operation should be conducted at a temperature of –100 to 200° C., preferably –50 to 100° C. for about 10 minutes to 50 hours, preferably one hour to 24 hours.

As mentioned above, there may be used an aromatic hydrocarbon solvent in which a particular component is rendered soluble or an aliphatic or alcyclic hydrocarbon solvent in which a particular component is rendered insoluble or hardly soluble. In the case where the contacting operation is carried out stepwise, the soluble aromatic hydrocarbon solvent having been used in a previous step need not to be removed and thus may be put in use for the following steps as it is. Alternatively, after the contacting reaction having been conducted using the soluble solvent, the intended product is recovered in the form of a solid by adding the liquid inert hydrocarbon in which a particular component is insoluble or slightly soluble (for example an aliphatic or alicyclic hydrocarbon such as pentane, hexane, decane, dodecane and cyclohexane) or by removing part or all of the aromatic hydrocarbon solvent by means of drying and thereafter the following contacting operation of the intended solid product may be conducted using any of the above-mentioned inert hydrocarbon solvents. The contacting operation of each component may be repeated a number of times.

Although no particular limitation is imposed on the amount of use of each of the inventive transition metal compound, components (III-1) and/or (III-2) and the carrier (IV), the following ranges are preferred.

The amount of component (III-1) is represented by the atomic ratio aluminum in (III-1) to transition metal in the transition metal compound which is in the range of 1 to 100,000, preferably 5 to 1,000, more preferably 50 to 200. The amount of component (III-2) is represented by the atomic ratio of boron in (III-2) to transition metal in the transition metal compound which is in the range of 0.01 to 100, preferably 0.1 to 50, more preferably 0.2 to 10.

The amount of the carrier (IV) is 1 gram per 0.0001 to 5 mmol, preferably 0.001 to 0.5 mmol, more preferably 0.01 to 0.1 mmol of the transition metal composition.

The olefin polymerization catalyst can be obtained in solid by mutually contacting the transition metal compound, components (III-1) and/or (III-2) and the carrier (IV) in the above-mentioned sequence (1), (2) or (3) and then removing the solvent. The removal of the solvent should be carried out at atmospheric pressure or under reduced pressure at a temperature of 0 to 200° C., preferably 20 to 150° C. for one minute to 50 hours, preferably 10 minutes to 10 hours.

Alternatively, the olefin polymerization catalyst can also be produced by the following methods.

(4) The transition metal compound and the carrier (IV) are contacted to one another, followed by the removal of the solvent to form a solid catalyst component, which is then contacted to components (III-1) and/or (III-2) under polymerization conditions.

(5) Components (III-1) and/or (III-2) and the carrier are contacted to each other to form a solid catalyst component which is then contacted to the transition metal compound under polymerization conditions.

In the above methods (4) and (5), the ratio of components and the conditions of contacting and solvent removal are the same as those already described above.

The olefin polymerization catalyst obtained in this way may be used after the pre-polymerization of monomer as necessary.

The above-described polymerization catalyst can be used for homo- or co-polymerization of olefins. The "olefins" used herein include $\alpha$-olefins, cyclic olefins, dienes, trienes and styrene homologs.

Eligible $\alpha$-olefins are those having a carbon number of 2 to 12, preferably 2 to 8, and chosen from the group consisting of ethylene, propylene, butene-1, hexene-1, 4-mehtylpentene-1 and the like. They may be homopolymerized using the inventive catalyst component or two or more of them may be copolymerized as by alternating, random or block copolymerization processes. Exemplified as $\alpha$-olefin copolymers are those of ethylene with an $\alpha$-olefin comonomer of a carbon number of 3 to 12, preferably 3 to 8, such as ethylene-propylene, ethylene-butene-1, ethylene-hexene-1 or ethylene-4-methylpentene-1, or of propylene with an $\alpha$-olefin comonomer of a carbon number of 3 to 12, preferably 3 to 8, such as propylene-butene-1, propylene-4-methylpentene-1, propylene-hexene-1 and propylene-octene-1. In either copolymer, the content of the comonomer may be variable within the range of less than 90% by mol of total monomer. Generally, ethylene-based copolymers have a comonomer content of not more than 40%, preferably smaller than 30%, more preferably below 20%, whereas propylene-based copolymers have a similar content in the range of 1 to 90%, more preferably 10 to 70%, each such percentage being by mol based on total monomer.

Suitable cyclic olefins include those having a carbon number of 3 to 24, preferably 3 to 18, such as cyclopropene, cyclobutene, cyclopentene, cyclohexene, 3-methylcyclohexene, cyclooctene, cyclodecene, tetracyclodecene, octacyclodecene, dicyclopentadiene, norbornene, 5-methyl-2-norbornene, 5-ethyl-2-norbornene, 5-isobutyl-2-norbornene, 5,6-dimethyl-2-norbornene, 5,5,6- trimethyl-2-norbornene and ethylidenenorbornene. They may be copolymerized usually with a given α-olefin in which instance the content of the cyclic olefin in the resulting copolymer is in the range of 1 to 50% by mol, preferably 2 to 50% by mol.

Suitable dienes and trienes are polyenes of a carbon number of 4 to 24, preferably 4 to 18. Examples include butadiene, 1,4hexadiene, 1,5-hexadiene, 1,9-decadiene, 1,13-tetradecadiene, 2,6-dimethyl-1,5-heptadiene, 2-methyl-2,7-octadiene, 2,7-dimethyl-2,6-octadiene and 1,5,9-decatriene. Chain dienes or trienes copolymerizable with a given α-olefin are usually contained in the copolymer in an amount of 0.1 to 50% by mol, preferably 0.2 to 10% by mol.

Eligible styrene homologs are styrene and styrene derivatives such as t-butylstyrene, α-methylstyrene, p-methylstyrene, divinylbenzene, 1,1-diphenylethylene, N,N-dimethyl-p-aminoethylstyrene and N,N-diethyl-p-aminoethylstyrene.

The inventive catalyst may be applied to slurry, solution and vapor polymerization processes. Slurry and vapor phase modes of reaction may be conveniently chosen which are conducted in a substantially oxygen-free, moisture-free state and in the presence of or in the absence of an inert solvent. Suitable solvents may be aliphatic hydrocarbons such as hexane, heptane and the like, aromatic hydrocarbons such as benzene, toluene, xylene and the like and alicyclic hydrocarbons such as cyclohexane, methylcyclohexane and the like. Reaction temperatures may be at from 20 to 200° C., preferably 50 to 100° C., reaction temperatures at from atmospheric to 70 kg/cm²G, preferably atmospheric to 20 kg/cm²G and reaction timelengths at from 5 minutes to 10 hours, preferably 5 minutes to 5 hours.

The molecular weight of a polymer to be formed can be effectively controlled by feeding a predetermined amount of hydrogen into the reaction system, although this control may be also effected by adjusting the reaction temperature, molar ratio of the catalyst and other parameters.

There may be used some scavengers for removing moisture from the reaction system. Such scavengers include an organoaluminum compound such as trimethylaluminum, triethylaluminum and triisobutylaluminum, the aforesaid organoaluminumoxy compound, a modified organo-aluminum having a branched alkyl group, an organo-zinc such as diethyl zinc and dibutyl zinc, an organo-magnesium such as diethyl magnesium, dibutyl magnesium and ethylbutyl magnesium and a Grignard compound such as ethyl magnesium chloride and butyl magnesium chloride. Amongst these, triethyl aluminum, triisobutyl aluminum, ethylbutyl magnesium and triethyl aluminum are preferred.

The inventive catalyst may be used suitably used for a multi-stage mode of polymerization involving different hydrogen concentrations, monomer concentrations, polymerization pressures and temperatures and other reaction parameters.

The invention will be described in more details by way of the following examples. However, it is to be understood that the invention is not intended to be limited to the specific embodiments.

The measurements for the physical properties of the polymers obtained in Examples were conducted in accordance with the following methods.

Melt Flow Rate (MFR): measured in accordance with Condition No. 4 in Table 1 of JIS K 7210 at 190° C. with load of 2.16 kg Bulk Density: measured in accordance with JIS K-6721 using a bulk density measurement device manufactured by Kuramochi Kagaku Co., Ltd Molecular Weight Distribution (Mw/Mn): measured of a flow of 0.1 mil/min at 135° C. by a gel permeation chromatography (Waters Co. Model No. 1500 GPC) using an ortho-dichlorobenzene (GMH-6 by Column Toyo Soda Co.).

EXAMPLE 1

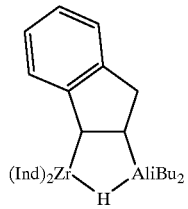

(A)

A 200 cc three-necked flask was charged with 20 ml refined toluene under nitrogen atmosphere and then with 1 mmol Zr(OBu)$_4$ and 8 mmol indene and heated to 90° C. The resulting solution was added with a toluene solution containing 8 mmol of triisobutylaluminum over 100 minutes and stirred at 90° C. for 4 hours.

The solution was kept at a temperature of 40° C. to remove a low boiling substance using an oil pump. The oily liquid thus obtained was depressurized to about 10$^{-6}$ Torr using a high-vacuum line thereby obtaining a solid. This solid was added with 20 ml pentane and then stirred, followed by cooling to a temperature of −78° C. thereby obtaining a dark brownish liquid and precipitate. Immediately after this, these were centrifuged to separate the precipitate and the solution. The precipitate was again added with pentane and cooled, followed by centrifugation thereby obtaining a yellowish solid. The solid was added with toluene and dissolved at a temperature of 60° C. so as to be saturated. After disposing still at a temperature of −30° C., there was obtained 0.44 gram of yellow crystal (Compound A of the above formula). The resulting crystal was subjected to $^1$H-NMR analysis and X-ray analysis.

The results of $^1$H-NMR analysis are as follows:

$^1$H-NMR (manufactured by BRUKER Co., 600 mHz) (Deuterated Solvent: C$_6$D$_6$, Concentration, Criterion for Chemical Shift: tetramethylsilane (TMS)): 7.4 (d, 1H), 7.3 (d, 1H), 7.1 (d, 1H), 7.0 (t, 1H), 6.9 (t, 1H), 6.8 (1H), 6.8 (1H), 6.8 (1H), 6.8 (1H),6.7 (t, 1H), 6.7 (t, 1H), 5.8 (s, 1H), 5.5 (s, 1H), 5.4 (s, 1H), 5.1 (s, 1H), 4.6 (t, 1H), 4.3 (t, 1H), 3.5 (d,d, 1H), 2.9 (d,d, 1H), 2.4 (m, 1H), 2.2 (m, 1H), 1.4 (d, 3H), 1.4 (d, 3H), 1.3 (d, 3H), 1.3 (d, 3H), 0.8 (d,d, 1H), 0.6 (d,d, 1H), 0.6 (d,d, 1H), 0.4 (d,d,t, 1H), 0.3 (d,d,1 H), 0.0 (d, 1H), −2.2 (s, 1H)

FIG. 1 shows the structure of the above compound revealed by X-ray analysis.

EXAMPLE 2

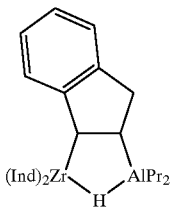

(B)

$(Ind)_2Zr\diagdown_H\diagup AlPr_2$

A 200 cc three-necked flask was charged with 20 ml reined toluene under nitrogen atmosphere and further with 1 mmol Zr(OBu)$_4$ and 8 mmol indene and heated to 110° C. The resulting solution was added with a toluene solution containing 8 mmol of tripropylaluminum over a period of 60 minutes and stirred at 110° C. for 60 minutes. The resulting solution was subjected to the same procedures of Example 1 thereby obtaining 0.4 gram of Compound B of the above formula.

$^1$H-NMR (manufactured by Joel Co., 400 mHz) (Deuterated Solvent: $C_6D_6$, Concentration, Criterion for Chemical Shift: tetramethylsilane (TMS)): 7.4–6.7 (m, 12H), 5.6 (s, 1H), 5.4 (s, 1H), 5.3 (s, 1H), 5.3 (s, 1h), 4.7 (t, 1H), 4.4 (t, 1H), 3.5 (d,d, 1H), 2.9 (d,d, 1H), 2.0 (m, 2H), 1.8 (m, 2H), 1.4 (t, 3H), 1.3 (t, 3H), 1.3 (d,3H), 0.8 (t, 1H), 0.7 (m, 1H), 0.6 (m, 1H), 0.4 (m, 1H), 0.3 (m, 1H), 0.3 (m, 1H), 0.0 (d, 1H), −2.4 (s, 1H)

EXAMPLE 3

The following reaction operations were conducted using Compound A.

A 100 ml flask was charged in nitrogen atmosphere with Compound A (Zr 0.4 mmol atom) and 5 ml toluene to obtain a toluene solution. The solution was added with 40 ml methylaluminoxane (1 mmol/ml Al concentration) and stirred at room temperature for one hour.

A 200 ml flask was charged in nitrogen atmosphere with 10 grams of SiO$_2$ (Fuji Davision #952, surface area 300 m$^2$/g) that had been calcined at 400° C. for 5 hours and total weight of the above solution, followed by nitrogen blow in vacuum to remove the solvent thereby obtaining a solid catalyst component with flowability. A 3 liter stainless steel autoclave equipped with a stirrer was adjusted to a temperature of 75° C. by flowing a hot water into the jacket. The autoclave was charged with 0.25 ml hexane solution of triethylaluminum (0.5 mmol/ml) and 150 mg of the above solid catalyst, whereupon polymerization reaction was initiated and continued for 2 hours with supply of a butene-1 gas and an ethylene gas such that the molar ratio therebetween is 0.10 with a total pressure maintained at 9 kg/cm$^2$G.

Analysis indicated a catalytic activity of 430 kg/g Zr. The resulting ethylene copolymer was 3.6 g/10 min in melt flow rate (MFR), 0.9211 g/cm$^3$ in density, 2.7 in average molecular weight (Mw/Mn) and 0.48 g/cm$^3$ in bulk density.

EXAMPLE 4

A 200 cc three necked flask was charged in nitrogen atmosphere with 20 ml refined toluene and then with 1 mmol Zr(OBu)$_4$, 8 mmol indene and 8 mmol triisobutylaluminum and stirred under reflux by heating for 4 hours. $^1$H-NMR analysis revealed that Compound A was formed in an amount of 35% of the charged Zr.

A 100 ml flask was charged in nitrogen atmosphere with the solution (Zr 0.4 mmol atom) obtained above and 5 ml toluene to obtain a toluene solution. The solution was added with 40 ml solution of methylaluminoxane (1 mmol/ml Al concentration) and stirred at room temperature for one hour.

A 200 ml flask was charged with 10 grams of SiO$_2$ (surface area 300 m$^2$/g, Grade No. 952 of Fuji Davison) which had been calcined at 400° C. for 5 hours, followed by addition of total weight of the above solution. The admixture was dried by nitrogen blow in vacuum to remove the solvent therefrom thereby obtaining a solid catalyst component with fluidity.

A 3 liter stainless steel autoclave equipped with a stirrer and purged with nitrogen was adjusted to a temperature of 75° C. by flowing a hot water into the jacket. The autoclave kept at 75° C. was charged with 0.25 ml hexane solution of triethylaluminum (0.5 mmol/ml) and 150 mg of the above solid catalyst. The admixture was charged with a butene-1 gas and an ethylene gas while the molar ratio therebetween is adjusted to be 0.10 thereby initiating the polymerization. The reaction was continued for 2 hours with a continuous charge of these gases with a total pressure maintained at 9 kg/cm$^2$G.

Analysis revealed that a catalytic activity was 100 kg/g Zr and the resulting ethylene copolymer was 4.8 g/10 min in MFR, 0.9205 g/cm$^3$ in density, 3.2 in Mw/Mn and 0.40 g/cm$^3$ in bulk density.

EXAMPLE 5

A 200 cc three-necked flask was charged under nitrogen atmosphere with 20 ml refined toluene and then with 1 mmol Zr(OBu)$_4$ and 8 mmol indene and heated to 90° C. The resulting solution was added with a toluene solution containing 8 mmol of triisobutylaluminum over a period of 100 minutes and stirred at 90° C. for 4 hours. 1H-NMR analysis revealed that Compound A was formed in an amount of 72% of the charged Zr. The peak of the other zirconocene compounds was not found at 3.6–6.8 ppm within which the peak of a zirconocene compound is usually found.

A 100 ml flask was charged under nitrogen atmosphere with the above solution (Zr 0.4 mmol atom) and 5 ml toluene to obtain a toluene solution. The admixture was added with 40 ml methylalminoxane (1 mmol/ml Al concentration) and stirred at room temperature for one hour.

A 200 ml flask was charged with 10 grams of SiO$_2$ (surface area 300 m$^2$/g, Grade No. 952 of Fuji Davison) which had been calcined at 400° C. for 5 hours, followed by addition of total weight of the above solution. The admixture was dried by nitrogen blow in vacuum to remove the solvent therefrom thereby obtaining a solid catalyst component with fluidity.

A 3 liter stainless steel autoclave equipped with a stirrer and purged with nitrogen was heated to a temperature of 75° C. by flowing a hot water into the jacket. The autoclave kept at 75° C. was charged with 0.25 ml hexane solution of triethylaluminum (0.5 mmol/ml) and 150 mg of the above solid catalyst. The admixture was charged with a butene-1 gas and an ethylene gas while the molar ratio therebetween is adjusted to 0.10 thereby initiating the polymerization. The reaction was continued for 2 hours with a continuous charge of these gases with a total pressure maintained at 9 kg/cm$^2$G.

Analysis revealed that a catalytic activity was 280 kg/g Zr and the resulting ethylene copolymer was 4.5 g/10 min in MFR, 0.9217 g/cm$^3$ in density, 2.9 in Mw/Mn and 0.41 g/cm$^3$ in bulk density.

EXAMPLE 6

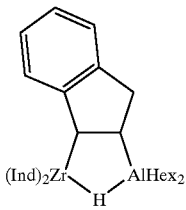

(C)

A 200 cc three-necked flask was charged in nitrogen atmosphere with 20 ml refined toluene, and then with 1 mmol Zr(OBu)$_4$ and 8 mmol indene and heated to 110° C. The resulting solution was added with a toluene solution containing 8 mmol of trihexylaluminum over a period of 90 minutes and stirred at 110° C. for one hour. 1H-NMR analysis revealed that Compound C of the above formula was formed in an amount of 70% of the charged Zr.

A 100 ml flask was charged in nitrogen atmosphere with the above solution (Zr 0.4 mmol atom) and 5 ml toluene to obtain a toluene solution. The admixture was added with 40 ml methylalminoxane (1 mmol/ml Al concentration) and stirred at room temperature for one hour.

A 200 ml flask was charged with 10 grams of SiO$_2$ (surface area 300 m$^2$/g, Grade No. 952 of Fuji Davison) which had been calcined at 400° C. for 5 hours, followed by addition of total weight of the above solution. The admixture was dried by nitrogen blow in vacuum to remove the solvent therefrom thereby obtaining a solid catalyst component with fluidity.

A 3 liter stainless steel autoclave equipped with a stirrer and purged with nitrogen was adjusted to a temperature of 75° C. by flowing a hot water into the jacket. The autoclave kept at 75° C. was charged with 0.25 ml hexane solution of triethylaluminum (0.5 mmol/ml) and 150 mg of the above solid catalyst. The admixture was charged with a butene-1 gas and an ethylene gas while the molar ratio therebetween is adjusted to 0.10 thereby initiating the polymerization. The reaction was continued for 2 hours with a continuous charge of these gases with a total pressure maintained at 9 kg/cm$^2$G.

Analysis revealed that a catalytic activity was 310 kg/g Zr and the resulting ethylene copolymer was 4.2 g/10 min in MFR, 0.9209 g/cm$^3$ in density, 3.5 in Mw/Mn and 0.40 g/cm$^3$ in bulk density.

EXAMPLE 7

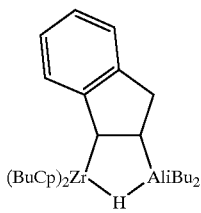

(D)

A 200 cc three-necked flask was charged in nitrogen atmosphere with 20 ml refined toluene and then with 1 mmol Zr(NMe$_2$)$_4$, 5 mmol indene and 4 mmol n-butylcycdopentadiene and heated to 90° C. The resulting solution was added with 8 mmol a toluene solution containing 8 mmol of triisobutylaluminum over a period of one hour and stirred at 90° C. for 4 hours. $^1$H-NMR analysis revealed that Compound D of the above formula was formed in an amount of 75% of the charged Zr.

A 200 ml flask was charged with 10 grams of SiO$_2$ (surface area 300 m$^2$/g, Grade No. 952 of Fuji Davison) which had been calcined at 400° C. for 5 hours, followed by addition of total weight of the above solution. The admixture was dried by nitrogen blow in vacuum to remove the solvent therefrom thereby obtaining a solid catalyst component with fluidity.

A 3 liter stainless steel autoclave equipped with a stirrer and purged with nitrogen was adjusted to a temperature of 75° C. by flowing a hot water into the jacket. The autoclave kept at 75° C. was charged with 0.25 ml hexane solution of triethylaluminum (0.5 mmol/ml) and 150 mg of the above solid catalyst. The admixture was charged with a butene-1 gas and an ethylene gas while the molar ratio therebetween is adjusted to 0.06 thereby initiating the polymerization. The reaction was continued for 2 hours with a continuous charge of these gases with a total pressure maintained at 9 kg/cm$^2$G.

Analysis revealed that a catalytic activity was 400 kg/g Zr and the resulting ethylene copolymer was 4.1 g/10 min in MFR, 0.9213 g/cm$^3$ in density, 2.9 in Mw/Mn and 0.41 g/cm$^3$ in bulk density.

EXAMPLE 8

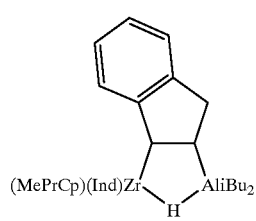

(E)

A 200 cc three-necked flask was in nitrogen atmosphere with 20 ml refined toluene and then with 1 mmol Zr(OBu)$_4$, 8 mmol indene and 3 mmol methylpropylcyclopentadiene and heated to 90° C. The resulting solution was added with a toluene solution containing 8 mmol of triisobutylaluminum over a period of 90 minutes and stirred at 90° C. for 4 hours. $^1$H-NMR analysis revealed that Component A and Compound E of the above formula each were formed in an amount of 59% and 10%, respectively, of the charged Zr.

A 100 ml flask was charged in nitrogen atmosphere with the above solution (Zr 0.4 mmol atom) and 5 ml toluene to obtain a toluene solution. The admixture was added with 40 ml methylalminoxane (1 mmol/ml Al concentration) and stirred at room temperature for one hour.

A 200 ml flask was charged with 10 grams of SiO$_2$ (surface area 300 m$^2$/g, Grade No. 952 of Fuji Davison) which had been calcined at 400° C. for 5 hours, followed by addition of total weight of the above solution. The admixture was dried by nitrogen blow in vacuum to remove the solvent therefrom thereby obtaining a solid catalyst component with fluidity.

A 3 liter stainless steel autoclave equipped with a stirrer and purged with nitrogen was adjusted to a temperature of 75° C. by flowing a hot water into the jacket. The autoclave kept at 75° C. was charged with 0.25 ml hexane solution of triethylaluminum (0.5 mmol/ml) and 150 mg of the above solid catalyst. The admixture was charged with a butene-1 gas and an ethylene gas while the molar ratio therebetween is adjusted to 0.08 thereby initiating the polymerizabon. The reaction was continued for 2 hours with a continuous charge of these gases with a total pressure maintained at 9 kg/cm$^2$G.

Analysis revealed that a catalytic activity was 380 kg/g Zr and the resulting ethylene copolymer was 2.3 g/10 min in MFR, 0.9203 g/cm$^3$ in density, 3.0 in Mw/Mn and 0.42 g/cm$^3$ in bulk density.

What is claimed is:

1. A catalyst for polymerization of olefins comprising a transition metal compound represented by the formula

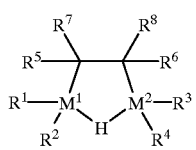

(I)

wherein $M^1$ is an element of Group IVB in the Periodic Table, $M^2$ is an element of Group IIIA in the Periodic Table, $R^1$ and $R^2$ each are a cyclopentadienyl group, a substituted cyclopentadienyl group, an indenyl group or a substituted indenyl group and may be bonded to each other through a $C_1$–$C_{18}$ hydrocarbon group and/or silylene group, $R^3$ and $R^4$ each are a hydrogen atom or a $C_1$–$C_{18}$ hydrocarbon group, $R^5$ and $R^6$ each are a hydrogen atom or a $C_1$–$C_{18}$ hydrocarbon group, and $R^7$ and $R^8$ each are a hydrogen atom or a $C_1$–$C_{18}$ hydrocarbon group and may be bonded to each other to form one or more cyclic hydrocarbon group.

2. A catalyst for polymerization of olefins according to claim 1 wherein said catalyst is a solid catalyst supported on a carrier.

3. A method for producing a polyolefin wherein an olefin is polymerized in the presence of the catalyst of claim 1.

4. A method for producing a polyolefin according to claim 3, wherein an olefin is polymerized in the presence of a scavenger.

5. A method for producing a polyolefin according to claim 4, wherein the scavenger is an organoaluminum compound.

6. A method for producing a polyolefin according to claim 3, wherein the polymerization is homopolymerization of ethylene or copolymerization of ethylene and α-olefin.

7. A catalyst for polymerization of olefins comprising a reaction product formed by reacting a transition metal compound, an organoaluminumoxy compound and/or a compound forming ion pair, wherein said transition metal compound is represented by the formula

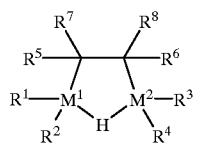

(I)

wherein $M^1$ is an element of Group IVB in the Periodic Table, $M^2$ is an element of Group IIIA in the Periodic Table, $R^1$ and $R^2$ each are a cyclopentadienyl group, a substituted cyclopentadienyl group, an indenyl group or a substituted indenyl group and may be bonded to each other through a $C_1$–$C_{18}$ hydrocarbon group and/or silylene group, $R^3$ and $R^4$ each are a hydrogen atom or a $C_1$–$C_{18}$ hydrocarbon group, $R^5$ and $R^6$ each are a hydrogen atom or a $C_1$–$C_{18}$ hydrocarbon group, and $R^7$ and $R^8$ each are a hydrogen atom or a $C_1$–$C_{18}$ hydrocarbon group and may be bonded to each other to form one or more cyclic hydrocarbon group.

8. A catalyst for polymerization of olefins according to claim 1 wherein said organoaluminumoxy compound is methylalumoxane.

9. A catalyst for polymerization of olefins according to claim 7 wherein said catalyst is a solid catalyst supported on a carrier.

10. A method for producing a polyolefin wherein an olefin is polymerized in the presence of the catalyst of claim 7.

11. A method for producing a polyolefin according to claim 10, wherein an olefin is polymerized in the presence of a scavenger.

12. A method for producing a polyolefin according to claim 11, wherein the scavenger is an organoaluminum compound.

13. A method for producing a polyolefin according to claim 10, wherein the polymerization is homopolymerization of ethylene or copolymerization of ethylene and α-olefin.

\* \* \* \* \*